United States Patent [19]
Nishikura

[11] Patent Number: 5,643,778
[45] Date of Patent: Jul. 1, 1997

[54] RNA EDITING ENZYME AND METHODS OF USE THEREOF

[75] Inventor: Kazuko Nishikura, Haddonfield, N.J.

[73] Assignee: The Wistar Institute of Anatomy & Biology, Philadelphia, Pa.

[21] Appl. No.: 280,443

[22] Filed: Jul. 25, 1994

Related U.S. Application Data

[63] Continuation-in-part of Ser. No. 197,794, Feb. 17, 1994, abandoned.

[51] Int. Cl.$^6$ ............................. C12N 9/78; C12N 15/55; C12N 15/85
[52] U.S. Cl. ...................... 435/227; 435/320.1; 435/348; 435/325; 435/369; 435/358; 435/365; 435/357; 536/23.2; 536/23.5; 536/24.31
[58] Field of Search ................................. 435/227, 240.2, 435/320.1; 536/23.2, 23.5, 24.31

[56] References Cited

U.S. PATENT DOCUMENTS

| | | | |
|---|---|---|---|
| 4,419,446 | 12/1983 | Howley et al. | 435/91 |
| 4,822,736 | 4/1989 | Kellems et al. | 435/91 |
| 5,004,810 | 4/1991 | Draper | 536/24.5 |

OTHER PUBLICATIONS

Hough et al, "The Double–Stranded RNA Adenosine Deaminase" *J. Cell. Biochem. Suppl. 18C*: 130 (Feb. 19, 1994).

Hough et al, "Purification of the *Xenopus laeuis* Double-stranded RNA Adenosine Deaminase", *J. Biol. Chem.* 269(13):9933–9939 (Apr. 1994).

G–S. Feng et al, "Identification of Double–Stranded RNA–binding Domains in the Interferon–induced Double-stranded RNA–activated p68 Kinase", *Proc. Natl. Acad. Sci. USA*, 89:5447–5451 (Jun., 1992).

E. Meurs et al, "Molecular Cloning and Characterization of the Human Double–Stranded RNA–Activated Protein Kinase Induced by Interferon", *Cell*, 62:379–390 (Jul. 27, 1990).

B. Bass et al, "An Unwinding Activity that Covalently Modifies its Double–Stranded RNA Substrate", *Cell*, 55:1089–1098 (Dec. 23, 1988).

B. Bass et al, "A Developmentally Regulated Activity that Unwinds RNA Duplexes", *Cell*, 48:607–613 (Feb. 27, 1987).

B. Bass et al, "Biased Hypermutation of Viral RNA Genomes Could be Due to Unwinding/Modification of Double–Stranded RNA", *Cell*, 56:331 (Feb. 10, 1989).

R. Wagner et al, "A Double–Stranded RNA Unwinding Activity Introduces Structural Alterations by Means of Adenosine to Inosine Conversions in Mammalian Cells and Xenopus Eggs", *Proc. Natl. Acad. Sci. USA*, 86:2647–2651 (Apr. 1989).

R. Wagner et al, "Cell Cycle Expression of RNA Duplex Unwindase Activity in Mammalian Cells", *Mol. Cell Biol.*, 8(2):770–777 (Feb. 1988).

R. Wagner et al, "Double–Stranded RNA Unwinding and Modifying Activity is Detected Ubiquitously in Primary Tissues and Cell Lines", *Mol. Cell Biol.*, 10(10):5586–5590 (Oct. 1990).

R. Wagner et al, "Expression of an RNA Duplex Unwindase Activity in Mammalian Cells" Current Communications in Molecular Biology/Antisense RNA and DNA, D.A. Melton, ed., Cold Spring Harbor Laboratory Press, pp. 103–109 (May 1988).

M. Rebagliati et al, "Antisense RNA Injections in Fertilized Frog Eggs Reveal an RNA Duplex Unwinding Activity", *Cell*, 48:599–605 (Feb. 27, 1987).

Y. Skeiky et al, "Developmental Regulation of Covalent Modification of Double–Stranded RNA During Silkmoth Oogene–sis", *J. Mol. Biol.*, 218:517–527 (Apr. 5, 1991).

A. Polson et al, "The Mechanism of Adenosine to Inosine Conversion by the Double–Stranded RNA Unwinding/Modifying Activity: A High–Performance Liquid Chromatography–Mass Spectrometry Analysis", *Biochem.*, 30:11507–11514 (Dec. 10, 1991).

K. Nishikura et al, "Substrate Specificity of the dsRNA Unwinding/Modifying Activity", *EMBO J.*, 10(11):3523–3532 (Oct. 11, 1991).

K. Nishikura et al, "Modulation of Double–Stranded RNAs in vivo by RNA Duplex Unwindase" *Annals of the New York Acad. of Sci.*, 660:240–250 (Oct. 28, 1992).

K. Nishikura, "A Cellular Activity that Modifies and Alters the Structure of Double–Stranded RNA" *Gene Regulation: Biology of Antisense RNA and DNA*, R.P. Erickson and J.G. Izant, Raven Press Ltd., NY, pp. 21–34 (Dec. 11, 1991).

D. Kimelman et al. "An Antisense mRNA Directs the Covalent Modification of the Transcript Encoding Fibroblast Growth Factor in Xenopus Oocytes", *Cell*, 59:687–696 (Nov. 17, 1989).

R. Cattaneo et al, "Biased Hypermutation and Other Genetic Changes in Defective Measles Viruses in Human Brain Infections", *Cell*, 55:255–265 (Oct. 21, 1988).

L. Sharmeen et al, "Tat–dependent Adenosine–to–Inosine Modification of Wild–type Transactivation Response RNA", *Proc. Natl. Acad. Sci. USA*, 88:8096–8100 (Sep. 1991).

U. Kim et al, "Double–Stranded RNA Adenosine Deaminase: A Potential Agent for RNA Editing?" in RNA Editing, R. Benne, Ed. (Simon and Schuster Intnl., Chichester, England, pp. 179–192 (July 1993).

U. Kim et al, "Double–Stranded RNA Adenosine Deaminase as a Potential Mammalian RNA Editing Factor", *Cell Biology*, 4:285–293 (Aug. 19, 1993).

U. Kim et al, "Purification and Characterization of Double-stranded RNA Adenosine Deaminease from Bovine Nuclear Extracts" *J. Biol. Chem.*, 269(18):13480–13489 (May 6, 1994).

B. Sommer et al, "RNA Editing in Brain Controls a Determinant of Ion Flow in Glutamate–Gated Channels", *Cell*, 67:11–19 (Oct. 4, 1991).

T. Verdoorn et al, "Structural Determinants of Ion Flow Through Recombinant Glutamate Receptor Channels", *Science*, 252:1715–718 (Jun. 21, 1991).

M. Kohler et al, "Determinants of $Ca_2+$ Permeability in Both TM1 and TM2 of High Affinity Kainate Receptor Channels: Diversity by RNA Editing", *Neuron*, 10:491–500 (Mar. 1993).

M. Higuchi et al, "RNA Editing of AMPA Receptor Subunit GluR–B: A Base–Paired Intron Exon Structure Determines Position and Efficiency", *Cell*, 75(7):1361–1370 (Dec. 31, 1993).

S. Rataul et al, "Irreversible Modification of Measles Virus RNA in Virtro by Nuclear RNA–Unwinding Activity in Human Neuroblastoma Cells", *J. Virol.*, 66 (3):1769–1773 (Mar. 1992).

J. Thakkar et al, "Isolation and Characterization of AMP Deaminase from Mammalian (Rabbit) Myocardium", *Biochem. J.*, 290:335–341 (Mar. 1, 1993).

C. Yang et al, "Cloning and Nucleotide Sequence of the *Escherichia coli* Cytidine Deaminase (ccd) Gene", *Biochemistry*, 31:4168–4174 (May 5, 1992).

D. Wilson et al, "Atomic Structure of Adenosine Deaminase Complexed with a Transiton–State Analog: Understanding Catalysis and Immunodeficiency Mutations", *Science*, 252:1278–1284 (May 31, 1991).

G. Cesareni, "Peptide Display on Filamentous Phage Capsids—A New Powerful Tool to Study Protein–Ligand Interaction", *FEBS Letters*, 307(1):66–70 (Jul. 1992).

H. Gram et al, "Phage Display as a Rapid Gene Expression System: Production of Bioactive Cytokine–Phage and Generation of Neutralizing Monoclonal Antibodies", *J. Immunol. Methods*, 161:169–176 (May 27, 1993).

J. Grinspan et al, "Bovine Endothelial Cells Transformed in Vitro by Benzo(a)pyrene", *J. Cell Physiol.*, 114:328–338 (1983).

A. Gatignol et al, "Relatedness of an RNA–Binding Motif in Human Immunodeficiency Virus Type 1 TAR RNA–Binding Protein TRBP to Human P1/dsI Kinase and Drosophila Staufen", *Mol. Cell. Biol*, 13 (4):2193–2202 (Apr. 1993).

D. St. Johnston et al, "A Conserved Double–Stranded RNA–Binding Domain", *Proc. Natl. Acad. Sci. USA*, 89:10979–10983 (Nov. 1992).

D. Miller et al, "An Insect Baculovirus Host–Vector System for High–Level Expression of Foreign Genes", *Genetic Engineering*, 8:277–298 (May 1986).

M. Gething et al, "Cell–Surface Expression of Influenza Haemagglutinin from a Cloned DNA Copy of the RNA Gene", *Nature*, 293:620–625 (Oct. 1981).

R. Kaufman et al, "Coamplification and Coexpression of Human Tissue–Type Plasminogen Activator and Murine Dihydrofolate Reductase Sequences in Chinese Hamster Ovary Cells", *Mol. Cell Biol.*, 5(7):1750–1759 (Jul. 1985).

C. Swimmer et al, "Phage Display of Ricin B Chain and its Single Binding Domains: System for Screening Galactose-–Binding Mutants", *Proc. Natl. Acad. Sci. USA*, 89:3756–3760 (May 1992).

J. Dignam et al, "Accurate Transcription Initiation by RNA Polymerase II in a Soluble Extract from Isolated Mammalian Nuclei", *Nucleic Acids Res.*, 11(5):1475–1489 (Mar. 1983).

M. SilberKlang et al, "Use of in Vitro $^{32}P$ Labeling in the Sequence Analysis of Nonradioactive tRNAs", *Methods Enzymol.*, 59:58–109 (Apr. 28, 1978).

C. Lee et al, "cDNA Cloning Using Degenerate Primers", in *PCR Protocols: A Guide to Methods and Application*, M. A. Innis et al, Eds., Academic Press, Inc., San Diego, CA, pp. 46–53 (Dec. 28, 1989).

M. Kozak, "The Scanning Model for Translation: An Update", *J. Cell Biol.*, 108:229–241 (Feb. 14, 1989).

J. Devereux et al, "A Comprehensive Set of Sequence Analysis Programs for the VAX", *Nucleic Acids Res.*, 12(1):387–395 (Jan. 1984).

S. Haynes, "Research Review: The RNP Motif Protein Family", *New Biol.*, 4(5):421–429 (May 1992).

Z. Chang et al, "Deduced Amino Acid Sequence of *Escherichia coli* Adenosine Deaminase Reveals Evolutionarily Conserved Amino Acid Residues: Implications for Catalytic Function", *Biochem.*, 30:2273–2280 (Feb. 26, 1991).

B. Teng et al, "Molecular Cloning of an Apolipoprotein B Messenger RNA Editing Protein", *Science*, 260:1816–1819 (Jun. 1993).

R. Wilson et al, "2.2 Mb of Contiguous Nucleotide Sequence from Chromosome III of C. elegans", *Nature (London)*, 368:32–38 (Mar. 1994).

Adams et al, "3,400 New Expressed Sequence Tags Identify Diversity of Transcripts from Human Brain," *Nature Genet.*, 4:256–267 (Jul. 1993).

Miki et al, "Disruption of the APC Gene by a Retrotransposal Insertion of L1 Sequence in Colon Cancer", *Cancer Res.*, 52:643–645 (Feb. 1992).

Sambrook et al, *Molecular Cloning*, 2d ed., p. 163 (Nov. 1989).

Huynh et al, "Constructing and Screening cDNA Libraries in λgt10 and λgt11," *DNA Cloning*, ed. Glover, IRL Press, pp. 49–78 (Aug. 1985).

Lathe et al, "Synthetic Oligonucleotide Probes Deduced from Amino Acid Sequence Data, " *J. Mol. Biol.*, 183(1):1–12 (May 1985).

*Primary Examiner*—Robert A. Wax
*Assistant Examiner*—Tekchand Saidha
*Attorney, Agent, or Firm*—Howson and Howson

[57] ABSTRACT

The present invention provides novel human polynucleotide sequences and the recombinant human double-stranded RNA adenosine deaminase enzyme (DRADA) proteins encoded thereby and methods of use thereof.

8 Claims, 15 Drawing Sheets

FIGURE 1A

```
CGCAGACCCG CGGAGTTTCC CGTGCCGACG CCCCGGGGCC ACTTCCAGTG        50

CGGAGTAGCG GAGGCGTGGG GGCCTCGAGG GGCTGGCGCG GTCCAGCGGT       100

CGGGCCAGGG TCGTGCCGCC GGCGGGTCGG GCCGGACAAT GCCTCGCGGG       150

CGCA ATG AAT CCG CGG CAG GGG TAT TCC CTC AGC GGA TAC TAC     193
     Met Asn Pro Arg Gln Gly Tyr Ser Leu Ser Gly Tyr Tyr
      1               5                  10

ACC CAT CCA TTT CAA GGC TAT GAG CAC AGA CAG CTC AGA TAC      235
Thr His Pro Phe Gln Gly Tyr Glu His Arg Gln Leu Arg Tyr
     15              20                  25

CAG CAG CCT GGG CCA GGA TCT TCC CCC AGT AGT TTC CTG CTT      277
Gln Gln Pro Gly Pro Gly Ser Ser Pro Ser Ser Phe Leu Leu
         30              35                  40

AAG CAA ATA GAA TTT CTC AAG GGG CAG CTC CCA GAA GCA CCG      319
Lys Gln Ile Glu Phe Leu Lys Gly Gln Leu Pro Glu Ala Pro
             45              50                  55

GTG ATT GGA AAG CAG ACA CCG TCA CTG CCA CCT TCC CTC CCA      361
Val Ile Gly Lys Gln Thr Pro Ser Leu Pro Pro Ser Leu Pro
                 60              65

GGA CTC CGG CCA AGG TTT CCA GTA CTA CTT GCC TCC AGT ACC      403
Gly Leu Arg Pro Arg Phe Pro Val Leu Leu Ala Ser Ser Thr
 70              75                  80

AGA GGC AGG CAA GTG GAC ATC AGG GGT GTC CCC AGG GGC GTG      445
Arg Gly Arg Gln Val Asp Ile Arg Gly Val Pro Arg Gly Val
     85              90                  95

CAT CTC GGA AGT CAG GGG CTC CAG AGA GGG TTC CAG CAT CCT      487
His Leu Gly Ser Gln Gly Leu Gln Arg Gly Phe Gln His Pro
         100             105                 110

TCA CCA CGT GGC AGG AGT CTG CCA CAG AGA GGT GTT GAT TGC      529
Ser Pro Arg Gly Arg Ser Leu Pro Gln Arg Gly Val Asp Cys
             115             120                 125

CTT TCC TCA CAT TTC CAG GAA CTG AGT ATC TAC CAA GAT CAG      571
Leu Ser Ser His Phe Gln Glu Leu Ser Ile Tyr Gln Asp Gln
                 130             135

GAA CAA AGG ATC TTA AAG TTC CTG GAA GAG CTT GGG GAA GGG      613
Glu Gln Arg Ile Leu Lys Phe Leu Glu Glu Leu Gly Glu Gly
 140             145                 150
```

FIGURE 1B

| | | | | | | | | | | | | | |
|---|---|---|---|---|---|---|---|---|---|---|---|---|---|
| AAG | GCC | ACC | ACA | GCA | CAT | GAT | CTG | TCT | GGG | AAA | CTT | GGG | ACT | 655 |
| Lys | Ala | Thr | Thr | Ala | His | Asp | Leu | Ser | Gly | Lys | Leu | Gly | Thr | |
| | 155 | | | | 160 | | | | | 165 | | | | |
| CCG | AAG | AAA | GAA | ATC | AAT | CGA | GTT | TTA | TAC | TCC | CTG | GCA | AAG | 697 |
| Pro | Lys | Lys | Glu | Ile | Asn | Arg | Val | Leu | Tyr | Ser | Leu | Ala | Lys | |
| | | 170 | | | | | 175 | | | | | 180 | | |
| AAG | GGC | AAG | CTA | CAG | AAA | GAG | GCA | GGA | ACA | CCC | CCT | TTG | TGG | 739 |
| Lys | Gly | Lys | Leu | Gln | Lys | Glu | Ala | Gly | Thr | Pro | Pro | Leu | Trp | |
| | | | 185 | | | | | 190 | | | | | 195 | |
| AAA | ATC | GCG | GTC | TCC | ACT | CAG | GCT | TGG | AAC | CAG | CAC | AGC | GGA | 781 |
| Lys | Ile | Ala | Val | Ser | Thr | Gln | Ala | Trp | Asn | Gln | His | Ser | Gly | |
| | | | | 200 | | | | | 205 | | | | | |
| GTG | GTA | AGA | CCA | GAC | GGT | CAT | AGC | CAA | GGA | GCC | CCA | AAC | TCA | 823 |
| Val | Val | Arg | Pro | Asp | Gly | His | Ser | Gln | Gly | Ala | Pro | Asn | Ser | |
| 210 | | | | | 215 | | | | | 220 | | | | |
| GAC | CCG | AGT | TTG | GAA | CCG | GAA | GAC | AGA | AAC | TCC | ACA | TCT | GTC | 865 |
| Asp | Pro | Ser | Leu | Glu | Pro | Glu | Asp | Arg | Asn | Ser | Thr | Ser | Val | |
| | 225 | | | | | 230 | | | | | 235 | | | |
| TCA | GAA | GAT | CTT | CTT | GAG | CCT | TTT | ATT | GCA | GTC | TCA | GCT | CAG | 907 |
| Ser | Glu | Asp | Leu | Leu | Glu | Pro | Phe | Ile | Ala | Val | Ser | Ala | Gln | |
| | | 240 | | | | | 245 | | | | | 250 | | |
| GCT | TGG | AAC | CAG | CAC | AGC | GGA | GTG | GTA | AGA | CCA | GAC | AGT | CAT | 949 |
| Ala | Trp | Asn | Gln | His | Ser | Gly | Val | Val | Arg | Pro | Asp | Ser | His | |
| | | | 255 | | | | | 260 | | | | | 265 | |
| AGC | CAA | GGA | TCC | CCA | AAC | TCA | GAC | CCA | GGT | TTG | GAA | CCT | GAA | 991 |
| Ser | Gln | Gly | Ser | Pro | Asn | Ser | Asp | Pro | Gly | Leu | Glu | Pro | Glu | |
| | | | | 270 | | | | | 275 | | | | | |
| GAC | AGC | AAC | TCC | ACA | TCT | GCC | TTG | GAA | GAT | CCT | CTT | GAG | TTT | 1033 |
| Asp | Ser | Asn | Ser | Thr | Ser | Ala | Leu | Glu | Asp | Pro | Leu | Glu | Phe | |
| 280 | | | | | 285 | | | | | 290 | | | | |
| TTA | GAC | ATG | GCC | GAG | ATC | AAG | GAG | AAA | ATC | TGC | GAC | TAT | CTC | 1075 |
| Leu | Asp | Met | Ala | Glu | Ile | Lys | Glu | Lys | Ile | Cys | Asp | Tyr | Leu | |
| | | 295 | | | | | 300 | | | | | 305 | | |
| TTC | AAT | GTG | TCT | GAC | TCC | TCT | GCC | CTG | AAT | TTG | GCT | AAA | AAT | 1117 |
| Phe | Asn | Val | Ser | Asp | Ser | Ser | Ala | Leu | Asn | Leu | Ala | Lys | Asn | |
| | | | 310 | | | | | 315 | | | | | 320 | |
| ATT | GGC | CTT | ACC | AAG | GCC | CGA | GAT | ATA | AAT | GCT | GTG | CTA | ATT | 1159 |
| Ile | Gly | Leu | Thr | Lys | Ala | Arg | Asp | Ile | Asn | Ala | Val | Leu | Ile | |
| | | | | 325 | | | | | 330 | | | | | 335 |

FIGURE 1C

```
GAC ATG GAA AGG CAG GGG GAT GTC TAT AGA CAA GGG ACA ACC   1201
Asp Met Glu Arg Gln Gly Asp Val Tyr Arg Gln Gly Thr Thr
            340                 345

CCT CCC ATA TGG CAT TTG ACA GAC AAG AAG CGA GAG AGG ATG   1243
Pro Pro Ile Trp His Leu Thr Asp Lys Lys Arg Glu Arg Met
350             355                 360

CAA ATC AAG AGA AAT ACG AAC AGT GTT CCT GAA ACC GCT CCA   1285
Gln Ile Lys Arg Asn Thr Asn Ser Val Pro Glu Thr Ala Pro
        365             370                 375

GCT GCA ATC CCT GAG ACC AAA AGA AAC GCA GAG TTC CTC ACC   1327
Ala Ala Ile Pro Glu Thr Lys Arg Asn Ala Glu Phe Leu Thr
            380                 385                 390

┌--->93 kd
TGT AAT ATA CCC ACA TCA AAT GCC TCA AAT AAC ATG GTA ACC   1369
Cys Asn Ile Pro Thr Ser Asn Ala Ser Asn Asn Met Val Thr
            395                 400                 405

ACA GAA AAA GTG GAG AAT GGG CAG GAA CCT GTC ATA AAG TTA   1411
Thr Glu Lys Val Glu Asn Gly Gln Glu Pro Val Ile Lys Leu
                410                 415

GAA AAC AGG CAA GAG GCC AGA CCA GAA CCA GCA AGA CTG AAA   1453
Glu Asn Arg Gln Glu Ala Arg Pro Glu Pro Ala Arg Leu Lys
420                 425                 430

┌--->88 kd
CCA CCT GTT CAT TAC AAT GGC CCC TCA AAA GCA GGG TAT GTT   1495
Pro Pro Val His Tyr Asn Gly Pro Ser Lys Ala Gly Tyr Val
        435                 440                 445

GAC TTT GAA AAT GGC CAG TGG GCC ACA GAT GAC ATC CCA GAT   1537
Asp Phe Glu Asn Gly Gln Trp Ala Thr Asp Asp Ile Pro Asp
            450                 455                 460

GAC TTG AAT AGT ATC CGC GCA GCA CCA GGT GAG TTT CGA GCC   1579
Asp Leu Asn Ser Ile Arg Ala Ala Pro Gly Glu Phe Arg Ala
            465                 470                 475

ATC ATG GAG ATG CCC TCC TTC TAC AGT CAT GGC TTG CCA CGG   1621
Ile Met Glu Met Pro Ser Phe Tyr Ser His Gly Leu Pro Arg
            480                 485

TGT TCA CCC TAC AAG AAA CTG ACA GAG TGC CAG CTG AAG AAC   1663
Cys Ser Pro Tyr Lys Lys Leu Thr Glu Cys Gln Leu Lys Asn
490             495                 500
```

FIGURE 1D

| | | | | | | | | | | | | | |
|---|---|---|---|---|---|---|---|---|---|---|---|---|---|
| CCC | ATC | AGC | GGG | CTG | TTA | GAA | TAT | GCC | CAG | TTC | GCT | AGT | CAA | 1705
| Pro | Ile | Ser | Gly | Leu | Leu | Glu | Tyr | Ala | Gln | Phe | Ala | Ser | Gln |
| | 505 | | | | 510 | | | | | 515 | | | |
| ACC | TGT | GAG | TTC | AAC | ATG | ATA | GAG | CAG | AGT | GGA | CCA | CCC | CAT | 1747
| Thr | Cys | Glu | Phe | Asn | Met | Ile | Glu | Gln | Ser | Gly | Pro | Pro | His |
| | | 520 | | | | 525 | | | | | 530 | | |

DRBM1

| | | | | | | | | | | | | | |
|---|---|---|---|---|---|---|---|---|---|---|---|---|---|
| GAA | CCT | CGA | TTT | AAA | TTC | CAG | GTT | GTC | ATC | AAT | GGC | CGA | GAG | 1789
| Glu | Pro | Arg | Phe | Lys | Phe | Gln | Val | Val | Ile | Asn | Gly | Arg | Glu |
| | | | 535 | | | | 540 | | | | | 545 | |
| TTT | CCC | CCA | GCT | GAA | GCT | GGA | AGC | AAG | AAA | GTG | GCC | AAG | CAG | 1831
| Phe | Pro | Pro | Ala | Glu | Ala | Gly | Ser | Lys | Lys | Val | Ala | Lys | Gln |
| | | | | 550 | | | | | 555 | | | | |
| GAT | GCA | GCT | ATG | AAA | GCC | ATG | ACA | ATT | CTG | CTA | GAG | GAA | GCC | 1873
| Asp | Ala | Ala | Met | Lys | Ala | Met | Thr | Ile | Leu | Leu | Glu | Glu | Ala |
| 560 | | | | | 565 | | | | | 570 | | | |
| AAA | GCC | AAG | GAC | AGT | GGA | AAA | TCA | GAA | GAA | TCA | TCC | CAC | TAT | 1915
| Lys | Ala | Lys | Asp | Ser | Gly | Lys | Ser | Glu | Glu | Ser | Ser | His | Tyr |
| | 575 | | | | | 580 | | | | | 585 | | |
| TCC | ACA | GAG | AAA | GAA | TCA | GAG | AAG | ACT | GCA | GAG | TCC | CAG | ACC | 1957
| Ser | Thr | Glu | Lys | Glu | Ser | Glu | Lys | Thr | Ala | Glu | Ser | Gln | Thr |
| | | 590 | | | | | 595 | | | | | 600 | |
| CCC | ACC | CCT | TCA | GCC | ACA | TCC | TTC | TTT | TCT | GGG | AAG | AGC | CCC | 1999
| Pro | Thr | Pro | Ser | Ala | Thr | Ser | Phe | Phe | Ser | Gly | Lys | Ser | Pro |
| | | | | 605 | | | | | 610 | | | | 615 |
| GTC | ACC | ACA | CTG | CTT | GAG | TGT | ATG | CAC | AAA | TTG | GGG | AAC | TCC | 2041
| Val | Thr | Thr | Leu | Leu | Glu | Cys | Met | His | Lys | Leu | Gly | Asn | Ser |
| | | | | 620 | | | | | 625 | | | | |
| TGC | GAA | TTC | CGT | CTC | CTG | TCC | AAA | GAA | GGC | CCT | GCC | CAT | GAA | 2083
| Cys | Glu | Phe | Arg | Leu | Leu | Ser | Lys | Glu | Gly | Pro | Ala | His | Glu |
| 630 | | | | | 635 | | | | | 640 | | | |

DRBM2

| | | | | | | | | | | | | | |
|---|---|---|---|---|---|---|---|---|---|---|---|---|---|
| CCC | AAG | TTC | CAA | TAC | TGT | GTT | GCA | GTG | GGA | GCC | CAA | ACT | TTC | 2125
| Pro | Lys | Phe | Gln | Tyr | Cys | Val | Ala | Val | Gly | Ala | Gln | Thr | Phe |
| | 645 | | | | | 650 | | | | | 655 | | |
| CCC | AGT | GTG | AGT | GCT | CCC | AGC | AAG | AAA | GTG | GCA | AAG | CAG | ATG | 2167
| Pro | Ser | Val | Ser | Ala | Pro | Ser | Lys | Lys | Val | Ala | Lys | Gln | Met |
| | | 660 | | | | | 665 | | | | | 670 | |

FIGURE 1E

| | | | | | | | | | | | | | |
|---|---|---|---|---|---|---|---|---|---|---|---|---|---|
| GCC | GCA | GAG | GAA | GCC | ATG | AAG | GCC | CTG | CAT | GGG | GAG | GCG | ACC | 2209 |
| Ala | Ala | Glu | Glu | Ala | Met | Lys | Ala | Leu | His | Gly | Glu | Ala | Thr |
| | | | 675 | | | | 680 | | | | | | 685 |

| AAC | TCC | ATG | GCT | TCT | GAT | AAC | CAG | CCT | GAA | GGT | ATG | ATC | TCA | 2251 |
| Asn | Ser | Met | Ala | Ser | Asp | Asn | Gln | Pro | Glu | Gly | Met | Ile | Ser |
| | | | | 690 | | | | | 695 | | | | |

| GAG | TCA | CTT | GAT | AAC | TTG | GAA | TCC | ATG | ATG | CCC | AAC | AAG | GTC | 2293 |
| Glu | Ser | Leu | Asp | Asn | Leu | Glu | Ser | Met | Met | Pro | Asn | Lys | Val |
| 700 | | | | | 705 | | | | | 710 | | | |

| AGG | AAG | ATT | GGC | GAG | CTC | GTG | AGA | TAC | CTG | AAC | ACC | AAC | CCT | 2335 |
| Arg | Lys | Ile | Gly | Glu | Leu | Val | Arg | Tyr | Leu | Asn | Thr | Asn | Pro |
| | 715 | | | | | 720 | | | | | 725 | | |

| GTG | GGT | GGC | CTT | TTG | GAG | TAC | GCC | CGC | TCC | CAT | GGC | TTT | GCT | 2377 |
| Val | Gly | Gly | Leu | Leu | Glu | Tyr | Ala | Arg | Ser | His | Gly | Phe | Ala |
| | | 730 | | | | | 735 | | | | | 740 | |

| GCT | GAA | TTC | AAG | TTG | GTC | GAC | CAG | TCC | GGA | CCT | CCT | CAC | GAG | 2419 |
| Ala | Glu | Phe | Lys | Leu | Val | Asp | Gln | Ser | Gly | Pro | Pro | His | Glu |
| | | | 745 | | | | | 750 | | | | | 755 |

DRBM3

| CCC | AAG | TTC | GTT | TAC | CAA | GCA | AAA | GTT | GGG | GGT | CGC | TGG | TTC | 2461 |
| Pro | Lys | Phe | Val | Tyr | Gln | Ala | Lys | Val | Gly | Gly | Arg | Trp | Phe |
| | | | | 760 | | | | | 765 | | | | |

| CCA | GCC | GTC | TGC | GCA | CAC | AGC | AAG | AAG | CAA | GGC | AAG | CAG | GAA | 2503 |
| Pro | Ala | Val | Cys | Ala | His | Ser | Lys | Lys | Gln | Gly | Lys | Gln | Glu |
| 770 | | | | | 775 | | | | | 780 | | | |

| GCA | GCA | GAT | GCG | GCT | CTC | CGT | GTC | TTG | ATT | GGG | GAG | AAC | GAG | 2545 |
| Ala | Ala | Asp | Ala | Ala | Leu | Arg | Val | Leu | Ile | Gly | Glu | Asn | Glu |
| | 785 | | | | | 790 | | | | | 795 | | |

| AAG | GCA | GAA | CGC | ATG | GGT | TTC | ACA | GAG | GTA | ACC | CCA | GTG | ACA | 2587 |
| Lys | Ala | Glu | Arg | Met | Gly | Phe | Thr | Glu | Val | Thr | Pro | Val | Thr |
| | | 800 | | | | | 805 | | | | | 810 | |

| GGG | GCC | AGT | CTC | AGA | AGA | ACT | ATG | CTC | CTC | CTC | TCA | AGG | TCC | 2629 |
| Gly | Ala | Ser | Leu | Arg | Arg | Thr | Met | Leu | Leu | Leu | Ser | Arg | Ser |
| | | | 815 | | | | | 820 | | | | | 825 |

| CCA | GAA | GCA | CAG | CCA | AAG | ACA | CTC | CCT | CTC | ACT | GGC | AGC | ACC | 2671 |
| Pro | Glu | Ala | Gln | Pro | Lys | Thr | Leu | Pro | Leu | Thr | Gly | Ser | Thr |
| | | | | 830 | | | | | 835 | | | | |

FIGURE 1F

| | | | | | | | | | | | | | |
|---|---|---|---|---|---|---|---|---|---|---|---|---|---|
| TTC | CAT | GAC | CAG | ATA | GCC | ATG | CTG | AGC | CAC | CGG | TGC | TTC | AAC | 2713 |
| Phe | His | Asp | Gln | Ile | Ala | Met | Leu | Ser | His | Arg | Cys | Phe | Asn |
| 840 | | | | | 845 | | | | | 850 | | | |

| ACT | CTG | ACT | AAC | AGC | TTC | CAG | CCC | TCC | TTG | CTC | GGC | CGC | AAG | 2755 |
| Thr | Leu | Thr | Asn | Ser | Phe | Gln | Pro | Ser | Leu | Leu | Gly | Arg | Lys |
| | | 855 | | | | | 860 | | | | | 865 | |

| ATT | CTG | GCC | GCC | ATC | ATT | ATG | AAA | AAA | GAC | TCT | GAG | GAC | ATG | 2797 |
| Ile | Leu | Ala | Ala | Ile | Ile | Met | Lys | Lys | Asp | Ser | Glu | Asp | Met |
| | | | 870 | | | | | 875 | | | | | 880 |

| GGT | GTC | GTC | GTC | AGC | TTG | GGA | ACA | GGG | AAT | CGC | TGT | GTG | AAA | 2839 |
| Gly | Val | Val | Val | Ser | Leu | Gly | Thr | Gly | Asn | Arg | Cys | Val | Lys |
| | | | | 885 | | | | | 890 | | | | 895 |

| GGA | GAT | TCT | CTC | AGC | CTA | AAA | GGA | GAA | ACT | GTC | AAT | GAC | TGC | 2881 |
| Gly | Asp | Ser | Leu | Ser | Leu | Lys | Gly | Glu | Thr | Val | Asn | Asp | Cys |
| | | | | | 900 | | | | | 905 | | | |

| CAT | GCA | GAA | ATA | ATC | TCC | CGG | AGA | GGC | TTC | ATC | AGG | TTT | CTC | 2923 |
| His | Ala | Glu | Ile | Ile | Ser | Arg | Arg | Gly | Phe | Ile | Arg | Phe | Leu |
| 910 | | | | | 915 | | | | | 920 | | | |

| TAC | AGT | GAG | TTA | ATG | AAA | TAC | AAC | TCC | CAG | ACT | GCG | AAG | GAT | 2965 |
| Tyr | Ser | Glu | Leu | Met | Lys | Tyr | Asn | Ser | Gln | Thr | Ala | Lys | Asp |
| | 925 | | | | | 930 | | | | | 935 | | |

| AGT | ATA | TTT | GAA | CCT | GCT | AAG | GGA | GGA | GAA | AAG | CTC | CAA | ATA | 3007 |
| Ser | Ile | Phe | Glu | Pro | Ala | Lys | Gly | Gly | Glu | Lys | Leu | Gln | Ile |
| | | | 940 | | | | | 945 | | | | | 950 |

| AAA | AAG | ACT | GTG | TCA | TTC | CAT | CTG | TAT | ATC | AGC | ACT | GCT | CCG | 3049 |
| Lys | Lys | Thr | Val | Ser | Phe | His | Leu | Tyr | Ile | Ser | Thr | Ala | Pro |
| | | | | 955 | | | | | 960 | | | | 965 |

| TGT | GGA | GAT | GGC | GCC | CTC | TTT | GAC | AAG | TCC | TGC | AGC | GAC | CGT | 3091 |
| Cys | Gly | Asp | Gly | Ala | Leu | Phe | Asp | Lys | Ser | Cys | Ser | Asp | Arg |
| | | | | 970 | | | | | 975 | | | | |

| GCT | ATG | GAA | AGC | ACA | GAA | TCC | CGC | CAC | TAC | CCT | GTC | TTC | GAG | 3133 |
| Ala | Met | Glu | Ser | Thr | Glu | Ser | Arg | His | Tyr | Pro | Val | Phe | Glu |
| 980 | | | | | 985 | | | | | 990 | | | |

| AAT | CCC | AAA | CAA | GGA | AAG | CTC | CGC | ACC | AAG | GTG | GAG | AAC | GGA | 3175 |
| Asn | Pro | Lys | Gln | Gly | Lys | Leu | Arg | Thr | Lys | Val | Glu | Asn | Gly |
| | 995 | | | | | 1000 | | | | | 1005 | | |

| GAA | GGC | ACA | ATC | CCT | GTG | GAA | TCC | AGT | GAC | ATT | GTG | CCT | ACG | 3217 |
| Glu | Gly | Thr | Ile | Pro | Val | Glu | Ser | Ser | Asp | Ile | Val | Pro | Thr |
| | | 1010 | | | | | 1015 | | | | | 1020 | |

FIGURE 1G

| | | | | | | | | | | | | | |
|---|---|---|---|---|---|---|---|---|---|---|---|---|---|
| TGG | GAT | GGC | ATT | CGG | CTC | GGG | GAG | AGA | CTC | CGT | ACC | ATG | TCC | 3259 |
| Trp | Asp | Gly | Ile | Arg | Leu | Gly | Glu | Arg | Leu | Arg | Thr | Met | Ser |
| | | | 1025 | | | | 1030 | | | | | 1035 |

```
TGG GAT GGC ATT CGG CTC GGG GAG AGA CTC CGT ACC ATG TCC    3259
Trp Asp Gly Ile Arg Leu Gly Glu Arg Leu Arg Thr Met Ser
            1025            1030                1035

TGT AGT GAC AAA ATC CTA CGC TGG AAC GTG CTG GGC CTG CAA    3301
Cys Ser Asp Lys Ile Leu Arg Trp Asn Val Leu Gly Leu Gln
            1040            1045

GGG GCA CTG TTG ACC CAC TTC CTG CAG CCC ATT TAT CTC AAA    3343
Gly Ala Leu Leu Thr His Phe Leu Gln Pro Ile Tyr Leu Lys
1050                1055                1060

TCT GTC ACA TTG GGT TAC CTT TTC AGC CAA GGG CAT CTG ACC    3385
Ser Val Thr Leu Gly Tyr Leu Phe Ser Gln Gly His Leu Thr
        1065            1070                1075

CGT GCT ATT TGC TGT CGT GTG ACA AGA GAT GGG AGT GCA TTT    3427
Arg Ala Ile Cys Cys Arg Val Thr Arg Asp Gly Ser Ala Phe
            1080            1085                1090

GAG GAT GGA CTA CGA CAT CCC TTT ATT GTC AAC CAC CCC AAG    3469
Glu Asp Gly Leu Arg His Pro Phe Ile Val Asn His Pro Lys
                1095            1100                1105

GTT GGC AGA GTC AGC ATA TAT GAT TCC AAA AGG CAA TCC GGG    3511
Val Gly Arg Val Ser Ile Tyr Asp Ser Lys Arg Gln Ser Gly
                1110            1115

AAG ACT AAG GAG ACA AGC GTC AAC TGG TGT CTG GCT GAT GGC    3553
Lys Thr Lys Glu Thr Ser Val Asn Trp Cys Leu Ala Asp Gly
1120            1125            1130

TAT GAC CTG GAG ATC CTG GAC GGT ACC AGA GGC ACT GTG GAT    3595
Tyr Asp Leu Glu Ile Leu Asp Gly Thr Arg Gly Thr Val Asp
        1135                1140            1145

GGG CCA CGG AAT GAA TTG TCC CGG GTC TCC AAA AAG AAC ATT    3637
Gly Pro Arg Asn Glu Leu Ser Arg Val Ser Lys Lys Asn Ile
            1150            1155                1160

TTT CTT CTA TTT AAG AAG CTC TGC TCC TTC CGT TAC CGC AGG    3679
Phe Leu Leu Phe Lys Lys Leu Cys Ser Phe Arg Tyr Arg Arg
                1165            1170                1175

GAT CTA CTG AGA CTC TCC TAT GGT GAG GCC AAG AAA GCT GCC    3721
Asp Leu Leu Arg Leu Ser Tyr Gly Glu Ala Lys Lys Ala Ala
                    1180            1185

CGT GAC TAC GAG ACG GCC AAG AAC TAC TTC AAA AAA GGC CTG    3763
Arg Asp Tyr Glu Thr Ala Lys Asn Tyr Phe Lys Lys Gly Leu
1190            1195                1200
```

FIGURE 1H

| | | | | | | | | | | | | |
|---|---|---|---|---|---|---|---|---|---|---|---|---|
| AAG | GAT | ATG | GGC | TAT | GGG | AAC | TGG | ATT | AGC | AAA | CCC | CAG GAG | 3805
| Lys | Asp | Met | Gly | Tyr | Gly | Asn | Trp | Ile | Ser | Lys | Pro | Gln Glu |
| | | 1205 | | | | 1210 | | | | | 1215 | |

| GAA | AAG | AAC | TTT | TAT | CTC | TGC | CCA | GTA | TAGTATGCTC | 3842
|---|---|---|---|---|---|---|---|---|---|---|
| Phe | Tyr | Glu | Lys | Asn | Leu | Cys | Pro | Val | | |
| | | 1220 | | | | 1225 | | | | |

CAGTGACAGA TGGATTAGGG TGTGTCATAC TAGGGTGTGA GAGAGGTAGG 3892

TCGTAGCATT CCTCATCACA TGGTCAGGGG ATTTTTTTTT CTCCTTTTTT 3942

TTTTCTTTTT AAGCCATAAT TGGTGATACT GAAAACTTTG GGTTCCCATT 3992

TATCCTGCTT TCTTTGGGAT TGCTAGGCAA GGTCTGGCCA GGCCCCCTT 4042

TTTTCCCCCA AGTGAAGAGG CAGAAACCTA AGAAGTTATC TTTTCTTTCT 4092

ACCCAAAGCA TACATAGTCA CTGAGCACCT GCGGTCCATT TCCTCTTAAA 4142

AGTTTTGTTT TGATTTGTTT CCATTTCCTT TCCCTTTGTG TTTGCTACAC 4192

TGACCTCTTG CGGTCTTGAT TAGGTTTCAG TCAACTCTGG ATCATGTCAG 4242

GGACTGATAA TTTCATTTGT GGATTACGCA GACCCTCTA CTTCCCCTCT 4292

TTCCTTCTG AGATTCTTTC CTTGTGATCT GAATGTCTCC TTTTCCCCCT 4342

CAGAGGGCAA AGAGGTGAAC ATAAAGGATT TGGTGAAACA TTTGTAAGGG 4392

TAGGAGTTGA AAACTGCAGT TCCCAGTGCC ACGGAAGTGT GATTGGAGCC 4442

TGCAGATAAT GCCCAGCCAT CCTCCCATCC TGCACTTTAG CCAGCTGCAG 4492

GGCGGGCAAG GCAAGGAAAG CTGCTTCCCT GGAAGTGTAT CACTTTCTCC 4542

GGCAGCTGGG AAGTCTAGAA CCAGCCAGAC TGGGTTAAGG GAGCTGCTCA 4592

AGCAATAGCA GAGGTTTCAC CCGGCAGGAT GACACAGACC ACTTCCCAGG 4642

GAGCACGGGC ATGCCTTGGA ATATTGCCAA GCTTCCAGCT GCCTCTTCTC 4692

CTAAAGCATT CCTAGGAATA TTTTCCCCGC CAATGCTGGG CGTACACCCT 4742

AGCCAACGGG ACAAATCCTA GAGGGTATAA AATCATCTCT GCTCAGATAA 4792

TCATGACTTA GCAAGAATAA GGGCAAAAAA TCCTGTTGGC TTAACGTCAC 4842

TGTTCCACCC GGTGTAATAT CTCTCATGAC AGTGACACCA AGGGAAGTTG 4892

ACTAAGTCAC ATGTAAATTA GGAGTGTTTT AAAGAATGCC ATAGATGTTG 4942

FIGURE 1I

```
ATTCTTAACT GCTACAGATA ACCTGTAATT GAGCAGATTT AAAATTCAGG      4992

CATACTTTTC CATTTATCCA AGTGCTTTCA TTTTTCCAGA TGGCTTCAGA      5042

AGTAGGCTCG TGGGCAGGGC GCAGACCTGA TCTTTATAGG GTTGACATAG      5092

AAAGCAGTAG TTGTGGGTGA AAGGGCAGGT TGTCTTCAAA CTCTGTGAGG      5142

TAGAATCCTT TGTCTATACC TCCATGAACA TTGACTCGTG TGTTCAGAGC      5192

CTTTGGCCTC TCTGTGGAGT CTGGCTCTCT GGCTCCTGTG CATTCTTTGA      5242

ATAGTCACTC GTAAAACTG TCAGTGCTTG AAACTGTTTC CTTTACTCAT       5292

GTTGAAGGGA CTTTGTTGGC TTTTAGAGTG TTGGTCATGA CTCCAAGAGC      5342

AGAGCAGGGA AGAGCCCAAG CATAGACTTG GTGCCGTGGT GATGGCTGCA      5392

GTCCAGTTTT GTGATGCTGC TTTTACGTGT CCCTCGATAA CAGTCAGCTA      5442

GACACACTCA GGAGGACTAC TGAGGCTCTG CGACCTTCAG GAGCTGAGCC      5492

TGCCTCTCTC CTTTAGATGA CAGACCTTCA TCTGGGAACG TGCTGAGCCA      5542

GCACCCTCAG ATGATTTCCC TCCAAACTGC TGACTAGGTC ATCCTCTGTC      5592

TGGTAGAGAC ATTCACATCT TTGCTTTTAT TCTATGCTCT CTGTACTTTT      5642

GACCAAAAAT TGACCAAAGT AAGAAAATGC AAGTTCTAAA AATAGACTAA      5692

GGATGCCTTT GCAGAACACC AAAGCATCCC AAGGAACTGG TAGGGAAGTG      5742

GCGCCTGTCT CCTGGAGTGG AAGAGGCCTG CTCCCTGCTC TGGGTCTGCT      5792

GGGGGCACAG TAAATCAGTC TTGGCACCCA CATCCAGGGC AGAGAGGTCT      5842

GTGGTTCTCA GCATCAGAAG GCAGCGCAGC CCCTCTCCTC TTCAGGCTAC      5892

AGGGTTGTCA CCTGCTGAGT CCTCAGGTTG TTTGGCCTCT CTGGTCCATC      5942

TTGGGCATTA GGTTCTCCAG CAGAGCTCTG GCCAGCTGCC TCTTCTTTAA      5992

CTGGGAACAC AGGCTCTCAC AAGATCAGAA CCCCCACTCA CCCCCAAGAT      6042

CTTATCTAGC AAGCCTGTAG TATTCAGTTT CTGTTGTAGG AAGAGAGCGA      6092

GGCATCCCTG AATTCCACGC ATCTGCTGGA AACGAGCCGT GTCAGATCGC      6142
```

FIGURE 1J

| | | | | | |
|---|---|---|---|---|---|
| ACATCCCTGC | GCCCCCATGC | CCCTCTGAGT | CACACAGGAC | AGAGGAGGCA | 6192 |
| GAGCTTCTGC | CCACTGTTAT | CTTCACTTTC | TTTGTCCAGT | CTTTTGTTTT | 6242 |
| TAATAAGCAG | TGACCCTCCC | TACTCTTCTT | TTTAATGATT | TTTGTAGTTG | 6292 |
| ATTTGTCTGA | ACTGTGGCTA | CTGTGCATTC | CTTGAATAAT | CACTTGTAAA | 6342 |
| AATTGTCAGT | GCTTGAAGCT | GTTTCCTTTA | CTCACATTGA | AGGGACTTCG | 6392 |
| TTGGTTTTTT | GGAGTCTTGG | TTGTGACTCC | AAGAGCAGAG | TGAGGAAGAC | 6442 |
| CCCCAAGCAT | AGACTCGGGT | ACTGTGATGA | TGGCTGCAGT | CCAGTTTTAT | 6492 |
| GATTCTGCTT | TTATGTGTCC | CTTGATAACA | GTGACTTAAC | AATATACATT | 6542 |
| CCTCATAAAT | AAAAAAAAAA | CAAGAATCTG | AAAAAAAAAA | AAAAAAAAAA | 6592 |
| AAAAAAAAAA | AAAAAAAAAA | AAAAAAAAAA | AAAAAAAAAA | AAAAAAAAAA | 6642 |
| AAAAAAAAAA | AAAAAAAAAA | AAAAAAAA | | | 6671 | pVLDRADA140 pVLDRADA Δ

FIGURE 6

| | | | | SEQ ID NO |
|---|---|---|---|---|
| DRADA-1 | KNPISGLL EYA | QFASQTCEFNMIEQSGPPHEPRFKFQVVIN | GREFPPAEAGSKKVAKQDAAMKAMTILLEEA | 3 |
| DRADA-2 | KSPVTTLL ECM | HKLGNSCEFRLLSKEGPAHEPKFQYCVAV | GAQTFPSVSAPSKKVAKQMAAEEAMKALHGEA | 4 |
| DRADA-3 | TNPVGGLL EYA | RSHGFAAEFKLVDQSGPPHEPKFVYQAKV | GGRWFPAVCAHSKKQGKQEAADAALRVLIGEN | 5 |
| P68kinase-1 | AGFFMEELNTY | RQKQGVVLKYQELPNSGPPHDRRFTFQVLID | GREFPEGEGRSKKEAKNAAAKLAVEILNKEK | 6 |
| P68kinase-2 | GNYI GLINRIA | QKKRLTVNYE QCASGVHGPEGFEYKCKM | GQKEYSIGTGSTKQEAKQLAAKLAYLQILSEE | 7 |
| TIKkinase-1 | GFYMDK LNKY | RQMHGVAITYKELSTBGPPHDRRFTFQVLID | EKEFGEAKGRSKTEARNAAAKLAVDILDNEN | 8 |
| TIKkinase-2 | VGNYIGLVNSFA | QKKKLSVLIE QCEPNSELPQRFICKCKI | GQTMYGTGSGVTKQEAKQLAAKEAYQKLLKSP | 9 |
| HuTRBP-1 | KTPIS LLQEYG | TRIGKTPVYDLLKAEGQAHQPNFTFRVTV | GDTSCTGQGPSKKAAHKAAEVALKELKGGS | 10 |
| HuTRBP-2 | CNPV GALQELVVQKGWRLPEYTVTQESGPAHRKEFTMTCRV | ERFIEIGSGTSKKLLAKRNAAAKMLLRVHTVP | 11 |
| HuTRBP-3 | GPACCRVLSELS | EEQAFHVSYLDIEELSLSGLCQCLVELSTQ | PATVCHGSATTREAARGEAARRALQYLKIMA | 12 |
| X1TRBP-1 | ETPIQ LLHEFG | TKTGNHPVYTLEKAEGQAHNPSFTFRLVI | GDITSLGEPSKKTPKQKAAEFALNILRGDT | 13 |
| X1TRBP-2 | ENPV GSLQELAVQKGWRLPEYTVAQESGPPHKREFTITCRV | ETFVETGSGTSKQVAKRVAAEKLLTKFKTIS | 14 |
| X1TRBP-3 | TDYV KMLKDVA | EELDFNLTYLDIDELSVNGQYQCLAELSTN | PITVCHGTGISCGNAHNDAAHNALQYLKIMC | 15 |
| Staufen-1 | KTPM CLVNELARYNKITHQ YRLTEERGPAHCKTFTVTLML | GDEEYSADFKIKKAQHLAASKAIEETMYKH | 16 |
| Staufen-2 | KFPSRFALPPPLGAHVHHGPNGPFP | SVPTPPSKIT LFV | GKQKFVGIGRTLQQAKHDAAARALQVLKTQA | 17 |
| Staufen-3 | KSPIS QVHEIG | IKRNMTVHFKVLREEGPAHMKNFITACIV | GSIVTEGEGNGKKVSKKRAAEKMLVELQKLP | 18 |
| Staufen-4 | DNPITKLIQ LQQTRKEKEPIFELIAKNGNETARRREFVMEVSASGSTARGTGNSKKLAKRNAAQ ALFELLEAV | | | 19 |
| Staufen-5 | HMKE QLL YLS KLLDFEVNFSDY PKGNHNEFLTIVTLSTH PPQICHGVGKSSEESQNDAASNALKILSKLG | | | 20 |
| KHPVSALM EICNKRRWQPPEFLLVHDSGPDHRKHFLFRVLINGSAYQPSFASPNKKEAKATAATVVLQAMGLVP | | | | 21 |
| E3L | ANPVT VINEYC QITRRDWSFRI ESVGPSNSPTFYACVDID GRVFDKADGKSKRDAKNNAAKLAVDKLLGYV | | | 22 |
| Ns34 | PDPLI RLNDCKTKYGIDIICRF | YIVLDNDGSIIHMCYMRTGSAEAVAKGRSKKEAKRIAAKDILDQIGL* | | 23 |
| Pacl | DKLAKSKLFHKY | STLGHIEYRWVDGAG GSAEGYVIACIFN | GKEVARAWGANQKDAGSRAAMQALEVLAKDY | 24 |
| RNase III | KDPKT RLQEYLQGRHLPLPTYLVVQVRGEAHDQEFTIHCQVSGLSEPVVGTGSSRRKAEQAAAEQALKKLELE* | | | 25 |
| Huson-a | KNPV GLLNEYA QK G PEY LL ESGPAHDPKFTF V V GGREF GSG SKKEAKQ AAE AL IL E D | | | 26 |
| Consensus | I AMIQDFG R A | F VV D G EKRIY L I | AK Y ATA TRRD RN D V VI D | |
| | M VV L | II R L M M | K M M | |
| | L M I | M V C L | R I V | |
| | V | | | |

α-helix

RNA EDITING ENZYME AND METHODS OF USE THEREOF

CROSS-REFERENCE TO RELATED APPLICATION

This is a continuation-in-part of U.S. patent application Ser. No. 08/197,794, filed Feb. 17, 1994, now abandoned.

This invention was funded by Grant No. GM 40536, CA 09171, and CA 10815 from the Department of Health and Human Services. The U.S. Government has certain rights in this invention.

FIELD OF THE INVENTION

This invention relates generally to the production of proteins via genetic engineering techniques, and more specifically relates to the cloning and use of a novel RNA editing enzyme.

BACKGROUND OF THE INVENTION

The amino acid sequence of a protein is usually encoded directly by the sequence of nucleotides in a gene. In some cases, however, the correct protein sequence does not correspond exactly to the sequence encoded in the DNA. Instead, the DNA sequence must be edited to produce the functional protein. The editing of sequence information frequently occurs at the level of the messenger RNA (mRNA).

An activity characteristic of an adenosine deaminase enzyme specific for double-stranded RNA (dsRNA) has been previously functionally detected in many different invertebrates and vertebrates [Bass and Weintraub, Cell, 55:1089 (1988); Wagner et al, Proc. Natl. Acad. Sci., USA, 86.:2647 (1989); Rebagliati and Melton, Cell, 48:599 (1987); Bass and Weintraub, Cell, 8:607 (1987); Seiky and Iatrou, J. Mol. Biol., 218:517 (1991)] and also in most mammalian tissues and cell lines [Wagner and Nishikura, Mol. Cell Biol., 8:770 (1988); Wagner et al., Mol. Cell Biol., 10:5586 (1990)]. This enzymatic activity converts multiple adenosine (A) residues to inosines (I) by hydrolyric deamination [A. G. Polson et al, Biochem., 30:11507 (1991)]in both inter- and intra-molecular dsRNAs [Nishikura et al, EMBO J., 10:3523 (1991)], creating I-U mismatched base pairs in dsRNAs. The accumulation of extensive mismatched I-U base pairs in the dsRNA causes unwinding of the RNA double helix.

DRADA requires a double-helix structure for its substrate recognition but lacks strict sequence specificity [Bass and Weintraub, (1988); Nishikura et al., (1991); Wagner et al., (1989), all cited above].

DRADA is the first and so far, the only, RNA-unwinding activity that results in an accompanying base modification on the substrate RNA. This dsRNA unwinding/modifying activity further differs from other dsRNA unwinding activities or RNA helicases in that it seems to bind specifically to dsRNA.

DRADA is anticipated to be responsible for RNA editing of glutamate-gated ion-channel gene transcripts in mammalian brains. The A to I changes introduced in mRNA by this enzymatic activity, called DRADA, are revealed by A to G changes in its cDNA.

Several examples of in vivo interaction of this enzymatic activity with cellular as well as viral gene transcripts have been reported. For instance, maternal fibroblast growth factor gene and also its antisense transcripts seem to be extensively modified by DRADA in Xenopus oocytes undergoing meiosis [Kimelman and Kirschher, Cell, 59:687 (1989)]. The enzyme is responsible for genesis of defective measles virus with biased hypermutation, which results in lethal human CNS diseases, measles inclusion body encephalitis [Cattaneo et al., Virol., 55:255 (1988); Bass et al., Cell, 56:331 (1989)]. Furthermore, an adenosine located in a short stem structure of HIV TAR was reported to be modified to inosine by DRADA in a tat dependent manner [Sharmeen et al., Proc. Natl. Acad. Sci., USA, 88:8096 (1991)].

Because the enzyme introduces changes in the sequence of its substrate RNA, DRADA is anticipated to be involved in the RNA editing process [see, Kim and Nishikura, in RNA Editing, R. Benne, Ed. (Simon and Schuster International, Chichester, England (1993), pp. 179–192]. Three cases of RNA editing of glutamate-gated ion channel subunits which are responsible for the fast excitation of neurons in mammalian brain that always result in conversion of an A in the gene to a G in the cDNA have been reported [Sommer et al., Cell, 67:11 (1991); Verdoorn et al., Science, 252:1715 (1991); Köhler et al., Neuron, 10:491 (1993)]. This RNA editing process replaces the gene encoding glutamine (C AG) with an arginine (C$\underline{G}$G in subtype GluR-B,-5, -6), isoleucine (A$\underline{U}$U) with valine ($\underline{G}$UU), or tyrosine (UA$\underline{C}$) with cysteine (UG$\underline{C}$ in subtype GluR-6) within the transmembrane domains. These amino acid conversions have a large functional significance since the presence of the amino acid residue introduced by RNA editing in the transmembrane domain has been shown to be a determining factor in the channel behavior.

DRADA is thus implicated in conditions or disorders characterized by the malfunction or deficient functioning of neuronal transmission in mammalian brain, e.g., in disorders such as stroke, Huntingdon's disease, Alzheimers disease and other such neurological conditions.

There is a need in the art for the isolation and recombinant production of the protein which produces the enzymatic activity described for DRADA, to enable its use in genetic engineering, recombinant production of useful proteins and drug development and screening.

SUMMARY OF THE INVENTION

In one aspect, the invention provides novel, isolated polynucleotide sequences encoding human DRADA proteins. The polynucleotide sequences encoding these proteins are illustrated in FIG. 1 [SEQ ID NO:1]. Fragments of these sequences are also embodied by this invention. These polynucleotide sequences or fragments thereof may also be optionally associated with conventionally used labels for diagnostic or research use.

In another aspect, the present invention provides human DRADA proteins characterized by having RNA editing activity. These proteins are isolated from other cellular materials with which they are naturally associated, and have biological activities associated with an RNA editing function. The DRADA proteins, schematically illustrated in FIGS. 2A through 2C, are designated herein as a 140 kD protein [amino acid 1–1226 of SEQ ID NO: 2], an approximately 93 kD protein [aa 404–1226 of SEQ ID NO: 2], and an approximately 88 kD protein [aa 440–1226 of SEQ ID NO: 2]. An approximately 83 kD protein has also been identified on polyacrylamide gel and biochemically purified. Advantageously, one or more of these proteins is capable of being produced recombinantly.

In still other aspects, the invention provides an expression vector which contains at least a polynucleotide sequence described above, a host cell transformed with such an expression vector and methods of using these vectors and host cells in the recombinant production of DRADA proteins.

In yet a further aspect, the invention provides a polyclonal or monoclonal antibody generated by use of one of these human DRADA proteins or fragments thereof as an immunogen.

In another aspect, the invention provides a diagnostic reagent, such as a DNA probe, i.e., an oligonucleotide fragment derived from the polynucleotide sequence encoding one of the proteins of the invention or from the complementary strand. The reagents may be optionally associated with a detectable label.

In yet another aspect, the present invention provides a variety of methods for using an above described poly- or oligo-nucleotide sequence, a protein or an antibody, as an agent in a therapeutic composition for treating disorders characterized by deficient or abnormal DRADA.

In yet a further aspect, the invention provides methods for use of these novel above-identified proteins, sequences and antibodies in the development and screening of compounds useful as therapeutics for the treatment of neurological disorders and diseases which can affect the central nervous system, such as HIV or subacute sclerosing panencephalitis (SSPE).

In a further aspect, the present invention provides for compounds or drugs produced by use of the above methods.

Other aspects and advantages of the present invention are described further in the following detailed description of preferred embodiments of the present invention.

BRIEF DESCRIPTION OF THE DRAWINGS

FIGS. 1A–1J illustrates the nucleotide and amino acid sequences [SEQ ID NO: 1 and 2] of human DRADA proteins. A putative bipartite nuclear localization signal is boxed. The N-terminal sequences of the 93 kD and 88 kD proteins are indicated by the arrows. The three repeats of a dsRNA binding motif (DRBM) are underlined.

FIG. 6 illustrates a comparison between the three DRBM of human DRADA, indicated as DRADA-1 [SEQ ID NO: 3], DRADA-2 [SEQ ID NO: 4] and DRADA-3 [SEQ ID NO: 5] and by underlining in FIG. 1, and the DRBM of other dsRNA binding proteins obtained from Genbank and EMBL databases, including P68kinase-1 [SEQ ID NO: 6], P68kinase-2 [SEQ ID NO: 7], TIKkinase-1 [SEQ ID NO: 8], TIKkinase-2 [SEQ ID NO: 9], HuTRBP-1 [SEQ ID NO: 10], HuTRBP-2 [SEQ ID NO: 11], HuTRBP-3 [SEQ ID NO: 12], X1TRBP-1 [SEQ ID NO: 13], X1TRBP-2 [SEQ ID NO: 14], X1TRBP-3 [SEQ ID NO: 15], Staufen-1 [SEQ ID NO:16], Staufen-2 [SEQ ID NO: 17], Staufen-3 [SEQ ID NO: 18], Staufen-4 [SEQ ID NO: 19], Staufen-5 [SEQ ID NO: 20], Huson-a [SEQ ID NO: 21], E3L [SEQ ID NO: 22], Ns34 [SEQ ID NO: 23], Pac1 [SEQ ID NO: 24], RNase III [SEQ ID NO: 25] and a Consensus sequence based on all of these sequences [SEQ ID NO: 26 ].

DETAILED DESCRIPTION OF THE INVENTION

The present invention provides isolated and characterized human DNA sequences encoding a double stranded RNA adenosine deaminase enzyme (DRADA), and fragments thereof. DRADA and its protein fragments are responsible for mRNA editing of generations of glutamate-gated ion channel subunits. The provision of the polynucleotide sequences of this invention permits DRADA proteins to be produced by expression of the sequence in recombinant host cells. Because they are produced by recombinant techniques, both the nucleotide sequences and resulting expressed proteins are free from contamination with other sequences, cellular materials or protein materials with which the nucleotide and protein sequences occur in nature.

I. The DRADA Proteins

The DRADA protein is characterized by an approximately 1226 amino acid protein sequence and an apparent molecular weight of approximately 140 kD [SEQ ID NO:2] (See, FIG. 1). Included in this invention are fragments of the DRADA protein. Preferably, the 140 kD DRADA and these fragments are characterized by sharing the dsRNA deaminase activity. The DRADA fragments of this invention are biologically active and have similar biological activity to full-length human DRADA. Particularly desirable are the following fragments which have been found to be N-terminal truncated versions of DRADA: a DRADA protein spanning amino acids 404 to 1226 of SEQ ID NO: 2 and having an apparent molecular weight of 93 kD; and a DRADA protein spanning amino acids 440 to 1226 of SEQ ID NO: 2 and having an apparent molecular weight of 88 kD. A DRADA protein having an apparent molecular weight of 83 kD on the polyacrylamide gel and which was biochemically purified has also been identified.

Also included in the invention are analogs, or modified versions, of the DRADA proteins provided herein. Typically, such analogs differ by only 1, 2, 3 or 4 codon changes. Examples include polypeptides with minor amino acid variations from the illustrated amino acid sequences of DRADA (FIG. 1; SEQ ID NO:2); in particular, conservative amino acid replacements. Conservative replacements are those that take place within a family of amino acids that are related in their side chains and chemical properties.

Additionally, the DRADA proteins [SEQ ID NO:2] of the invention may be modified, for example, to improve production thereof, to enhance protein stability or other characteristics, e.g. binding activity or bioavailability, to enhance its use for screening competitive compounds or to confer some other desired property upon the protein. For example, the catalytic domain of DRADA located in the carboxyl terminus at about amino acid 797 to 1226 of SEQ ID NO: 2 may be separately excised to obtain a DRADA protein more useful for screening compounds. Alternatively, a DRADA protein of the invention may be truncated or modified to remove the putative nuclear localization signal indicated in FIG. 1 at amino acids 169–170 and 181–185 of SEQ ID NO:2.

Figure 3:
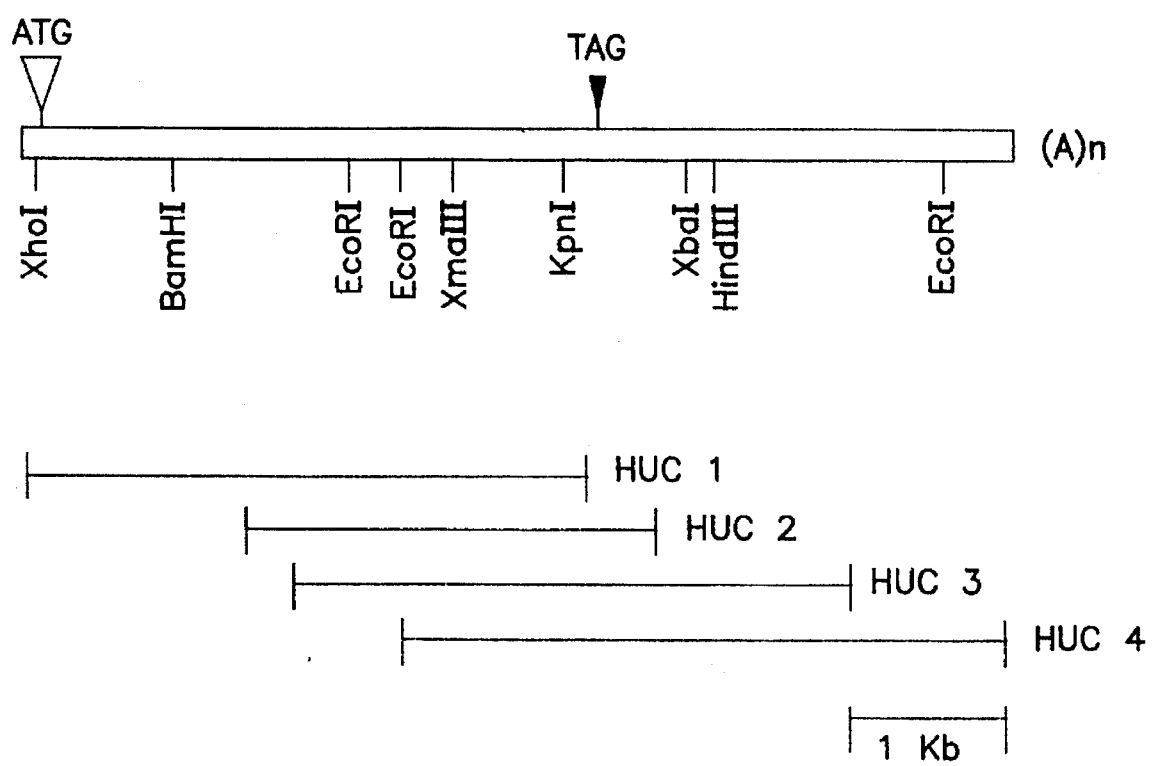
FIG. 3 illustrates the restriction map of the ORF of the human DRADA protein with indicated endonuclease enzyme restriction sites and the start (ATG) and stop (TAG) translation codons, and the overlapping human cDNA clones, HUC 1 through 4.

Similarly, if desired, the dsRNA binding sites indicated in FIG. 3 by underlining at amino acids 502–573 of SEQ ID NO:2 (DRBM1), at amino acids 703–684 of SEQ ID NO:2 (DRMB2), and at amino acids 725–796 of SEQ ID NO:2 (DRBM3) may be modified by deletion or modification of one or more amino acid residues to provide alternate targets for the screening of compounds capable of binding thereto and inhibiting the function of DRADA. Similarly, the phosphorylation sites on DRADA, which may be identified by their known motifs on a variety of conventional computer programs, may be excised or altered for use in screening for binding or inactivating compounds.

Sequence analysis indicates that DRADA is a new member of the double stranded RNA (dsRNA) binding protein family. The adenosine-to-inosine conversion activity of the DRADA protein encoded by the cloned cDNA was confirmed by recombinant expression in insect cells. Use of the cloned DNA as a molecular probe documented sequence conservation across mammals, and detected a single transcript of 7 kb in RNA of all human tissues analyzed. The deduced primary structure of human DRADA revealed a bipartite nuclear localization signal, three repeats of dsRNA binding motifs, and the presence of sequences conserved in the catalytic center of deaminases, including a cytidine deaminase involved in the RNA editing of apolipoprotein B. It is anticipated that DRADA is involved in other gene systems, and that target genes exist, in addition to the glutamate-gated ion-channel subtype GluR-B transcripts, in different tissues. DRADA may be used in an editing capacity for these additional targets.

The DRADA proteins of this invention are useful in therapeutic compositions for the treatment of glutamate-gated ion-channel defects or malfunctions, which can result in neurological disorders such as seizures and strokes. Specifically, the use of DRADA to achieve sequence specific editing of the glutamate-gated ion channel gene transcripts has been described by M. Higuchi et al, *Cell*, 75:1361–1370 (1993). In one example, the editing replaces the gene-encoded glutamine (Q encoded by C<u>A</u>G) with an arginine ( <u>R</u> encoded by C<u>G</u>G). For this Q/R site editing in GluR-B, formation of a 17 bp dsRNA structure between exon and intron sequences is a prerequisite [Higuchi et al, cited above]. In addition for efficient modification, the editing further requires a 45 nucleotide inverted repeat structure. Additional adenosines in the intron as well as a glutamine codon (C<u>A</u>A) adjacent to the Q/R site were found to be modified also.

These proteins may also be useful in diagnostic applications, as well as for generation of other therapeutic and diagnostic reagents, such as anti-DRADA antibodies. In common with other proteins generally, these newly-identified DRADA proteins may also serve as molecular weight markers or in other aspects in screening assays or as research tools. More desirably, the DRADA proteins are also useful for the screening and development of chemical therapeutic agents useful for preventing or enhancing the action of DRADA and thereby correcting the ion channel expression.

II. DRADA Polynucleotide Sequences

Figure 2A:
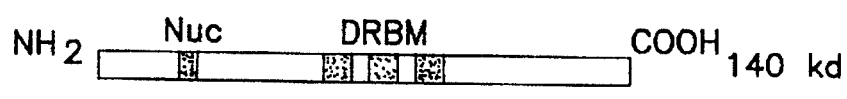
FIG. 2A illustrates a bar graph which represents the open reading frame (ORF) for a 140 kD form of human DRADA, with the putative nuclear localization signal indicated by a black box (NUC), and the dsRNA binding motifs (DRBM) indicated by hatching.

The approximately 6671 bp polynucleotide sequence of the human DRADA gene is provided in FIG. 1 [SEQ ID NO:1]. These sequences have been deposited in the GenBank data base (Accession No. U10439). It encodes the approximately 1226 amino acid protein sequence for the full-length DRADA protein, and portions of this polynucleotide sequence encode the N-terminal deletion proteins of DRADA having apparent molecular weights of 93, 88 and 83 kD. The nucleotide sequence of DRADA contains a short 5' untranslated region (154 bp), and a long 3' untranslated region (2840 bp), including a polyadenylate tract of 99 bases. It is currently not known whether this DNA contains the 5' end or cap site of DRADA mRNA. As shown in FIG. 2A, DRADA contains a single ORF (thin open box).

In addition to the polynucleotide fragments encoding the truncated DRADA protein sequences mentioned above, other fragments of these sequences may prove useful for a variety of uses. Desirably, these fragments are at least about 15 nucleotides in length and encode a desired amino acid sequence, e.g. an epitope, a therapeutically useful peptide, or the like. These nucleotide sequences of the invention may be isolated as by conventional uses of polymerase chain reaction or cloning techniques such as those described in obtaining the bovine and human sequences in Examples 1 and 3, described below. Alternatively, these sequences may be constructed using conventional genetic engineering or chemical synthesis techniques.

According to the invention, the nucleic acid sequence [SEQ ID NO: 1] coding for the encoded DRADA proteins [SEQ ID NO: 2] described above and provided in FIG. 1, may be modified. Utilizing the sequence data in these figures, it is within the skill of the art to obtain other polynucleotide sequences encoding the proteins of the invention. Such modifications at the nucleic acid level include, for example, modifications to the nucleotide sequences which are silent or which change the amino acids, e.g. to improve expression or secretion.

In still another alternative, the polynucleotide sequences may be modified by adding readily assayable tags to facilitate quantitation, where desirable. Nucleotides may be substituted, inserted, or deleted by known techniques, including, for example, in vitro mutagenesis and primer repair. Also included are allelic variations, caused by the natural degeneracy of the genetic code.

In addition to isolated nucleic acid sequences [SEQ ID NO: 1] encoding the DRADA protein [SEQ ID NO: 2] described herein, this invention also encompasses other nucleic acid sequences, including those complementary to the illustrated DNA sequences, such as antisense sequences. Useful DNA sequences also include those sequences which hybridize under high or moderately high stringency conditions [see, T. Maniatis et al, *Molecular Cloning (A Laboratory Manual)*, Cold Spring Harbor Laboratory (1982), pages 387 to 389] to the DNA sequences illustrated in FIG. 1. An example of a highly stringent hybridization condition is hybridization at 4×SSC at 65° C., followed by a washing in 0.1×SSC at 65° C. for an hour. Alternatively, an exemplary highly stringent hybridization condition is in 50% formamide, 4×SSC at 42° C. Other, moderately high stringency conditions may also prove useful, e.g. hybridization in 4×SSC at 55° C., followed by washing in 0.1×SSC at 37° C. for an hour. Alternatively, an exemplary moderately high stringency hybridization condition is in 50% formamide, 4×SSC at 30° C.

The nucleic acid sequences encoding these proteins are themselves useful for a variety of diagnostic and therapeutic uses. Advantageously, the nucleic acid sequences are useful in the development of diagnostic probes and antisense probes for use in the detection and diagnosis of genetic disorders characterized by deficient or aberrant DRADA enzymes and glutamate-gated ion-channel communication. Such disorders are neurological and can include stroke, Huntingdon's chorea and the like. Oligonucleotide probes may be useful in such standard diagnostic techniques as Southern blotting and polymerase chain reaction.

The nucleic acid sequences of this invention are also useful in the production of human DRADA proteins. Once constructed, or isolated, as described in further detail in Example 1 below, these DNA sequences or suitable fragments are preferably employed to obtain proteins of this invention.

III. Recombinant Expression of DRADA

To produce recombinant DRADA proteins of this invention, the DNA sequences of the invention are inserted into a suitable expression system. Desirably, a recombinant molecule or vector is constructed in which the polynucleotide sequence encoding DRADA is operably linked to a heterologous expression control sequence permitting expression of the human DRADA protein. Numerous types of appropriate expression vectors and host cell systems are known in the art for mammalian (including human) expression, insect, e.g., baculovirus expression, yeast, fungal, and bacterial expression, by standard molecular biology techniques.

The transformation of these vectors into appropriate host cells can result in expression of the selected DRADA proteins. Other appropriate expression vectors, of which numerous types are known in the art, can also be used for this purpose.

Suitable host cells or cell lines for transfection by this method include insect cells, such as *Spodoptera frugipedera* (Sf9) cells. Methods for the construction and transformation of such host cells are well-known. [See, e.g. Miller et al, *Genetic Engineering*, 8:277–298 (Plenum Press 1986) and references cited therein].

Similarly, mammalian cells, such as Human 293 cells, Chinese hamster ovary cells (CHO), the monkey COS-1 cell line or murine 3T3 cells derived from Swiss, Balb-c or NIH mice may be used. Suitable mammalian host cells and methods for transformation, culture, amplification, screening, and product production and purification are known in the art. [See, e.g., Gething and Sambrook, *Nature*, 293:620–625 (1981), or alternatively, Kaufman et. al, *Mol. Cell. Biol.*, 5(7):1750–1759 (1985) or Howley et al, U.S. Pat. No. 4,419,446]. Another suitable mammalian cell line is the CV-1 cell line.

Similarly useful as host cells suitable for the present invention are bacterial cells. For example, the various strains of *E. coli* (e.g., HB101, MC1061, and strains used in the following examples) are well-known as host cells in the field of biotechnology. Various strains of *B. subtilis*, Pseudomonas, other bacilli and the like may also be employed in this method.

Many strains of yeast cells known to those skilled in the art are also available as host cells for expression of the polypeptides of the present invention. Other fungal cells may also be employed as expression systems.

Thus, the present invention provides a method for producing a recombinant human DRADA protein which involves transforming a host cell with at least one expression vector containing a recombinant polynucleotide encoding a human DRADA protein under the control of a transcriptional regulatory sequence, e.g. by conventional means such as transfection or electoporations. The transformed host cell is then cultured under suitable conditions that allow expression of the human DRADA protein. The expressed protein is then recovered, isolated, and purified from the culture medium (or from the cell, if expressed intracellularly) by appropriate means known to one of skill in the art.

For example, the proteins may be isolated following cell lysis in soluble form, or extracted in guanidine chloride. If desired, the DRADA proteins of the invention may be produced as a fusion protein. For example, it may be desirable to produce such DRADA fusion proteins, to enhance expression of the protein in a selected host cell, or to improve purification. Suitable fusion partners for the DRADA proteins of the invention are well known to those of skill in the art and include, among others, β-galactosidase and poly-histidine.

IV. Production of Anti-DRADA Antibodies

The DRADA proteins of this invention are also useful as antigens for the development of specific antibodies, both polyclonal and monoclonal, to DRADA or various portions of the DRADA proteins, such as the DRBM or catalytic regions. Antibodies may also be developed to modified versions or analogs of DRADA. These antibodies may be produced by conventional methods, including the Kohler and Milstein hybridoma technique, recombinant techniques, such as described by Huse et al, *Science*, 246:1275–1281 (1988), or any other modifications thereof known to the art.

V. Diagnostic Reagents

The proteins, antibodies, and polynucleotide sequences (including anti-sense polynucleotide sequences) of this invention may be useful as diagnostic reagents for diagnosing certain neurological or central nervous system disorders, e.g., Huntingdon's disease, SSPE, measles inclusion body encephalitis, strokes and other conditions, which are found to be associated with abnormal or deficient expression of DRADA. These reagents may optionally be labelled using diagnostic labels, such as radioactive labels, colorimetric enzyme label systems and the like conventionally used in diagnostic or therapeutic methods. The reagents may measure abnormal DRADA levels or detect mutant DRADA enzymes in selected mammalian tissue in conventional diagnostic assays, e.g., Southern blotting, Northern and Western blotting, polymerase chain reaction and the like. For example, as diagnostic agents the polynucleotide sequences may be employed to detect or quantitate normal or mutant DRADA mRNA or detect mutations in target gene RNA in a patient sample. The selection of the appropriate assay format and label system is within the skill of the art and may readily be chosen without requiring additional explanation by resort to the wealth of art in the diagnostic area.

Thus the present invention provides methods for the use of these protein, antibody or polynucleotide reagents in the diagnosis of disorders characterized by neurological symptoms, such as the malfunction of glutamate-gated ion-channels or detection of genetic diseases. The methods involve contacting a selected mammalian tissue, e.g., cerebrospinal fluids, or other cells with the selected reagent, protein, antibody or DNA sequence, and measuring or detecting the amount of DRADA present in the tissue in a selected assay format based on the binding or hybridization or the reagent to the tissue.

VII. Therapeutic Reagents

Alternatively, the DRADA proteins or nucleotide sequences may be useful as therapeutic reagents for delivery of biologically active DRADA to mammalian tissue. As one example, the recombinant protein may itself be administered by appropriate routes in a pharmaceutical composition to correct the malfunctioning of glutamate-gated ion channels. Alternatively, a desired DRADA nucleic acid sequence of the invention may be incorporated into a suitable vector or other delivery system. Suitable delivery systems are well known to those of skill in the art. Vectors containing such sequences may be administered, thus, treating deficiencies of DRADA via in vivo expression of the proteins of the invention. Such delivery systems enable the desired DRADA gene to be incorporated into the target cell and to be translated by the cell.

Still another method involves the use of the DRADA polynucleotide sequences for gene therapy. In the method, the DRADA sequences are introduced into a suitable vector for delivery to a cell containing a defect in the DRADA gene. By conventional genetic engineering techniques, the DRADA gene sequence may be introduced to mutate the existing gene by recombination or in addition to the inactive gene to replace it.

According to the above methods, a recombinant DRADA protein of the invention can be provided to a cell, particularly a cell in an individual having a condition characterized by a deficiency in DRADA. Such therapeutic uses are anticipated for disorders characterized by neurological symptoms and caused at least in part by the lack of active DRADA or the presence of abnormal or inactive DRADA enzyme in mammalian tissue.

VIII. Drug Screening and Development

The proteins, antibodies and polynucleotide sequences of the present invention may also be used in the screening and development of chemical compounds or proteins which have utility as therapeutic drugs for the treatment of neurological disorders, such as those identified above.

As one example, a compound capable of binding to DRADA and either preventing or enhancing its biological activity may be a useful drug component for the treatment or prevention of neurological disorders characterized by defect in the ion channel expression, or diseases such as SSPE or measles inclusion body encephalitis. In the former case, the drug may work by correcting channel expression. In the latter case, the drug may work by preventing the DRADA enzyme from mutating the relatively harmless measles virus into its lethal form. Additionally, based on the similarities of the DRADA DRBM and sequences within the HIV TAR binding protein, HuTRBP, and other dsRNA proteins, a compound identified as binding to, and/or blocking the DRADA DRBM or catalytic domain, may be a useful drug component for the treatment of HIV [Sharmeen et al, cited above] or other disease agents which invade the mammalian cell via a similar sequence (See FIG. 6).

Presently, conventional assays and techniques exist for the screening and development of drugs capable of competitively binding to selected regions of DRADA, such as the DRBM or catalytic domains. These include the use of phage display system for expressing the DRADA proteins or portions thereof, e.g., DRBMs, and using a culture of transfected *E. coli* or other microorganism to produce the proteins for binding studies of potential binding compounds. See, for example, the techniques described in G. Cesarini, *FEBS Letters*, 307(1):66–70 (July 1992); H. Gram et al, *J. Immunol. Meth.*, 161:169–176 (1993); C. Summer et al, *Proc. Natl. Acad. Sci., USA*, 89:3756–3760 (May 1992), incorporated by reference herein.

Other conventional drug screening techniques may be employed using the proteins, antibodies or polynucleotide sequences of this invention. As one example, a method for identifying compounds which specifically bind to DRADA DNA sequences can include simply the steps of contacting a selected DRADA DNA fragment, e.g., a DRBM fragment of SEQ ID NO: 1, with a test compound to permit binding of the test compound to the DNA fragment; and determining the amount of test compound, if any, which is bound to the DNA fragment. Such a method may involve the incubation of the test compound and the DRBM DNA fragment immobilized on a solid support.

Another method of identifying compounds which specifically bind to DRADA DNA binding sequences can include the steps of contacting a DRADA DRBM DNA fragment immobilized on a solid support with both a test compound and the protein sequence which is the normal binding partner of the DRADA DRBM to permit binding of the normal binding partner protein to the DRADA DNA fragment; and determining the amount of the normal binding partner protein which is bound to the DNA fragment. The inhibition of binding of the normal protein by the test compound thereby indicates binding of the test compound to the DRADA DRBM DNA sequences.

Still other conventional methods of drug screening can involve employing a suitable computer program to determine compounds having similar or complementary chemical structures to that of the DRADA DRBM, and screening those compounds either for competitive binding to DRADA DRBM and/or using the base modification assay described below to detect enhanced or decreased DRADA activity in the presence of the selected compound.

Thus, through use of such methods, the present invention is anticipated to provide compounds capable of interacting with DRADA or portions thereof, and either enhancing or decreasing its biological activity, as desired. Such compounds are believed to be encompassed by this invention.

It should be understood that one of skill in the art may readily select the type of conventional screening method most desirable, as well as the reagent of this invention, e.g., the DRADA protein, nucleotide sequence, or fragment thereof or an antibody developed by use of such DRADA proteins.

The following examples which disclose the cloning and expression of human DRADA are for illustrative purposes only, and should not be construed as limiting this invention in any way.

EXAMPLE 1

Isolation of Bovine DRADA Protein

Using an assay for modified bases designed to detect inosine converted from adenosines described below and according to methods described by Wagner and Nishikura, (1988) and Wagner et al., (1989), both cited above, a DRADA homolog was isolated from bovine liver nuclear extracts as follows:

A. Preparation of Nuclear Extract

Nuclear extract was prepared from bovine liver by the method described by Dignam et al, *Nucleic Acids Res.*, 11:1475–1489 (1983) with the following modifications. All procedures were carried out at 4° C. Fresh bovine liver (1 Kg), obtained from a local slaughterhouse, was minced using a blender, and further homogenized by a motor-driven Potter-homogenizer in 3 times the packed cell volume of a buffer containing 10 mM Hepes (pH 7.6), 25 mM KCl, 0.15 mM spermine, 0.5 mM spermidine, 1 mM EDTA, 2M sucrose, and 10% glycerol. After centrifugation at 30,000 rpm in a Type 45 Ti Beckman rotor for 30 minutes, the nuclear pellet was suspended in a hypertonic buffer containing 0.02M Hepes (pH 7.9), 0.42M NaCl, 1.5 mM $MgCl_2$, 0.2 mM EDTA, 25% glycerol, 0.5 mM dithiothreitol (DTT), and 0.5 mM PMSF.

After two strokes in a glass dounce-homogenizer, the protein extract was cleared of debris by centrifugation at 30,000 rpm for 30 minutes. The activity was precipitated by adding solid $(NH_4)_2SO_4$ to 55% saturation (0.33 g/ml) and stirring for 1 hour at 4° C. After centrifugation at 35,000 rpm for 1 hour, the pellet was resuspended in a small volume (~1/10 volumes of initial cell pellets) of buffer A [0.02M Hepes (pH 7.5), 5 mM EDTA, 1 mM DTT, 17% glycerol, and 0.25 mM PMSF] containing 0.15M KCl, and dialyzed against three changes of 2 L of the same buffer to remove $(NH_4)_2SO_4$. The final nuclear extract was cleared by centrifugation at 30,000 rpm for 30 minutes and frozen in liquid nitrogen in aliquots. Typically, 1 Kg of liver yielded approximately 5 g of nuclear extract proteins.

B. ssDNA Agarose Column and First Cycle of Poly(I).Poly(C) Agarose Column

All column chromatography procedures were carried out at 4° C. Approximately 5 g of crude nuclear extract (after adjusting salt concentration to 0.35M KCl) was passed through 85 ml (2.6×16 cm) of ssDNA agarose column equilibrated with buffer A containing 0.35M KCl at a flow rate of 20 ml/hour. The enzyme did not bind to the ssDNA and was found in the flow-through fraction. The ssDNA column served to remove certain ssDNA binding proteins that would otherwise also bind to the dsRNA column.

The flow-through containing the activity, which was immediately loaded onto 50 ml (2.6×10 cm) of poly(I)-poly(C) dsRNA agarose column that has been equilibrated with buffer A containing 0.35M KCl. The poly(I)-poly(C) column was washed sequentially with 100 ml of buffer A containing 0.5M KCl and then 100 ml of buffer A with 1.0M KCl at a flow rate of 20 ml/hour. The enzyme bound to the poly(I).poly(C) duplexes very tightly under the conditions used, allowing other dsRNA binding proteins to be washed from the column with high salt buffer (up to 1.0M KCl).

The enzyme was eluted by raising the salt concentration of the buffer. The activity was eluted with 100 ml of buffer A containing 3.0M KCl and 0.2% Nonidet-P40 (NP40) at a flow rate of 10 ml/hour. NP40 (0.1–0.2%) was added to buffers in all of the subsequent steps of purification in order to prevent the loss of the dilute enzyme. Fractions of 10 ml each were collected and assayed for base modification activity of Example 2 to identify the active fractions. The 3.0M KCl fraction contained two major polypeptides with apparent molecular weights of 93 and 88 kD as judged by SDS-PAGE stained with silver.

C. Second Cycle of Poly(I).Poly(C) Agarose Column

To further purify the enzyme from minor contaminants, the 3.0M KCl fraction was rechromatographed through a second purification cycle on the poly(I).poly(C) column. Active fractions from the first cycle of poly(I).poly(C) agarose column were pooled, diluted to 0.35M KCl with buffer A containing 0.2% NP40, and passed through a second cycle of 50 ml poly(I).poly(C) agarose column. The column was washed and eluted as for the first poly(I).poly(C) column, except that all buffers contained 0.2% NP40. Active fractions purified by two cycles of dsRNA affinity column chromatography were then concentrated by DEAE CL-6B ion exchange column chromatography.

D. DEAE CL-6B Ion Exchange Column

The active fractions from the second poly(I).poly(C) agarose column were pooled and dialyzed against two changes of 2 L of buffer B [0.02M Hepes (pH 7.9), 5 mM EDTA, 1.0 mM DTT, 17% glycerol, and 0.25 mM PMSF] containing 0.05M KCl and 0.2% NP40 for 8 hours. The dialyzed fraction was passed through 1.0 ml (1.0×1.3 cm) DEAE CL-6B (Pharmacia), equilibrated with buffer B containing 0.05M KCl and 0.2% NP40 at a flow rate of 4 ml/hour. After washing the column with 4 ml of buffer B containing 0.05M KCl and 0.2% NP40, the activity was eluted with 10 ml of buffer A containing 3.0M KCl and 0.2% NP40. Active fractions were identified by base modification assay of Example 2.

The final purified fraction containing the 93 kD and 88 kD polypeptides was estimated to be enriched about 22,000-fold over the initial liver homogenate in DRADA activity with a yield of 0.16% and was fractionated by SDS-PAGE (7% gel), and visualized by silver staining. Molecular weight standards used were α2-macroglobulin (108 kD), β-galactosidase (116 kD), phosphorylase B (94 kD), bovine serum albumin (67 kD), pyruvate kinase (58 kD), fumarase (48.5 kD), lactic dehydrogenase (36.5 kD), and carbonic anhydrase (30 kD).

The gel revealed three major peptides with apparent molecular weights of 93, 88, and 83 kD. These three proteins behaved identically on a two-dimensional isoelectrofocusing gel and also produced nearly identical peptide cleavage patterns after digestion with trypsin.

EXAMPLE 2

DRADA Assay and Base Modification Assay

A. DRADA Assay

DRADA was assayed in vitro [Bass et al, *Cell*, 48:607–613 (1987); Wagner et al, *Mol. Cell. Biol.*, 8:770–777 (1988)]. Unless specified otherwise, the reaction was carried out in 100 µl reaction, which contained 10 fmol of α-[$^{32}$P]ATP-labeled c-myc dsRNA or human α-globin dsRNA [Wagner et al, cited above; Nishikura et al, *EMBO J.*, 10:3523–3532 (1991)], 0.05M Tris (pH 7.0), 0.2M NaCl, 5 mM EDTA, 1 mM DTT, and 20% glycerol, and various amounts of bovine liver nuclear extract proteins or 20 ng of purified DRADA proteins. After incubation for 1 hour at 37° C., the reaction products were deproteinized and then precipitated with ethanol, as described previously [Wagner et al, cited above; Wagner et al, *Proc. Natl. Acad. Sci. USA*, 86:2647–2651 (1989)]. The extracted RNAs were analyzed with the below-described base modification assay.

B. Base Modification Assay

The DRADA activity was followed by determining the amount of adenosine converted to inosine by a fixed volume of each fraction in an in vitro base modification assay as follows. After the DRADA reaction, the RNA samples, together with 10 µg of *Escherichia coli* tRNA, were digested with nuclease $P_1$ into 5'-mononucleotides. The digests were analyzed by one-dimensional thin layer chromatography (TLC). The solvent system used was 0.1M sodium phosphate (pH 6.8)/ammonium sulfate/1-propanol, 100:60:2 (v/w/v) as described in SilverKlang et al, *Methods Enzymol.*, 59:58–109 (1979). The radioactivity of the adenosine and inosine spots on TLC plates was quantified by the Phosphor Imaging System (Molecular Dynamics, Sunnyvale, Calif.).

Figure 5:
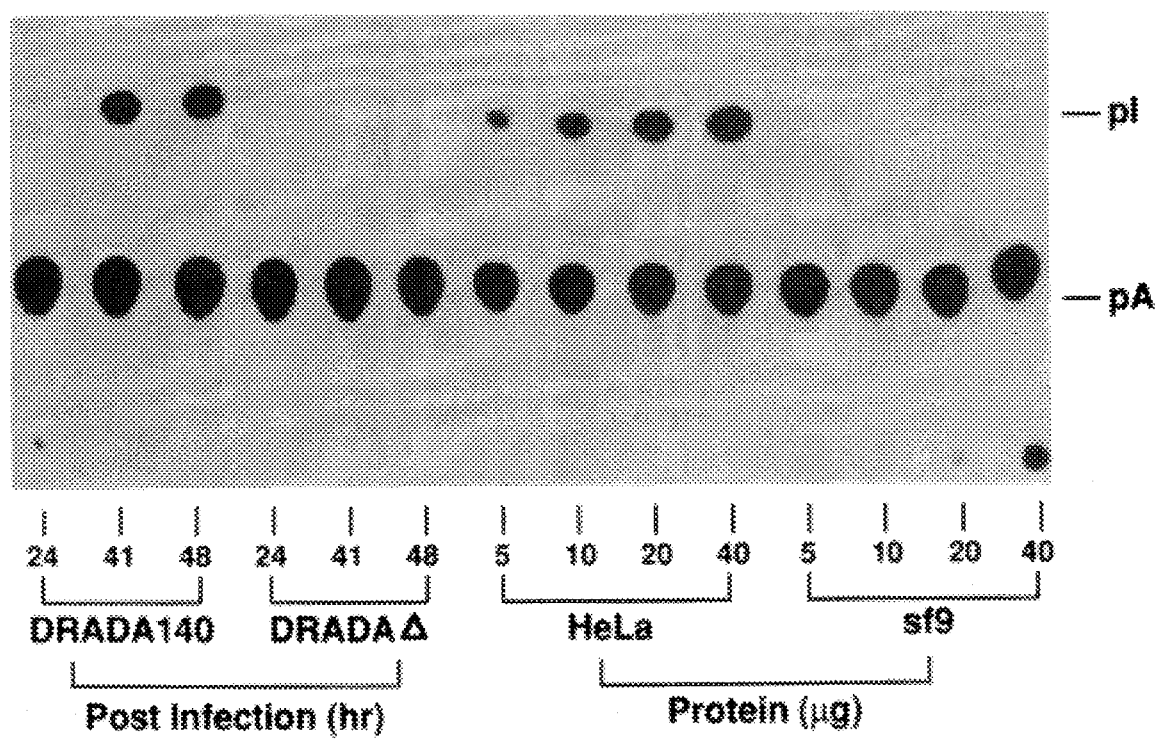
FIG. 5 shows the results of an assay for detection of modified bases illustrating inosine 5'-monophosphate (pI) and adenosine 5'-monophosphate (pA) for DRADA140 and DRADAdelta at 24, 41 and 48 hours post infection, and for crude extracts of Spodoptera frugipedera (Sf9) insect cells and HeLa mammalian cells using increasing amounts (1, 10, 20, and 40 μg) of protein.

The relative positions for inosine 5'-monophosphate (pI) and adenosine 5'-monophosphate (pA) are as indicated in FIG. 5. NE, nuclear extract; FT, flow through. Inosines converted from adenosines were estimated by quantitating the ratio of pI and pA spots on the TLC plates. See FIG. 5.

EXAMPLE 3

Obtaining Bovine Clones

Bovine cDNA clones coding for the $NH_2$-terminus of 93 and 88 kD proteins were obtained by the method of multiple oligo-primed PCR amplification of cDNA (Lee and Caskey, in *PCR Protocols: A Guide to Methods and Application*, M. A. Innis et al, Eds., (Academic Press, Inc., San Diego, Calif. 1990), pp. 47–53.

A. Reverse-Transcriptase Polymerase Chain Reaction

In brief, degenerate sets of oligonucleotides that represented the codons for NH$_2$-terminal peptide sequences were synthesized. For the 93 kD protein, the sense primer was SEQ ID NO: 27: 5'CCGGAATTCNGGNAAA/GGTNGA3', and the antisense primer was SEQ ID NO: 29: 5'CGGGATCCNGCT/CTCCTT/CTGGT/CTTNA, which correspond to amino acid residues SEQ ID NO: 28: PGKVE and SEQ ID NO: 30: AEQKL, respectively. For the 88 kD protein, the sense primer was SEQ ID NO: 31: 5'CGGAATTCAAA/GACNGGNTAC/TGTNGA3', and the antisense primer was SEQ ID NO: 33: 5,'CGGGATCCG/ ATCG/ATCNGGG/T/AATG/ATCG/ATC3', which correspond to residues SEQ ID NO: 32: KTGYVD and SEQ ID NO: 34: DDPIDD, respectively. Restriction sites for EcoRI for the sense primer and BamHI for the antisense primer were included at the 5' end and are underlined in the sequences above. In addition, internal probes representing the residues flanked by the sense and antisense primers were synthesized. The sequence of the internal probe for the 93 kD protein was SEQ ID NO: 35: 5'C/TTTG/CACG/CACG/ T/AGGCTCCTG3', and for the 88 kD protein was SEQ ID NO: 36: 5,'CGGGATCCAT/CTGNCCA/GTTC/TTCT/ GTT3'.

All possible degenerate codons were included for the sense and antisense primers. For the internal probes, only the codons preferred in bovine genomes were included.

The first-strand cDNA synthesis was carried out using total RNA prepared from the cultured bovine endothelial cell line, BFA-1C BPT [J. Grinspan et al, *J. Cell Physiol.*, 114:328–338 (1983)] and a GeneAmp® RNA PCR kit (Perkin Elmer Cetus) in a 20 μl reaction containing 10 mM Tris-Cl (pH 8.3), 5 mM MgCl$_2$, 50 mM KCl, 1 mM each dA/G/C/TTP, 1 unit RNase inhibitor, 400 ng antisense primer, 2.5 unit/μl reverse transcriptase and 1 μg total RNA at 42° C. for 1 hour. The reaction was terminated by incubating the tubes at 99° C. for 5 minutes.

B. Screening of the Recombinant Library

The PCR was done in a 100 μl reaction containing 10 mM Tris-Cl (pH 8.3), 50 mM KCl, 2 mM MgCl$_2$, 4 μM each of sense and antisense primers, 2.5 unit AmpliTaq DNA polymerase. Amplification was performed in a thermal cycler with 35 cycles of 95° C. for 30s, 48° C. for 1 min, 70° C. for 1 minute. A portion of the amplified product was analyzed by Southern hybridization at 42° C. in 6×SSC, 0.1% sodium pyrophosphate, 0.1% SDS, 0.1% Denhardt's, 50 mM Tris-Cl (pH 7.5), and 100 μg single-stranded DNA, using the internal probe labeled with [gamma-$^{32}$P] ATP [see Example 6].

The 75 bp cDNA that hybridized to the internal probe was purified from an agarose gel, digested with EcoRI and BamHI, and ligated with pBluescript KS+plasmid. Selected subclones were sequenced using the sense and antisense primers. Sets of nested deletion mutants of the cDNA clones were generated using exonuclease III and mungbean nuclease [Ansubel et al, *Current Protocols in Molecular Biology*, Current Protocols, New York, N.Y. (1993)]. The deleted clones were sequenced by either Sequenase (U.S. Biochemicals) or Taq Dye Deoxy Terminator Cycle Sequencing Kit, and analyzed by the 373A DNA Sequencing system (Applied Biosystems). The overlapping sequences of subclones were aligned and combined by the Fragment Assembly program of the University of Wisconsin Genetics Computer Group (GCG) sequence analysis software package, Version 7.0 [Devereux et al, cited above].

Two cDNA clones were chosen for subsequent experiments, and named BUC1 and BUC2, which coded for the NH$_2$-terminus of the bovine DRADA 93 kD and 88 kD proteins, respectively.

Amino acid sequence of the NH$_2$-terminus of both the bovine 93 and 88 kD proteins, which are not blocked by acylation, were determined by microsequencing.

EXAMPLE 4

Obtaining the Human DRADA cDNA

A recombinant cDNA library in the Lambda Zap®II vector was made from human natural killer (NK) cells isolated from human blood, which cells are known to contain a high level of DRADA activity. The library was screened by the method of Maniatis et al., cited above, using the BUC2 clone as a specific probe.

The purified positive lambda phage was converted to a pBluescript plasmid by the in vivo excision method described in Stratagene's manual. The resultant cDNA plasmid, HUC1, contained approximately 4-kb of insert DNA, which hybridized to both BUC1 and BUC2 by Southern blot analysis. The insert of HUC1 was then used to rescreen the original cDNA library, from which additional cDNA clones, HUC 2, 3 and 4, were obtained. The four cDNA clones were sequenced and found to be overlapping, as illustrated in FIGS. 1A and 1B. The structure of cDNA and human DRADA protein was deduced from these clones. Following restriction site mapping to align the multiple overlapping cDNA clones, the nucleotide sequence of 6671 base pairs (bp) [SEQ ID NO:i]was determined for human DRADA.

Human DRADA polynucleotide sequence of 6671 base pairs contains a short 5' untranslated region (154 bp), and a long 3' untranslated region (2839 bp), including a polyadenylate tract of 99 bases (GenBank Accession No. U10439). This cDNA may contain the 5' end and/or cap site of DRADA mRNA. As shown in FIG. 2A, DRADA contained a single ORF (thin open box) which encodes a 1226-amino acid protein [SEQ ID NO: 2] with a calculated molecular mass of 136 kD. The proposed initiation codon is in agreement with the mammalian translation initiation consensus sequence [M. Kozak, *J. Cell Biol.*, 108:229–241 (1989)] and is preceded by an in-frame stop codon. The deduced amino acid sequence of this ORF is shown in FIG. 1 [SEQ ID NO:2].

Figure 2B:
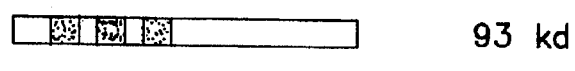
FIG. 2B illustrates a bar graph which represents the ORF for the 93 kD truncated form of human DRADA, with DRBM indicated by hatching.
Figure 2C:
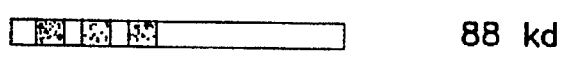
FIG. 2C illustrates a bar graph which represents the ORF for the 88 kD truncated form of human DRADA, with the DRBM indicated by hatching.

The ORF contained the NH$_2$-terminal sequences of both p93 and p88 kD protein, which appear to be both truncated forms, lacking, respectively, 403 and 439 amino acid residues of the NH$_2$-terminus of the full length 136-kDa DRADA protein (see FIGS. 2A through 2C by thick open boxes and in FIG. 1 by arrows). A putative bipartite nuclear localization signal is indicated in FIG. 2A by NUC, and a filled box and by boxing in FIG. 1. Three dsRNA binding motif (DRBM) repeats are indicated in FIGS. 1 and 2, as underlining or hatched boxes, respectively.

EXAMPLE 5

Expression of Human DRADA

Confirmation that the cDNA clone isolated does indeed code for DRADA was obtained by expressing this protein in *Spodoptera frugipedera* (Sf9) cells as a recombinant baculovirus protein. Two recombinant constructs that coded for a full-length DRADA protein (pVLDRADA140) or a mutant lacking the C-terminal 346 amino acids (pVLDRADAΔ) were made.

Figure 4A:
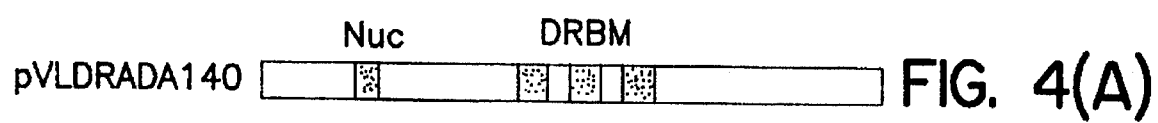
FIG. 4A illustrates a bar graph of plasmid pVLDRADA140, with the putative nuclear localization signal indicated by a black box (NUC), and the DRBM indicated by hatching.

For pVLDRADA140, XbaI to KpnI (the 5' end; 3.7 kb) of HUC1 and KpnI to XbaI (the 3' end; 1 kb) fragments of HUC2 were ligated into the commercially available baculovirus expression vector, pVL1393 (Invitrogen) at an XbaI site. The resulting recombinant expression vector pVLDRADA140 contained the endogenous translation initiation and termination codons as well as the 155 bp 5' untranslated sequence and 724 bp 3' untranslated sequence of full-length DRADA [SEQ ID NO: 1]. See FIG. 4A.

Figure 4B:
FIG. 4B illustrates a bar graph of plasmid pVLDRADAΔ with the putative nuclear localization signal indicated by a black box (NUC), and the dsRNA binding motifs (DRBM) indicated by hatching.

For pVLDRADA140Δ, a new termination codon was created at residue 880 by filling-in the overhang of the XmaIII located downstream of the dsRNA binding motifs (DRBM). This procedure replaced the original sequence SEQ ID NO: 37: KILAAIIMKKDSE with a newly created C-terminal sequence, SEQ ID NO: 38: PQDSGHH-HYEKRL at residues 867 to 879. See FIG. 4B.

Sf9 insect cells were infected with the above-described recombinant baculoviruses. Cells were cultured by conventional means.

Protein production was assessed by labeling Spodoptera frugiperdera (Sf9) cells with 50 µCi [$^{35}$S] methionine for 1 hour [O'Reilly et al, Baculovirus Expression Vectors, W. H. Freeman and Co., Oxford, England (1992)]. The labeled protein was analyzed by SDS-PAGE and fluorography. A unique band of 140 kD protein was detected in cells infected with the recombinant virus containing the entire coding sequence (DRADA140) indicating that a full length protein was expressed from the recombinant virus. A band of about 110 kD protein was detected in the cells infected with DRADAΔ.

The DRADA activity was analyzed in crude extracts made from $4 \times 10^7$ cells by the modified base assay as described previously in Wagner et al, (1990) cited above, using 20 µg of protein at 37° C. for 2 hours. See Example 2. As a reference, crude extracts made from Sf9 cells, as well as HeLa cells, were assayed using increasing amounts of protein.

Results of this assay are illustrated in FIG. 5. Only the extracts of the cells expressing DRADA140 showed adenosine to inosine conversion activity at a high level (5 times higher than that of HeLa nuclear extracts, which have previously been shown to contain a relatively high level of the DRADA activity [Wagner et al., (1990), cited above]). In contrast, the cells expressing a DRADAΔ, as well as uninfected Sf9 cells, displayed very little, if any, detectable base modification activity. These results confirm that the cloned cDNA indeed codes for a functional DRADA enzyme.

A separate assay tested in non-saturating, linear range (20 µg of protein t 37° C. for 30 min with excess of substrate dsRNA) indicated that Sf9 cells infected with DRADA 140 for 41 hours contained approximately 5 times more DRADA activity than HeLa cells.

Interestingly, the NH$_2$-terminally truncated forms of DRADA, p93 and p88, were not detected in Sf9 cells infected with recombinant virus carrying the entire DRADA ORF (FIG. 2A). Thus, these N-terminally truncated forms of DRADA appear to be produced by proteolysis during the protein purification.

EXAMPLE 6

Southern blot Analysis of the DRADA gene

The DRADA gene was detected in various species by Southern blot analysis. Briefly, twenty µg of chromosomal DNA was digested with either EcoRI and BamHI or EcoRI and HindIII, fractionated on an agarose gel (0.9%), and transferred to a Genescreen plus membrane. The membrane was hybridized with $^{32}$P-labeled probe (1.2 kb EcoRI/BamHI fragment of HUC1; $10^{16}$ cpm/mL) in solution containing 2×SSC, 1×Denhardt's solution, 40% formamide, 10% dextran sulfate, 1% SDS, and 0.05 mg/ml salmon sperm DNA, at 37° C. for 18 hours. The membrane was then washed with one change of 2×SSC at room temperature for 20 min followed by a wash with 2×SSC and 1% SDS at 37° C. for 30 minutes. The membrane was exposed at −70° C. for 68 hours.

The DNA was obtained from HeLa (human), BFA-1C BPT (bovine), MOPC11 (mouse), XTC-2 (Xenopus laevis; amphibian), and Sf9 (insect) cells. Two recently obtained overlapping human genomic clones were analyzed for restriction site mapping. These results suggest that all DNA bands including the faint ones arise from a single DRADA gene.

The Southern blot analysis indicated that the DRADA gene is well conserved in mammalian cells. The genomic DNA prepared from human, mouse, and bovine cells hybridized strongly with the human cDNA probe. However, this probe did not detect sequences in amphibian or insect genomes. Since the enzymatic activity of DRADA has been reported in these two species, additional cDNA probes including a DNA fragment encoding the C-terminal region predicted to contain the conserved catalytic domain were tested. All probes gave negative results. Thus, it is postulated that the DRADA sequence has not been well conserved during evolution, except in certain short stretches possibly involved in catalysis.

EXAMPLE 7

Northern blot Analysis of Human Tissues

Expression of transcripts encoding DRADA was studied by Northern hybridization against mRNA from various human tissues. A Northern blot containing 2 µg of polyA$^+$ RNA (Clontech) was hybridized with a human cDNA probe according to the manufacturer's instructions. Briefly, the blot was prehybridized in 5×SSPE, 10×Denhardt's solution, 50% formamide, 2% SDS, and 0.1 mg/ml denatured salmon sperm DNA at 42° C. for 4 hours, followed by hybridization in a fresh solution containing the denatured probe at 42° C. for 18 hours. The blot was washed with several changes of 2×SSC and 0.05% SDS at room temperature for 30 minutes, then with one change of 0.1×SSC and 0.1% SDS at 50° C. for 1 hour. The blot was rehybridized with a glyceraldehyde 3-phosphate dehydrogenase (G3PDH) cDNA control probe.

The resulting Northern analysis blot located DRADA transcripts in all tissues tested, including the heart, brain, placenta, lung, liver, muscle, kidney and pancreas. The size of the DRADA mRNA (7 kb) indicates that the overlapping cDNAs (6,671 nucleotides) contain nearly the entire DRADA mRNA. As previously shown by the modified-base assay of crude extracts made from various tissues, the DRADA gene appeared to be expressed ubiquitously.

Brain tissue contains a high level of DRADA transcript, consistent with proposed involvement in the RNA editing of glutamate-gated ion-channel transcripts [Sommer et al., Cell, 67:11–19 (1991); Higuchi et al., Cell, 75:1361–1370 (1993)].

EXAMPLE 8

Structural Features of DRADA

Computer-assisted inspection of the predicted primary structure revealed several features that illuminate the functional properties of DRADA. FIG. 6 illustrates similarities between DRADA and other dsRNA binding proteins. Alignments among different DRBM and deaminases were performed by the PILEUP, BESTFIT and GAP programs. Identification of various protein sequence motifs was performed by the MOTIFS program of the GCG sequence analysis package, version 7.0 [J. Devereux et al, *Nucleic Acids Res.*, 12:387-395 (1984)].

A. DRADA and dsRNA Interaction

The central region of the DRADA protein contains three repeats of a dsRNA binding motif (DRBM; see FIG. 1). The presence of dsRNA binding motifs in DRADA (aa500-700) were first recognized as three internal repeats revealed during computer analysis of DRADA amino acid sequences.

The presence of these motifs explains the selectivity of DRADA for duplex RNA and identifies DRADA as a member of a growing family of DRBM containing proteins. This motif was recognized by several different groups in a number of proteins that are presumed to bind dsRNA and to carry out. a diverse array of functions such as regulation of development, interaction with HIV, and cleavage of dsRNA. See, e.g., A. Gatignol et al, *Mol. Cell. Biol.*, 13:2193 (1993); and D. St. Johnson et al, *Proc. Natl. Acad. Sci. USA*, 89:10979 (1992) among others. For example, the dissociation constant (Kd) of DRADA to a 575 bp dsRNA was 0.23 nM comparable to other RNA binding proteins known to have very high affinity, such as TAT binding to TAR (Kd= 0.14 nM), and rev binding to RRE (Kd=0.3 nM) of HIV. Each motif is capable of binding independently to dsRNA allowing DRADA to make three contacts with dsRNA, and possibly increasing the affinity for dsRNA in a cooperative manner. It should be pointed out that multiple DRADA seem to bind to the long dsRNA, as binding studies and substrate requirement studies indicate [Nishikura et al, (1991), cited above].

These proteins carry out a diverse array of functions such as regulation and early development (Staufen) [St. Johnson et al, cited above] and interaction with human immunodeficiency virus RNA (TAR-binding protein) [Gatignol et al, cited above].

Note that there is an additional internal repeat at the position aa200-250 of SEQ ID NO: 2. This is not related to DRBM and appeared to be unique to human DRBM, since this repeat was not present in the bovine DRADA sequence.

There is a partial conservation of an RNP core consensus sequence just 62 residues upstream of DRBM-1 (GYVDF, residues 445-449 of SEQ ID NO: 2). The RNP consensus found in many SSRNA binding proteins, such as nucleolin and poly(A)-binding protein [S. R. Haynes, *New Biol.*, 4:421-429 (1992)], consists of a 90-residue stretch of loosely conserved sequence within which reside highly conserved core sequences of eight (RNP-1) and five (RNP-2) residues. The short RNP-2-like stretch found in DRADA may participate in destabilizing A-U base pairs and in creating a local SSRNA region before adenosine deaminase.

In addition to DRBM, the computer analysis of the DRADA sequence by the MOTIFS program (GCG) revealed the presence of a bipartite nuclear localization signal comprising two basic residues followed by ten flanking residues and a basic cluster at residues 169 through 185 of DRADA SEQ ID NO: 2. This is consistent with the finding of the DRADA activity in the biochemically purified nuclear fraction of mammalian cells and tissues. The DRADA sequence contained numerous potential phosphorylation sites hinting that DRADA activity may be regulated by phosphorylation. Furthermore, although the enzyme was originally called "dsRNA unwindase," inspection of DRADA sequence did not show any significant homology to known helicase (DEAD or DEAH proteins), confirming previous conclusions from biochemical analysis that DRADA does not have any classical helicase activity.

Since the biochemically purified 93 and 88 kD proteins, lacking the N-terminal region of the full length protein, exhibit the DRADA activity the amino acid residues directly involved in the catalytic mechanism are expected to reside at the C-terminal region, most likely the downstream of three repeats of DRBM. Note that the C-terminal truncated mutant (DRADAΔ) does not exhibit DRADA activity.

B. Catalytic Mechanism of DRADA and Conservation of Residues Required for Deamination A set of evolutionarily conserved amino acid residues arranged and spaced in a specific sequence context has been reported in adenosine deaminase (ADA) and adenosine monophosphate (AMP) deaminases has been reported [Z. Chang et al, *Biochem.*, 30:2273 (1991)], and also for cytidine deaminases and deoxycytidylate (dCMP).

The C-terminal region of DRADA contains the tripeptide sequences HAE and PCG, which are conserved in several cytidine and dCMP deaminases, including SEQ ID NO: 39: REPR [B. Teng et al, *Science*, 260:1816 (1993)]. (A database search revealed a nematode gene (T20H4.4) of unknown function [Wilson et al, *Nature (London)*, 368:32-38 (1994)] with a considerable degree of sequence conservation to the C-terminal region of DRADA, particularly around the tripeptide HAE and PCG sequences. This nematode gene may encode a prototype of the vertebrate version of DRADA.) REPR is believed to be a subunit of a multicomponent enzyme containing a specific cytidine deaminase activity responsible for the RNA editing of apolipoprotein B mRNAs. These tripeptides contain histidine, glutamic acid, and cysteine, which are likely to be involved in the coordination of a zinc atom and formation of the catalytic center of DRADA.

While certain embodiments of the invention have been particularly described, it will be apparent to those skilled in the art that many modifications and variations may be made. Therefore, the present invention is not to be construed as limited by any of the particular embodiments shown, rather its scope will be defined only by the claims which follow.

What is claimed is:

1. A human amino acid sequence selected from the group consisting of:
   a) SEQ ID NO:2 having double stranded ribonucleic acid adenosine deaminase (DRADA) protein activity; and
   (b) fragments of SEQ ID NO:2 having a DRADA-like biological activity.

2. A polynucleotide sequence isolated from other cellular materials and encoding a human double stranded ribonucleic acid adenosine deaminase (DRADA) protein, said polynucleotide sequence selected from the group consisting of SEQ ID NO:1 and fragments thereof encoding a protein having a DRADA-like biological activity.

3. The polynucleotide sequence of claim 2 labeled with a detectable label.

4. An expression vector comprising a polynucleotide sequence of claim 2 operably linked to an expression control sequence.

5. A host cell transformed with an expression vector of claim 4 and capable of expressing the DRADA protein.

6. A DNA probe comprising an oligonucleotide fragment consisting of at least 15 bp from the first 6572 bp of the polynucleotide sequence of SEQ ID NO:1 or its complementary strand and a detectable label.

7. A human double stranded ribonucleic acid adenosine deaminase (DRADA) protein fragment selected from the group consisting of the amino acid sequence of SEQ ID NO:3, the amino acid sequence of SEQ ID NO:4, and the amino acid sequence of SEQ ID NO:5.

8. A method of recombinantly producing a human double stranded ribonucleic acid adenosine deaminase (DRADA) protein selected from SEQ ID NO:2 and fragments thereof having a DRADA-like biological activity, said method comprising:

providing a vector containing a polynucleotide sequence isolated from other cellular materials and encoding the DRADA protein, said polynucleotide sequence selected from the group consisting of SEQ ID NO:1 and fragments thereof encoding a protein having a DRADA-like biological activity and an expression control sequence permitting expression of the DRADA protein;

transforming a selected host cell with said vector; and culturing said host cell under conditions which permit expression of the DRADA protein.

* * * * *

UNITED STATES PATENT AND TRADEMARK OFFICE
CERTIFICATE OF CORRECTION

Page 1 of 2

PATENT NO. : 5,643,778
DATED : July 1, 1997
INVENTOR(S) : Kazuko Nishikura

It is certified that error appears in the above-indentified patent and that said Letters Patent is hereby corrected as shown below:

Col. 1, line 35, delete "86.:2647" and insert in place thereof -- 86:2647 --.

Col. 1, line 41, delete "hydrolyric" and insert in place thereof -- hydrolytic --.

Col. 2, line 2, delete "Kirschher" and insert in place thereof -- Kirschner --.

Col. 13, line 9, delete "5'CCGGAATTCNGGNAAA/GGTNGA3'" and insert in place thereof -- 5'CC__GGAATTC__NGGNAAA/GGTNGA3' --.

Col. 13, line 11, delete "5'CGGGATCCNGCT/CTCCTT/CTGGT/CTTNA" and insert in place thereof -- 5'CG__GGATCC__NGCT/CTCCTT/CTGGT/CTTNA --.

Col. 13, line 15, delete "5'CGGAATTCAAA/GACNGGNTAC/TGTNGA3'" and insert in place thereof -- 5'C__GGAATTC__AAA/GACNGGNTAC/TGTNGA3' --.

Col. 13, line 16-17, delete "5,'CGGGATCCG/ATCG/ATCNGGG/T/AATG/ATCG/ATC3'" and insert in place thereof -- 5'CG__GGATCC__G/ATCG/ATCNGGG/T/AATG/ATCG/ATC3' --.

Col. 13, line 27, delete the "," after "5".

Col. 14, line 33, delete "[SEQ ID NO:i]" and insert in place thereof -- [SEQ ID NO: 1] --.

UNITED STATES PATENT AND TRADEMARK OFFICE
CERTIFICATE OF CORRECTION

PATENT NO. : 5,643,778
DATED : July 1, 1997
INVENTOR(S) : Kazuko Nishikura

It is certified that error appears in the above-identified patent and that said Letters Patent is hereby corrected as shown below:

Col. 15, line 52, delete "t" and insert in place thereof -- at --.

Signed and Sealed this

Twenty-seventh Day of January, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 39

( 2 ) INFORMATION FOR SEQ ID NO:1:

5,643,778

19 20
-continued ( i ) SEQUENCE CHARACTERISTICS:
    ( A ) LENGTH: 6671 base pairs
    ( B ) TYPE: nucleic acid
    ( C ) STRANDEDNESS: double
    ( D ) TOPOLOGY: unknown ( i i ) MOLECULE TYPE: cDNA ( i x ) FEATURE:
    ( A ) NAME/KEY: CDS
    ( B ) LOCATION: 155..3832

( x i ) SEQUENCE DESCRIPTION: SEQ ID NO:1:

```
CGCAGACCCG CGGAGTTTCC CGTGCCGACG CCCCGGGGCC ACTTCCAGTG CGGAGTAGCG       60

GAGGCGTGGG GGCCTCGAGG GGCTGGCGCG GTCCAGCGGT CGGGCCAGGG TCGTGCCGCC      120

GGCGGGTCGG GCCGGACAAT GCCTCGCGGG CGCA ATG AAT CCG CGG CAG GGG          172
                                     Met Asn Pro Arg Gln Gly
                                      1               5

TAT TCC CTC AGC GGA TAC TAC ACC CAT CCA TTT CAA GGC TAT GAG CAC       220
Tyr Ser Leu Ser Gly Tyr Tyr Thr His Pro Phe Gln Gly Tyr Glu His
            10              15                  20

AGA CAG CTC AGA TAC CAG CAG CCT GGG CCA GGA TCT TCC CCC AGT AGT       268
Arg Gln Leu Arg Tyr Gln Gln Pro Gly Pro Gly Ser Ser Pro Ser Ser
        25              30                  35

TTC CTG CTT AAG CAA ATA GAA TTT CTC AAG GGG CAG CTC CCA GAA GCA       316
Phe Leu Leu Lys Gln Ile Glu Phe Leu Lys Gly Gln Leu Pro Glu Ala
    40              45                  50

CCG GTG ATT GGA AAG CAG ACA CCG TCA CTG CCA CCT TCC CTC CCA GGA       364
Pro Val Ile Gly Lys Gln Thr Pro Ser Leu Pro Pro Ser Leu Pro Gly
55              60                  65                      70

CTC CGG CCA AGG TTT CCA GTA CTA CTT GCC TCC AGT ACC AGA GGC AGG       412
Leu Arg Pro Arg Phe Pro Val Leu Leu Ala Ser Ser Thr Arg Gly Arg
                75                  80                  85

CAA GTG GAC ATC AGG GGT GTC CCC AGG GGC GTG CAT CTC GGA AGT CAG       460
Gln Val Asp Ile Arg Gly Val Pro Arg Gly Val His Leu Gly Ser Gln
                90                  95                  100

GGG CTC CAG AGA GGG TTC CAG CAT CCT TCA CCA CGT GGC AGG AGT CTG       508
Gly Leu Gln Arg Gly Phe Gln His Pro Ser Pro Arg Gly Arg Ser Leu
            105                 110                 115

CCA CAG AGA GGT GTT GAT TGC CTT TCC TCA CAT TTC CAG GAA CTG AGT       556
Pro Gln Arg Gly Val Asp Cys Leu Ser Ser His Phe Gln Glu Leu Ser
        120                 125                 130

ATC TAC CAA GAT CAG GAA CAA AGG ATC TTA AAG TTC CTG GAA GAG CTT       604
Ile Tyr Gln Asp Gln Glu Gln Arg Ile Leu Lys Phe Leu Glu Glu Leu
135                 140                 145                 150

GGG GAA GGG AAG GCC ACC ACA GCA CAT GAT CTG TCT GGG AAA CTT GGG       652
Gly Glu Gly Lys Ala Thr Thr Ala His Asp Leu Ser Gly Lys Leu Gly
                155                 160                 165

ACT CCG AAG AAA GAA ATC AAT CGA GTT TTA TAC TCC CTG GCA AAG AAG       700
Thr Pro Lys Lys Glu Ile Asn Arg Val Leu Tyr Ser Leu Ala Lys Lys
            170                 175                 180

GGC AAG CTA CAG AAA GAG GCA GGA ACA CCC CCT TTG TGG AAA ATC GCG       748
Gly Lys Leu Gln Lys Glu Ala Gly Thr Pro Pro Leu Trp Lys Ile Ala
        185                 190                 195

GTC TCC ACT CAG GCT TGG AAC CAG CAC AGC GGA GTG GTA AGA CCA GAC       796
Val Ser Thr Gln Ala Trp Asn Gln His Ser Gly Val Val Arg Pro Asp
    200                 205                 210

GGT CAT AGC CAA GGA GCC CCA AAC TCA GAC CCG AGT TTG GAA CCG GAA       844
Gly His Ser Gln Gly Ala Pro Asn Ser Asp Pro Ser Leu Glu Pro Glu
215                 220                 225                 230

GAC AGA AAC TCC ACA TCT GTC TCA GAA GAT CTT CTT GAG CCT TTT ATT       892
Asp Arg Asn Ser Thr Ser Val Ser Glu Asp Leu Leu Glu Pro Phe Ile
```

|  |  |  |  |  |  |  |  | 235 |  |  |  |  | 240 |  |  |  |  | 245 |  |  |
|---|---|---|---|---|---|---|---|---|---|---|---|---|---|---|---|---|---|---|---|---|
| GCA | GTC | TCA | GCT | CAG | GCT | TGG | AAC | CAG | CAC | AGC | GGA | GTG | GTA | AGA | CCA | 940 |
| Ala | Val | Ser | Ala | Gln | Ala | Trp | Asn | Gln | His | Ser | Gly | Val | Val | Arg | Pro |  |
|  |  |  | 250 |  |  |  |  | 255 |  |  |  |  | 260 |  |  |  |
| GAC | AGT | CAT | AGC | CAA | GGA | TCC | CCA | AAC | TCA | GAC | CCA | GGT | TTG | GAA | CCT | 988 |
| Asp | Ser | His | Ser | Gln | Gly | Ser | Pro | Asn | Ser | Asp | Pro | Gly | Leu | Glu | Pro |  |
|  |  | 265 |  |  |  |  | 270 |  |  |  |  | 275 |  |  |  |  |
| GAA | GAC | AGC | AAC | TCC | ACA | TCT | GCC | TTG | GAA | GAT | CCT | CTT | GAG | TTT | TTA | 1036 |
| Glu | Asp | Ser | Asn | Ser | Thr | Ser | Ala | Leu | Glu | Asp | Pro | Leu | Glu | Phe | Leu |  |
| 280 |  |  |  |  | 285 |  |  |  |  | 290 |  |  |  |  |  |  |
| GAC | ATG | GCC | GAG | ATC | AAG | GAG | AAA | ATC | TGC | GAC | TAT | CTC | TTC | AAT | GTG | 1084 |
| Asp | Met | Ala | Glu | Ile | Lys | Glu | Lys | Ile | Cys | Asp | Tyr | Leu | Phe | Asn | Val |  |
| 295 |  |  |  | 300 |  |  |  | 305 |  |  |  |  |  |  | 310 |  |
| TCT | GAC | TCC | TCT | GCC | CTG | AAT | TTG | GCT | AAA | AAT | ATT | GGC | CTT | ACC | AAG | 1132 |
| Ser | Asp | Ser | Ser | Ala | Leu | Asn | Leu | Ala | Lys | Asn | Ile | Gly | Leu | Thr | Lys |  |
|  |  |  |  | 315 |  |  |  | 320 |  |  |  |  | 325 |  |  |  |
| GCC | CGA | GAT | ATA | AAT | GCT | GTG | CTA | ATT | GAC | ATG | GAA | AGG | CAG | GGG | GAT | 1180 |
| Ala | Arg | Asp | Ile | Asn | Ala | Val | Leu | Ile | Asp | Met | Glu | Arg | Gln | Gly | Asp |  |
|  |  |  | 330 |  |  |  |  | 335 |  |  |  |  | 340 |  |  |  |
| GTC | TAT | AGA | CAA | GGG | ACA | ACC | CCT | CCC | ATA | TGG | CAT | TTG | ACA | GAC | AAG | 1228 |
| Val | Tyr | Arg | Gln | Gly | Thr | Thr | Pro | Pro | Ile | Trp | His | Leu | Thr | Asp | Lys |  |
|  |  | 345 |  |  |  |  | 350 |  |  |  |  | 355 |  |  |  |  |
| AAG | CGA | GAG | AGG | ATG | CAA | ATC | AAG | AGA | AAT | ACG | AAC | AGT | GTT | CCT | GAA | 1276 |
| Lys | Arg | Glu | Arg | Met | Gln | Ile | Lys | Arg | Asn | Thr | Asn | Ser | Val | Pro | Glu |  |
|  | 360 |  |  |  |  | 365 |  |  |  |  | 370 |  |  |  |  |  |
| ACC | GCT | CCA | GCT | GCA | ATC | CCT | GAG | ACC | AAA | AGA | AAC | GCA | GAG | TTC | CTC | 1324 |
| Thr | Ala | Pro | Ala | Ala | Ile | Pro | Glu | Thr | Lys | Arg | Asn | Ala | Glu | Phe | Leu |  |
| 375 |  |  |  |  | 380 |  |  |  |  | 385 |  |  |  |  | 390 |  |
| ACC | TGT | AAT | ATA | CCC | ACA | TCA | AAT | GCC | TCA | AAT | AAC | ATG | GTA | ACC | ACA | 1372 |
| Thr | Cys | Asn | Ile | Pro | Thr | Ser | Asn | Ala | Ser | Asn | Asn | Met | Val | Thr | Thr |  |
|  |  |  |  | 395 |  |  |  |  | 400 |  |  |  |  | 405 |  |  |
| GAA | AAA | GTG | GAG | AAT | GGG | CAG | GAA | CCT | GTC | ATA | AAG | TTA | GAA | AAC | AGG | 1420 |
| Glu | Lys | Val | Glu | Asn | Gly | Gln | Glu | Pro | Val | Ile | Lys | Leu | Glu | Asn | Arg |  |
|  |  |  | 410 |  |  |  |  | 415 |  |  |  |  | 420 |  |  |  |
| CAA | GAG | GCC | AGA | CCA | GAA | CCA | GCA | AGA | CTG | AAA | CCA | CCT | GTT | CAT | TAC | 1468 |
| Gln | Glu | Ala | Arg | Pro | Glu | Pro | Ala | Arg | Leu | Lys | Pro | Pro | Val | His | Tyr |  |
|  |  | 425 |  |  |  |  | 430 |  |  |  |  | 435 |  |  |  |  |
| AAT | GGC | CCC | TCA | AAA | GCA | GGG | TAT | GTT | GAC | TTT | GAA | AAT | GGC | CAG | TGG | 1516 |
| Asn | Gly | Pro | Ser | Lys | Ala | Gly | Tyr | Val | Asp | Phe | Glu | Asn | Gly | Gln | Trp |  |
| 440 |  |  |  |  | 445 |  |  |  |  | 450 |  |  |  |  |  |  |
| GCC | ACA | GAT | GAC | ATC | CCA | GAT | GAC | TTG | AAT | AGT | ATC | CGC | GCA | GCA | CCA | 1564 |
| Ala | Thr | Asp | Asp | Ile | Pro | Asp | Asp | Leu | Asn | Ser | Ile | Arg | Ala | Ala | Pro |  |
| 455 |  |  |  |  | 460 |  |  |  |  | 465 |  |  |  |  | 470 |  |
| GGT | GAG | TTT | CGA | GCC | ATC | ATG | GAG | ATG | CCC | TCC | TTC | TAC | AGT | CAT | GGC | 1612 |
| Gly | Glu | Phe | Arg | Ala | Ile | Met | Glu | Met | Pro | Ser | Phe | Tyr | Ser | His | Gly |  |
|  |  |  |  | 475 |  |  |  |  | 480 |  |  |  |  | 485 |  |  |
| TTG | CCA | CGG | TGT | TCA | CCC | TAC | AAG | AAA | CTG | ACA | GAG | TGC | CAG | CTG | AAG | 1660 |
| Leu | Pro | Arg | Cys | Ser | Pro | Tyr | Lys | Lys | Leu | Thr | Glu | Cys | Gln | Leu | Lys |  |
|  |  |  | 490 |  |  |  |  | 495 |  |  |  |  | 500 |  |  |  |
| AAC | CCC | ATC | AGC | GGG | CTG | TTA | GAA | TAT | GCC | CAG | TTC | GCT | AGT | CAA | ACC | 1708 |
| Asn | Pro | Ile | Ser | Gly | Leu | Leu | Glu | Tyr | Ala | Gln | Phe | Ala | Ser | Gln | Thr |  |
|  |  | 505 |  |  |  |  | 510 |  |  |  |  | 515 |  |  |  |  |
| TGT | GAG | TTC | AAC | ATG | ATA | GAG | CAG | AGT | GGA | CCA | CCC | CAT | GAA | CCT | CGA | 1756 |
| Cys | Glu | Phe | Asn | Met | Ile | Glu | Gln | Ser | Gly | Pro | Pro | His | Glu | Pro | Arg |  |
| 520 |  |  |  |  | 525 |  |  |  |  | 530 |  |  |  |  |  |  |
| TTT | AAA | TTC | CAG | GTT | GTC | ATC | AAT | GGC | CGA | GAG | TTT | CCC | CCA | GCT | GAA | 1804 |
| Phe | Lys | Phe | Gln | Val | Val | Ile | Asn | Gly | Arg | Glu | Phe | Pro | Pro | Ala | Glu |  |
| 535 |  |  |  |  | 540 |  |  |  |  | 545 |  |  |  |  | 550 |  |
| GCT | GGA | AGC | AAG | AAA | GTG | GCC | AAG | CAG | GAT | GCA | GCT | ATG | AAA | GCC | ATG | 1852 |
| Ala | Gly | Ser | Lys | Lys | Val | Ala | Lys | Gln | Asp | Ala | Ala | Met | Lys | Ala | Met |  |

-continued

| | 555 | | | | | 560 | | | | | 565 | | | | |
|---|---|---|---|---|---|---|---|---|---|---|---|---|---|---|---|
| ACA | ATT | CTG | CTA | GAG | GAA | GCC | AAA | GCC | AAG | GAC | AGT | GGA | AAA | TCA | GAA | 1900 |
| Thr | Ile | Leu | Leu | Glu | Glu | Ala | Lys | Ala | Lys | Asp | Ser | Gly | Lys | Ser | Glu | |
| | | | 570 | | | | 575 | | | | | 580 | | | | |
| GAA | TCA | TCC | CAC | TAT | TCC | ACA | GAG | AAA | GAA | TCA | GAG | AAG | ACT | GCA | GAG | 1948 |
| Glu | Ser | Ser | His | Tyr | Ser | Thr | Glu | Lys | Glu | Ser | Glu | Lys | Thr | Ala | Glu | |
| | | 585 | | | | | 590 | | | | | 595 | | | | |
| TCC | CAG | ACC | CCC | ACC | CCT | TCA | GCC | ACA | TCC | TTC | TTT | TCT | GGG | AAG | AGC | 1996 |
| Ser | Gln | Thr | Pro | Thr | Pro | Ser | Ala | Thr | Ser | Phe | Phe | Ser | Gly | Lys | Ser | |
| | 600 | | | | | 605 | | | | | 610 | | | | | |
| CCC | GTC | ACC | ACA | CTG | CTT | GAG | TGT | ATG | CAC | AAA | TTG | GGG | AAC | TCC | TGC | 2044 |
| Pro | Val | Thr | Thr | Leu | Leu | Glu | Cys | Met | His | Lys | Leu | Gly | Asn | Ser | Cys | |
| 615 | | | | | 620 | | | | | 625 | | | | | 630 | |
| GAA | TTC | CGT | CTC | CTG | TCC | AAA | GAA | GGC | CCT | GCC | CAT | GAA | CCC | AAG | TTC | 2092 |
| Glu | Phe | Arg | Leu | Leu | Ser | Lys | Glu | Gly | Pro | Ala | His | Glu | Pro | Lys | Phe | |
| | | | | 635 | | | | | 640 | | | | | 645 | | |
| CAA | TAC | TGT | GTT | GCA | GTG | GGA | GCC | CAA | ACT | TTC | CCC | AGT | GTG | AGT | GCT | 2140 |
| Gln | Tyr | Cys | Val | Ala | Val | Gly | Ala | Gln | Thr | Phe | Pro | Ser | Val | Ser | Ala | |
| | | | 650 | | | | | 655 | | | | | 660 | | | |
| CCC | AGC | AAG | AAA | GTG | GCA | AAG | CAG | ATG | GCC | GCA | GAG | GAA | GCC | ATG | AAG | 2188 |
| Pro | Ser | Lys | Lys | Val | Ala | Lys | Gln | Met | Ala | Ala | Glu | Glu | Ala | Met | Lys | |
| | | 665 | | | | | 670 | | | | | 675 | | | | |
| GCC | CTG | CAT | GGG | GAG | GCG | ACC | AAC | TCC | ATG | GCT | TCT | GAT | AAC | CAG | CCT | 2236 |
| Ala | Leu | His | Gly | Glu | Ala | Thr | Asn | Ser | Met | Ala | Ser | Asp | Asn | Gln | Pro | |
| | 680 | | | | | 685 | | | | | 690 | | | | | |
| GAA | GGT | ATG | ATC | TCA | GAG | TCA | CTT | GAT | AAC | TTG | GAA | TCC | ATG | ATG | CCC | 2284 |
| Glu | Gly | Met | Ile | Ser | Glu | Ser | Leu | Asp | Asn | Leu | Glu | Ser | Met | Met | Pro | |
| 695 | | | | | 700 | | | | | 705 | | | | | 710 | |
| AAC | AAG | GTC | AGG | AAG | ATT | GGC | GAG | CTC | GTG | AGA | TAC | CTG | AAC | ACC | AAC | 2332 |
| Asn | Lys | Val | Arg | Lys | Ile | Gly | Glu | Leu | Val | Arg | Tyr | Leu | Asn | Thr | Asn | |
| | | | | 715 | | | | | 720 | | | | | 725 | | |
| CCT | GTG | GGT | GGC | CTT | TTG | GAG | TAC | GCC | CGC | TCC | CAT | GGC | TTT | GCT | GCT | 2380 |
| Pro | Val | Gly | Gly | Leu | Leu | Glu | Tyr | Ala | Arg | Ser | His | Gly | Phe | Ala | Ala | |
| | | | 730 | | | | | 735 | | | | | 740 | | | |
| GAA | TTC | AAG | TTG | GTC | GAC | CAG | TCC | GGA | CCT | CCT | CAC | GAG | CCC | AAG | TTC | 2428 |
| Glu | Phe | Lys | Leu | Val | Asp | Gln | Ser | Gly | Pro | Pro | His | Glu | Pro | Lys | Phe | |
| | | 745 | | | | | 750 | | | | | 755 | | | | |
| GTT | TAC | CAA | GCA | AAA | GTT | GGG | GGT | CGC | TGG | TTC | CCA | GCC | GTC | TGC | GCA | 2476 |
| Val | Tyr | Gln | Ala | Lys | Val | Gly | Gly | Arg | Trp | Phe | Pro | Ala | Val | Cys | Ala | |
| | 760 | | | | | 765 | | | | | 770 | | | | | |
| CAC | AGC | AAG | AAG | CAA | GGC | AAG | CAG | GAA | GCA | GCA | GAT | GCG | GCT | CTC | CGT | 2524 |
| His | Ser | Lys | Lys | Gln | Gly | Lys | Gln | Glu | Ala | Ala | Asp | Ala | Ala | Leu | Arg | |
| 775 | | | | | 780 | | | | | 785 | | | | | 790 | |
| GTC | TTG | ATT | GGG | GAG | AAC | GAG | AAG | GCA | GAA | CGC | ATG | GGT | TTC | ACA | GAG | 2572 |
| Val | Leu | Ile | Gly | Glu | Asn | Glu | Lys | Ala | Glu | Arg | Met | Gly | Phe | Thr | Glu | |
| | | | | 795 | | | | | 800 | | | | | 805 | | |
| GTA | ACC | CCA | GTG | ACA | GGG | GCC | AGT | CTC | AGA | AGA | ACT | ATG | CTC | CTC | CTC | 2620 |
| Val | Thr | Pro | Val | Thr | Gly | Ala | Ser | Leu | Arg | Arg | Thr | Met | Leu | Leu | Leu | |
| | | | 810 | | | | | 815 | | | | | 820 | | | |
| TCA | AGG | TCC | CCA | GAA | GCA | CAG | CCA | AAG | ACA | CTC | CCT | CTC | ACT | GGC | AGC | 2668 |
| Ser | Arg | Ser | Pro | Glu | Ala | Gln | Pro | Lys | Thr | Leu | Pro | Leu | Thr | Gly | Ser | |
| | | 825 | | | | | 830 | | | | | 835 | | | | |
| ACC | TTC | CAT | GAC | CAG | ATA | GCC | ATG | CTG | AGC | CAC | CGG | TGC | TTC | AAC | ACT | 2716 |
| Thr | Phe | His | Asp | Gln | Ile | Ala | Met | Leu | Ser | His | Arg | Cys | Phe | Asn | Thr | |
| | 840 | | | | | 845 | | | | | 850 | | | | | |
| CTG | ACT | AAC | AGC | TTC | CAG | CCC | TCC | TTG | CTC | GGC | CGC | AAG | ATT | CTG | GCC | 2764 |
| Leu | Thr | Asn | Ser | Phe | Gln | Pro | Ser | Leu | Leu | Gly | Arg | Lys | Ile | Leu | Ala | |
| 855 | | | | | 860 | | | | | 865 | | | | | 870 | |
| GCC | ATC | ATT | ATG | AAA | AAA | GAC | TCT | GAG | GAC | ATG | GGT | GTC | GTC | GTC | AGC | 2812 |
| Ala | Ile | Ile | Met | Lys | Lys | Asp | Ser | Glu | Asp | Met | Gly | Val | Val | Val | Ser | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 875 |     |     |     |     | 880 |     |     |     |     | 885 |     |      |
| TTG | GGA | ACA | GGG | AAT | CGC | TGT | GTG | AAA | GGA | GAT | TCT | CTC | AGC | CTA | AAA | 2860 |
| Leu | Gly | Thr | Gly | Asn | Arg | Cys | Val | Lys | Gly | Asp | Ser | Leu | Ser | Leu | Lys |      |
|     |     |     | 890 |     |     |     |     | 895 |     |     |     |     | 900 |     |     |      |
| GGA | GAA | ACT | GTC | AAT | GAC | TGC | CAT | GCA | GAA | ATA | ATC | TCC | CGG | AGA | GGC | 2908 |
| Gly | Glu | Thr | Val | Asn | Asp | Cys | His | Ala | Glu | Ile | Ile | Ser | Arg | Arg | Gly |      |
|     |     | 905 |     |     |     |     | 910 |     |     |     |     |     | 915 |     |     |      |
| TTC | ATC | AGG | TTT | CTC | TAC | AGT | GAG | TTA | ATG | AAA | TAC | AAC | TCC | CAG | ACT | 2956 |
| Phe | Ile | Arg | Phe | Leu | Tyr | Ser | Glu | Leu | Met | Lys | Tyr | Asn | Ser | Gln | Thr |      |
|     | 920 |     |     |     |     | 925 |     |     |     |     |     | 930 |     |     |     |      |
| GCG | AAG | GAT | AGT | ATA | TTT | GAA | CCT | GCT | AAG | GGA | GGA | GAA | AAG | CTC | CAA | 3004 |
| Ala | Lys | Asp | Ser | Ile | Phe | Glu | Pro | Ala | Lys | Gly | Gly | Glu | Lys | Leu | Gln |      |
| 935 |     |     |     |     | 940 |     |     |     |     | 945 |     |     |     |     | 950 |      |
| ATA | AAA | AAG | ACT | GTG | TCA | TTC | CAT | CTG | TAT | ATC | AGC | ACT | GCT | CCG | TGT | 3052 |
| Ile | Lys | Lys | Thr | Val | Ser | Phe | His | Leu | Tyr | Ile | Ser | Thr | Ala | Pro | Cys |      |
|     |     |     |     | 955 |     |     |     |     | 960 |     |     |     |     | 965 |     |      |
| GGA | GAT | GGC | GCC | CTC | TTT | GAC | AAG | TCC | TGC | AGC | GAC | CGT | GCT | ATG | GAA | 3100 |
| Gly | Asp | Gly | Ala | Leu | Phe | Asp | Lys | Ser | Cys | Ser | Asp | Arg | Ala | Met | Glu |      |
|     |     |     | 970 |     |     |     |     | 975 |     |     |     |     | 980 |     |     |      |
| AGC | ACA | GAA | TCC | CGC | CAC | TAC | CCT | GTC | TTC | GAG | AAT | CCC | AAA | CAA | GGA | 3148 |
| Ser | Thr | Glu | Ser | Arg | His | Tyr | Pro | Val | Phe | Glu | Asn | Pro | Lys | Gln | Gly |      |
|     |     | 985 |     |     |     |     | 990 |     |     |     |     | 995 |     |     |     |      |
| AAG | CTC | CGC | ACC | AAG | GTG | GAG | AAC | GGA | GAA | GGC | ACA | ATC | CCT | GTG | GAA | 3196 |
| Lys | Leu | Arg | Thr | Lys | Val | Glu | Asn | Gly | Glu | Gly | Thr | Ile | Pro | Val | Glu |      |
| 1000 |    |     |     |     | 1005 |    |     |     |     | 1010 |   |     |     |     |     |      |
| TCC | AGT | GAC | ATT | GTG | CCT | ACG | TGG | GAT | GGC | ATT | CGG | CTC | GGG | GAG | AGA | 3244 |
| Ser | Ser | Asp | Ile | Val | Pro | Thr | Trp | Asp | Gly | Ile | Arg | Leu | Gly | Glu | Arg |      |
| 1015 |    |     |     |     | 1020 |   |     |     |     | 1025 |   |     |     |     | 1030 |     |
| CTC | CGT | ACC | ATG | TCC | TGT | AGT | GAC | AAA | ATC | CTA | CGC | TGG | AAC | GTG | CTG | 3292 |
| Leu | Arg | Thr | Met | Ser | Cys | Ser | Asp | Lys | Ile | Leu | Arg | Trp | Asn | Val | Leu |      |
|     |     |     |     | 1035 |   |     |     |     | 1040 |   |     |     |     | 1045 |   |      |
| GGC | CTG | CAA | GGG | GCA | CTG | TTG | ACC | CAC | TTC | CTG | CAG | CCC | ATT | TAT | CTC | 3340 |
| Gly | Leu | Gln | Gly | Ala | Leu | Leu | Thr | His | Phe | Leu | Gln | Pro | Ile | Tyr | Leu |      |
|     |     |     | 1050 |   |     |     |     | 1055 |   |     |     |     | 1060 |   |     |      |
| AAA | TCT | GTC | ACA | TTG | GGT | TAC | CTT | TTC | AGC | CAA | GGG | CAT | CTG | ACC | CGT | 3388 |
| Lys | Ser | Val | Thr | Leu | Gly | Tyr | Leu | Phe | Ser | Gln | Gly | His | Leu | Thr | Arg |      |
|     |     |     | 1065 |   |     |     |     | 1070 |   |     |     |     | 1075 |   |     |      |
| GCT | ATT | TGC | TGT | CGT | GTG | ACA | AGA | GAT | GGG | AGT | GCA | TTT | GAG | GAT | GGA | 3436 |
| Ala | Ile | Cys | Cys | Arg | Val | Thr | Arg | Asp | Gly | Ser | Ala | Phe | Glu | Asp | Gly |      |
|     |     |     | 1080 |   |     |     |     | 1085 |   |     |     |     | 1090 |   |     |      |
| CTA | CGA | CAT | CCC | TTT | ATT | GTC | AAC | CAC | CCC | AAG | GTT | GGC | AGA | GTC | AGC | 3484 |
| Leu | Arg | His | Pro | Phe | Ile | Val | Asn | His | Pro | Lys | Val | Gly | Arg | Val | Ser |      |
| 1095 |   |     |     |     | 1100 |   |     |     |     | 1105 |   |     |     |     | 1110 |    |
| ATA | TAT | GAT | TCC | AAA | AGG | CAA | TCC | GGG | AAG | ACT | AAG | GAG | ACA | AGC | GTC | 3532 |
| Ile | Tyr | Asp | Ser | Lys | Arg | Gln | Ser | Gly | Lys | Thr | Lys | Glu | Thr | Ser | Val |      |
|     |     |     |     | 1115 |   |     |     |     | 1120 |   |     |     |     | 1125 |   |      |
| AAC | TGG | TGT | CTG | GCT | GAT | GGC | TAT | GAC | CTG | GAG | ATC | CTG | GAC | GGT | ACC | 3580 |
| Asn | Trp | Cys | Leu | Ala | Asp | Gly | Tyr | Asp | Leu | Glu | Ile | Leu | Asp | Gly | Thr |      |
|     |     |     | 1130 |   |     |     |     | 1135 |   |     |     |     | 1140 |   |     |      |
| AGA | GGC | ACT | GTG | GAT | GGG | CCA | CGG | AAT | GAA | TTG | TCC | CGG | GTC | TCC | AAA | 3628 |
| Arg | Gly | Thr | Val | Asp | Gly | Pro | Arg | Asn | Glu | Leu | Ser | Arg | Val | Ser | Lys |      |
|     |     |     | 1145 |   |     |     |     | 1150 |   |     |     |     | 1155 |   |     |      |
| AAG | AAC | ATT | TTT | CTT | CTA | TTT | AAG | AAG | CTC | TGC | TCC | TTC | CGT | TAC | CGC | 3676 |
| Lys | Asn | Ile | Phe | Leu | Leu | Phe | Lys | Lys | Leu | Cys | Ser | Phe | Arg | Tyr | Arg |      |
|     |     | 1160 |   |     |     |     | 1165 |   |     |     |     | 1170 |   |     |     |      |
| AGG | GAT | CTA | CTG | AGA | CTC | TCC | TAT | GGT | GAG | GCC | AAG | AAA | GCT | GCC | CGT | 3724 |
| Arg | Asp | Leu | Leu | Arg | Leu | Ser | Tyr | Gly | Glu | Ala | Lys | Lys | Ala | Ala | Arg |      |
| 1175 |   |     |     |     | 1180 |   |     |     |     | 1185 |   |     |     |     | 1190 |    |
| GAC | TAC | GAG | ACG | GCC | AAG | AAC | TAC | TTC | AAA | AAA | GGC | CTG | AAG | GAT | ATG | 3772 |
| Asp | Tyr | Glu | Thr | Ala | Lys | Asn | Tyr | Phe | Lys | Lys | Gly | Leu | Lys | Asp | Met |      |

```
                        1195                    1200                    1205
GGC TAT GGG AAC TGG ATT AGC AAA CCC CAG GAG GAA AAG AAC TTT TAT              3820
Gly Tyr Gly Asn Trp Ile Ser Lys Pro Gln Glu Glu Lys Asn Phe Tyr
                        1210                    1215                    1220

CTC TGC CCA GTA TAGTATGCTC CAGTGACAGA TGGATTAGGG TGTGTCATAC                  3872
Leu Cys Pro Val
            1225
```

| | | | | |
|---|---|---|---|---|
| TAGGGTGTGA | GAGAGGTAGG | TCGTAGCATT | CCTCATCACA | TGGTCAGGGG ATTTTTTTT | 3932 |
| CTCCTTTTTT | TTTTCTTTTT | AAGCCATAAT | TGGTGATACT | GAAAACTTTG GGTTCCCATT | 3992 |
| TATCCTGCTT | TCTTTGGGAT | TGCTAGGCAA | GGTCTGGCCA | GGCCCCCTT TTTTCCCCCA | 4052 |
| AGTGAAGAGG | CAGAAACCTA | AGAAGTTATC | TTTTCTTTCT | ACCCAAAGCA TACATAGTCA | 4112 |
| CTGAGCACCT | GCGGTCCATT | TCCTCTTAAA | AGTTTGTTT | TGATTTGTTT CCATTTCCTT | 4172 |
| TCCCTTTGTG | TTTGCTACAC | TGACCTCTTG | CGGTCTTGAT | TAGGTTTCAG TCAACTCTGG | 4232 |
| ATCATGTCAG | GGACTGATAA | TTTCATTTGT | GGATTACGCA | GACCCTCTA CTTCCCTCT | 4292 |
| TTCCCTTCTG | AGATTCTTTC | CTTGTGATCT | GAATGTCTCC | TTTTCCCCCT CAGAGGGCAA | 4352 |
| AGAGGTGAAC | ATAAAGGATT | TGGTGAAACA | TTTGTAAGGG | TAGGAGTTGA AAACTGCAGT | 4412 |
| TCCCAGTGCC | ACGGAAGTGT | GATTGGAGCC | TGCAGATAAT | GCCCAGCCAT CCTCCCATCC | 4472 |
| TGCACTTTAG | CCAGCTGCAG | GGCGGGCAAG | GCAAGGAAAG | CTGCTTCCCT GGAAGTGTAT | 4532 |
| CACTTTCTCC | GGCAGCTGGG | AAGTCTAGAA | CCAGCCAGAC | TGGGTTAAGG GAGCTGCTCA | 4592 |
| AGCAATAGCA | GAGGTTTCAC | CCGGCAGGAT | GACACAGACC | ACTTCCCAGG GAGCACGGGC | 4652 |
| ATGCCTTGGA | ATATTGCCAA | GCTTCCAGCT | GCCTCTTCTC | CTAAAGCATT CCTAGGAATA | 4712 |
| TTTTCCCCGC | CAATGCTGGG | CGTACACCCT | AGCCAACGGG | ACAAATCCTA GAGGGTATAA | 4772 |
| AATCATCTCT | GCTCAGATAA | TCATGACTTA | GCAAGAATAA | GGGCAAAAAA TCCTGTTGGC | 4832 |
| TTAACGTCAC | TGTTCCACCC | GGTGTAATAT | CTCTCATGAC | AGTGACACCA AGGGAAGTTG | 4892 |
| ACTAAGTCAC | ATGTAAATTA | GGAGTGTTTT | AAAGAATGCC | ATAGATGTTG ATTCTTAACT | 4952 |
| GCTACAGATA | ACCTGTAATT | GAGCAGATTT | AAAATTCAGG | CATACTTTC CATTTATCCA | 5012 |
| AGTGCTTTCA | TTTTCCAGA | TGGCTTCAGA | AGTAGGCTCG | TGGGCAGGGC GCAGACCTGA | 5072 |
| TCTTTATAGG | GTTGACATAG | AAAGCAGTAG | TTGTGGGTGA | AAGGGCAGGT TGTCTTCAAA | 5132 |
| CTCTGTGAGG | TAGAATCCTT | TGTCTATACC | TCCATGAACA | TTGACTCGTG TGTTCAGAGC | 5192 |
| CTTTGGCCTC | TCTGTGGAGT | CTGGCTCTCT | GGCTCCTGTG | CATTCTTTGA ATAGTCACTC | 5252 |
| GTAAAAACTG | TCAGTGCTTG | AAACTGTTTC | CTTTACTCAT | GTTGAAGGGA CTTTGTTGGC | 5312 |
| TTTTAGAGTG | TTGGTCATGA | CTCCAAGAGC | AGAGCAGGGA | AGAGCCCAAG CATAGACTTG | 5372 |
| GTGCCGTGGT | GATGGCTGCA | GTCCAGTTTT | GTGATGCTGC | TTTTACGTGT CCCTCGATAA | 5432 |
| CAGTCAGCTA | GACACACTCA | GGAGGACTAC | TGAGGCTCTG | CGACCTTCAG GAGCTGAGCC | 5492 |
| TGCCTCTCTC | CTTTAGATGA | CAGACCTTCA | TCTGGGAACG | TGCTGAGCCA GCACCCTCAG | 5552 |
| ATGATTTCCC | TCCAAACTGC | TGACTAGGTC | ATCCTCTGTC | TGGTAGAGAC ATTCACATCT | 5612 |
| TTGCTTTTAT | TCTATGCTCT | CTGTACTTTT | GACCAAAAAT | TGACCAAAGT AAGAAAATGC | 5672 |
| AAGTTCTAAA | AATAGACTAA | GGATGCCTTT | GCAGAACACC | AAAGCATCCC AAGGAACTGG | 5732 |
| TAGGGAAGTG | GCGCCTGTCT | CCTGGAGTGG | AAGAGGCCTG | CTCCCTGCTC TGGGTCTGCT | 5792 |
| GGGGGCACAG | TAAATCAGTC | TTGGCACCCA | CATCCAGGGC | AGAGAGGTCT GTGGTTCTCA | 5852 |
| GCATCAGAAG | GCAGCGCAGC | CCCTCTCCTC | TTCAGGCTAC AGGGTTGTCA | CCTGCTGAGT | 5912 |
| CCTCAGGTTG | TTTGGCCTCT | CTGGTCCATC | TTGGGCATTA | GGTTCTCCAG CAGAGCTCTG | 5972 |

-continued

```
GCCAGCTGCC TCTTCTTTAA CTGGGAACAC AGGCTCTCAC AAGATCAGAA CCCCCACTCA      6032

CCCCCAAGAT CTTATCTAGC AAGCCTGTAG TATTCAGTTT CTGTTGTAGG AAGAGAGCGA      6092

GGCATCCCTG AATTCCACGC ATCTGCTGGA AACGAGCCGT GTCAGATCGC ACATCCCTGC      6152

GCCCCCATGC CCCTCTGAGT CACACAGGAC AGAGGAGGCA GAGCTTCTGC CCACTGTTAT      6212

CTTCACTTTC TTTGTCCAGT CTTTTGTTTT TAATAAGCAG TGACCCTCCC TACTCTTCTT      6272

TTTAATGATT TTTGTAGTTG ATTTGTCTGA ACTGTGGCTA CTGTGCATTC CTTGAATAAT      6332

CACTTGTAAA AATTGTCAGT GCTTGAAGCT GTTTCCTTTA CTCACATTGA AGGGACTTCG      6392

TTGGTTTTTT GGAGTCTTGG TTGTGACTCC AAGAGCAGAG TGAGGAAGAC CCCCAAGCAT      6452

AGACTCGGGT ACTGTGATGA TGGCTGCAGT CCAGTTTTAT GATTCTGCTT TTATGTGTCC      6512

CTTGATAACA GTGACTTAAC AATATACATT CCTCATAAAT AAAAAAAAAA CAAGAATCTG      6572

AAAAAAAAAA AAAAAAAAAA AAAAAAAAAA AAAAAAAAAA AAAAAAAAAA AAAAAAAAAA      6632

AAAAAAAAAA AAAAAAAAAA AAAAAAAAAA AAAAAAAA                             6671
```

( 2 ) INFORMATION FOR SEQ ID NO:2:

( i ) SEQUENCE CHARACTERISTICS:
        ( A ) LENGTH: 1226 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asn Pro Arg Gln Gly Tyr Ser Leu Ser Gly Tyr Tyr Thr His Pro
 1               5                  10                  15

Phe Gln Gly Tyr Glu His Arg Gln Leu Arg Tyr Gln Gln Pro Gly Pro
                20                  25                  30

Gly Ser Ser Pro Ser Ser Phe Leu Leu Lys Gln Ile Glu Phe Leu Lys
            35                  40                  45

Gly Gln Leu Pro Glu Ala Pro Val Ile Gly Lys Gln Thr Pro Ser Leu
        50                  55                  60

Pro Pro Ser Leu Pro Gly Leu Arg Pro Arg Phe Pro Val Leu Leu Ala
 65                 70                  75                  80

Ser Ser Thr Arg Gly Arg Gln Val Asp Ile Arg Gly Val Pro Arg Gly
                85                  90                  95

Val His Leu Gly Ser Gln Gly Leu Gln Arg Gly Phe Gln His Pro Ser
               100                 105                 110

Pro Arg Gly Arg Ser Leu Pro Gln Arg Gly Val Asp Cys Leu Ser Ser
           115                 120                 125

His Phe Gln Glu Leu Ser Ile Tyr Gln Asp Gln Glu Gln Arg Ile Leu
       130                 135                 140

Lys Phe Leu Glu Glu Leu Gly Glu Gly Lys Ala Thr Thr Ala His Asp
145                 150                 155                 160

Leu Ser Gly Lys Leu Gly Thr Pro Lys Lys Glu Ile Asn Arg Val Leu
                165                 170                 175

Tyr Ser Leu Ala Lys Lys Gly Lys Leu Gln Lys Glu Ala Gly Thr Pro
            180                 185                 190

Pro Leu Trp Lys Ile Ala Val Ser Thr Gln Ala Trp Asn Gln His Ser
        195                 200                 205

Gly Val Val Arg Pro Asp Gly His Ser Gln Gly Ala Pro Asn Ser Asp
    210                 215                 220

Pro Ser Leu Glu Pro Glu Asp Arg Asn Ser Thr Ser Val Ser Glu Asp
225                 230                 235                 240
```

```
Leu Leu Glu Pro Phe Ile Ala Val Ser Ala Gln Ala Trp Asn Gln His
            245             250             255
Ser Gly Val Val Arg Pro Asp Ser His Ser Gln Gly Ser Pro Asn Ser
            260             265             270
Asp Pro Gly Leu Glu Pro Glu Asp Ser Asn Ser Thr Ser Ala Leu Glu
            275             280             285
Asp Pro Leu Glu Phe Leu Asp Met Ala Glu Ile Lys Glu Lys Ile Cys
        290             295             300
Asp Tyr Leu Phe Asn Val Ser Asp Ser Ser Ala Leu Asn Leu Ala Lys
305             310             315             320
Asn Ile Gly Leu Thr Lys Ala Arg Asp Ile Asn Ala Val Leu Ile Asp
            325             330             335
Met Glu Arg Gln Gly Asp Val Tyr Arg Gln Gly Thr Thr Pro Pro Ile
            340             345             350
Trp His Leu Thr Asp Lys Lys Arg Glu Arg Met Gln Ile Lys Arg Asn
            355             360             365
Thr Asn Ser Val Pro Glu Thr Ala Pro Ala Ala Ile Pro Glu Thr Lys
        370             375             380
Arg Asn Ala Glu Phe Leu Thr Cys Asn Ile Pro Thr Ser Asn Ala Ser
385             390             395             400
Asn Asn Met Val Thr Thr Glu Lys Val Glu Asn Gly Gln Glu Pro Val
            405             410             415
Ile Lys Leu Glu Asn Arg Gln Glu Ala Arg Pro Glu Pro Ala Arg Leu
            420             425             430
Lys Pro Pro Val His Tyr Asn Gly Pro Ser Lys Ala Gly Tyr Val Asp
            435             440             445
Phe Glu Asn Gly Gln Trp Ala Thr Asp Asp Ile Pro Asp Asp Leu Asn
450             455             460
Ser Ile Arg Ala Ala Pro Gly Glu Phe Arg Ala Ile Met Glu Met Pro
465             470             475             480
Ser Phe Tyr Ser His Gly Leu Pro Arg Cys Ser Pro Tyr Lys Lys Leu
            485             490             495
Thr Glu Cys Gln Leu Lys Asn Pro Ile Ser Gly Leu Leu Glu Tyr Ala
            500             505             510
Gln Phe Ala Ser Gln Thr Cys Glu Phe Asn Met Ile Glu Gln Ser Gly
        515             520             525
Pro Pro His Glu Pro Arg Phe Lys Phe Gln Val Val Ile Asn Gly Arg
        530             535             540
Glu Phe Pro Pro Ala Glu Ala Gly Ser Lys Lys Val Ala Lys Gln Asp
545             550             555             560
Ala Ala Met Lys Ala Met Thr Ile Leu Leu Glu Glu Ala Lys Ala Lys
            565             570             575
Asp Ser Gly Lys Ser Glu Glu Ser Ser His Tyr Ser Thr Glu Lys Glu
            580             585             590
Ser Glu Lys Thr Ala Glu Ser Gln Thr Pro Thr Pro Ser Ala Thr Ser
            595             600             605
Phe Phe Ser Gly Lys Ser Pro Val Thr Thr Leu Leu Glu Cys Met His
            610             615             620
Lys Leu Gly Asn Ser Cys Glu Phe Arg Leu Leu Ser Lys Glu Gly Pro
625             630             635             640
Ala His Glu Pro Lys Phe Gln Tyr Cys Val Ala Val Gly Ala Gln Thr
            645             650             655
Phe Pro Ser Val Ser Ala Pro Ser Lys Lys Val Ala Lys Gln Met Ala
```

|     |     | 660 |     |     |     | 665 |     |     |     | 670 |     |     |     |
| --- | --- | --- | --- | --- | --- | --- | --- | --- | --- | --- | --- | --- | --- |
| Ala | Glu | Glu | Ala | Met | Lys | Ala | Leu | His | Gly | Glu | Ala | Thr | Asn | Ser | Met |
|     |     | 675 |     |     |     | 680 |     |     |     | 685 |     |     |     |
| Ala | Ser | Asp | Asn | Gln | Pro | Glu | Gly | Met | Ile | Ser | Glu | Ser | Leu | Asp | Asn |
|     |     | 690 |     |     |     | 695 |     |     |     | 700 |     |     |     |
| Leu | Glu | Ser | Met | Met | Pro | Asn | Lys | Val | Arg | Lys | Ile | Gly | Glu | Leu | Val |
|     |     | 705 |     |     |     | 710 |     |     |     | 715 |     |     |     | 720 |
| Arg | Tyr | Leu | Asn | Thr | Asn | Pro | Val | Gly | Gly | Leu | Leu | Glu | Tyr | Ala | Arg |
|     |     |     |     | 725 |     |     |     | 730 |     |     |     |     |     | 735 |
| Ser | His | Gly | Phe | Ala | Ala | Glu | Phe | Lys | Leu | Val | Asp | Gln | Ser | Gly | Pro |
|     |     |     | 740 |     |     |     | 745 |     |     |     |     | 750 |     |     |
| Pro | His | Glu | Pro | Lys | Phe | Val | Tyr | Gln | Ala | Lys | Val | Gly | Gly | Arg | Trp |
|     |     | 755 |     |     |     |     | 760 |     |     |     |     |     | 765 |     |
| Phe | Pro | Ala | Val | Cys | Ala | His | Ser | Lys | Lys | Gln | Gly | Lys | Gln | Glu | Ala |
|     |     | 770 |     |     |     |     | 775 |     |     |     |     | 780 |     |     |
| Ala | Asp | Ala | Ala | Leu | Arg | Val | Leu | Ile | Gly | Glu | Asn | Glu | Lys | Ala | Glu |
| 785 |     |     |     |     | 790 |     |     |     |     | 795 |     |     |     |     | 800 |
| Arg | Met | Gly | Phe | Thr | Glu | Val | Thr | Pro | Val | Thr | Gly | Ala | Ser | Leu | Arg |
|     |     |     |     | 805 |     |     |     |     | 810 |     |     |     |     | 815 |     |
| Arg | Thr | Met | Leu | Leu | Leu | Ser | Arg | Ser | Pro | Glu | Ala | Gln | Pro | Lys | Thr |
|     |     |     | 820 |     |     |     |     | 825 |     |     |     |     | 830 |     |     |
| Leu | Pro | Leu | Thr | Gly | Ser | Thr | Phe | His | Asp | Gln | Ile | Ala | Met | Leu | Ser |
|     |     |     | 835 |     |     |     |     | 840 |     |     |     | 845 |     |     |     |
| His | Arg | Cys | Phe | Asn | Thr | Leu | Thr | Asn | Ser | Phe | Gln | Pro | Ser | Leu | Leu |
|     | 850 |     |     |     |     | 855 |     |     |     |     | 860 |     |     |     |     |
| Gly | Arg | Lys | Ile | Leu | Ala | Ala | Ile | Ile | Met | Lys | Lys | Asp | Ser | Glu | Asp |
| 865 |     |     |     |     | 870 |     |     |     |     | 875 |     |     |     |     | 880 |
| Met | Gly | Val | Val | Val | Ser | Leu | Gly | Thr | Gly | Asn | Arg | Cys | Val | Lys | Gly |
|     |     |     |     | 885 |     |     |     |     | 890 |     |     |     |     | 895 |     |
| Asp | Ser | Leu | Ser | Leu | Lys | Gly | Glu | Thr | Val | Asn | Asp | Cys | His | Ala | Glu |
|     |     |     |     | 900 |     |     |     |     | 905 |     |     |     | 910 |     |     |
| Ile | Ile | Ser | Arg | Arg | Gly | Phe | Ile | Arg | Phe | Leu | Tyr | Ser | Glu | Leu | Met |
|     |     |     | 915 |     |     |     |     | 920 |     |     |     |     | 925 |     |     |
| Lys | Tyr | Asn | Ser | Gln | Thr | Ala | Lys | Asp | Ser | Ile | Phe | Glu | Pro | Ala | Lys |
|     | 930 |     |     |     |     | 935 |     |     |     |     |     | 940 |     |     |     |
| Gly | Gly | Glu | Lys | Leu | Gln | Ile | Lys | Lys | Thr | Val | Ser | Phe | His | Leu | Tyr |
| 945 |     |     |     |     | 950 |     |     |     |     | 955 |     |     |     |     | 960 |
| Ile | Ser | Thr | Ala | Pro | Cys | Gly | Asp | Gly | Ala | Leu | Phe | Asp | Lys | Ser | Cys |
|     |     |     |     | 965 |     |     |     |     | 970 |     |     |     |     | 975 |     |
| Ser | Asp | Arg | Ala | Met | Glu | Ser | Thr | Glu | Ser | Arg | His | Tyr | Pro | Val | Phe |
|     |     |     | 980 |     |     |     |     | 985 |     |     |     |     | 990 |     |     |
| Glu | Asn | Pro | Lys | Gln | Gly | Lys | Leu | Arg | Thr | Lys | Val | Glu | Asn | Gly | Glu |
|     |     | 995 |     |     |     |     | 1000 |     |     |     |     | 1005 |     |     |     |
| Gly | Thr | Ile | Pro | Val | Glu | Ser | Ser | Asp | Ile | Val | Pro | Thr | Trp | Asp | Gly |
|     |     | 1010 |     |     |     |     | 1015 |     |     |     |     | 1020 |     |     |     |
| Ile | Arg | Leu | Gly | Glu | Arg | Leu | Arg | Thr | Met | Ser | Cys | Ser | Asp | Lys | Ile |
| 1025 |     |     |     |     | 1030 |     |     |     |     | 1035 |     |     |     |     | 1040 |
| Leu | Arg | Trp | Asn | Val | Leu | Gly | Leu | Gln | Gly | Ala | Leu | Leu | Thr | His | Phe |
|     |     |     |     | 1045 |     |     |     |     | 1050 |     |     |     |     | 1055 |     |
| Leu | Gln | Pro | Ile | Tyr | Leu | Lys | Ser | Val | Thr | Leu | Gly | Tyr | Leu | Phe | Ser |
|     |     |     |     | 1060 |     |     |     |     | 1065 |     |     |     |     | 1070 |     |
| Gln | Gly | His | Leu | Thr | Arg | Ala | Ile | Cys | Cys | Arg | Val | Thr | Arg | Asp | Gly |
|     |     |     | 1075 |     |     |     |     | 1080 |     |     |     |     | 1085 |     |     |

```
Ser Ala Phe Glu Asp Gly Leu Arg His Pro Phe Ile Val Asn His Pro
    1090                1095                1100

Lys Val Gly Arg Val Ser Ile Tyr Asp Ser Lys Arg Gln Ser Gly Lys
1105                1110                1115                1120

Thr Lys Glu Thr Ser Val Asn Trp Cys Leu Ala Asp Gly Tyr Asp Leu
            1125                1130                1135

Glu Ile Leu Asp Gly Thr Arg Gly Thr Val Asp Gly Pro Arg Asn Glu
            1140                1145                1150

Leu Ser Arg Val Ser Lys Lys Asn Ile Phe Leu Leu Phe Lys Lys Leu
            1155                1160                1165

Cys Ser Phe Arg Tyr Arg Arg Asp Leu Leu Arg Leu Ser Tyr Gly Glu
            1170                1175                1180

Ala Lys Lys Ala Ala Arg Asp Tyr Glu Thr Ala Lys Asn Tyr Phe Lys
1185                1190                1195                1200

Lys Gly Leu Lys Asp Met Gly Tyr Gly Asn Trp Ile Ser Lys Pro Gln
            1205                1210                1215

Glu Glu Lys Asn Phe Tyr Leu Cys Pro Val
            1220                1225
```

( 2 ) INFORMATION FOR SEQ ID NO:3:

( i ) SEQUENCE CHARACTERISTICS:
( A ) LENGTH: 72 amino acids
( B ) TYPE: amino acid
( D ) TOPOLOGY: unknown ( i i ) MOLECULE TYPE: protein ( x i ) SEQUENCE DESCRIPTION: SEQ ID NO:3:

```
Lys Asn Pro Ile Ser Gly Leu Leu Glu Tyr Ala Gln Phe Ala Ser Gln
1               5                   10                  15

Thr Cys Glu Phe Asn Met Ile Glu Gln Ser Gly Pro Pro His Glu Pro
            20                  25                  30

Arg Phe Lys Phe Gln Val Val Ile Asn Gly Arg Glu Phe Pro Pro Ala
            35                  40                  45

Glu Ala Gly Ser' Lys Lys Val Ala Lys Gln Asp Ala Ala Met Lys Ala
        50                  55                  60

Met Thr Ile Leu Leu Glu Glu Ala
65                  70
```

( 2 ) INFORMATION FOR SEQ ID NO:4:

( i ) SEQUENCE CHARACTERISTICS:
( A ) LENGTH: 72 amino acids
( B ) TYPE: amino acid
( D ) TOPOLOGY: unknown ( i i ) MOLECULE TYPE: protein ( x i ) SEQUENCE DESCRIPTION: SEQ ID NO:4:

```
Lys Ser Pro Val Thr Thr Leu Leu Glu Cys Met His Lys Leu Gly Asn
1               5                   10                  15

Ser Cys Glu Phe Arg Leu Leu Ser Lys Gly Pro Ala His Glu Pro
            20                  25                  30

Lys Phe Gln Tyr Cys Val Ala Val Gly Ala Gln Thr Phe Pro Ser Val
            35                  40                  45

Ser Ala Pro Ser Lys Lys Val Ala Lys Gln Met Ala Ala Glu Glu Ala
        50                  55                  60

Met Lys Ala Leu His Gly Glu Ala
65                  70
```

( 2 ) INFORMATION FOR SEQ ID NO:5:

( i ) SEQUENCE CHARACTERISTICS:
        ( A ) LENGTH: 72 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:5:

```
Thr Asn Pro Val Gly Gly Leu Leu Glu Tyr Ala Arg Ser His Gly Phe
1               5                   10                  15

Ala Ala Glu Phe Lys Leu Val Asp Gln Ser Gly Pro Pro His Glu Pro
            20                  25                  30

Lys Phe Val Tyr Gln Ala Lys Val Gly Gly Arg Trp Phe Pro Ala Val
        35                  40                  45

Cys Ala His Ser Lys Lys Gln Gly Lys Gln Glu Ala Ala Asp Ala Ala
    50                  55                  60

Leu Arg Val Leu Ile Gly Glu Asn
65                  70
```

( 2 ) INFORMATION FOR SEQ ID NO:6:

( i ) SEQUENCE CHARACTERISTICS:
        ( A ) LENGTH: 73 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:6:

```
Ala Gly Phe Phe Met Glu Glu Leu Asn Thr Tyr Arg Gln Lys Gln Gly
1               5                   10                  15

Val Val Leu Lys Tyr Gln Glu Leu Pro Asn Ser Gly Pro Pro His Asp
            20                  25                  30

Arg Arg Phe Thr Phe Gln Val Ile Ile Asp Gly Arg Glu Phe Pro Glu
        35                  40                  45

Gly Glu Gly Arg Ser Lys Lys Glu Ala Lys Asn Ala Ala Ala Lys Leu
    50                  55                  60

Ala Val Glu Ile Leu Asn Lys Glu Lys
65                  70
```

( 2 ) INFORMATION FOR SEQ ID NO:7:

( i ) SEQUENCE CHARACTERISTICS:
        ( A ) LENGTH: 71 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:7:

```
Gly Asn Tyr Ile Gly Leu Ile Asn Arg Ile Ala Gln Lys Lys Arg Leu
1               5                   10                  15

Thr Val Asn Tyr Glu Gln Cys Ala Ser Gly Val His Gly Pro Glu Gly
            20                  25                  30

Phe Glu Tyr Lys Cys Lys Met Gly Gln Lys Glu Tyr Ser Ile Gly Thr
        35                  40                  45

Gly Ser Thr Lys Gln Glu Ala Lys Gln Leu Ala Ala Lys Leu Ala Tyr
    50                  55                  60

Leu Gln Ile Leu Ser Glu Glu
```

( 2 ) INFORMATION FOR SEQ ID NO:8:

( i ) SEQUENCE CHARACTERISTICS:
        ( A ) LENGTH: 72 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:8:

```
Gly Phe Tyr Met Asp Lys Leu Asn Lys Tyr Arg Gln Met His Gly Val
  1               5                  10                  15
Ala Ile Thr Tyr Lys Glu Leu Ser Thr Ser Gly Pro Pro His Asp Arg
             20                  25                  30
Arg Phe Thr Phe Gln Val Leu Ile Asp Glu Lys Glu Phe Gly Glu Ala
         35                  40                  45
Lys Gly Arg Ser Lys Thr Glu Ala Arg Asn Ala Ala Ala Lys Leu Ala
     50                  55                  60
Val Asp Ile Leu Asp Asn Glu Asn
 65                  70
```

( 2 ) INFORMATION FOR SEQ ID NO:9:

( i ) SEQUENCE CHARACTERISTICS:
        ( A ) LENGTH: 72 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:9:

```
Val Gly Asn Tyr Ile Gly Leu Val Asn Ser Phe Ala Gln Lys Lys Lys
  1               5                  10                  15
Leu Ser Val Leu Ile Glu Gln Cys Glu Pro Asn Ser Glu Leu Pro Gln
             20                  25                  30
Arg Phe Ile Cys Lys Cys Lys Ile Gly Gln Thr Met Tyr Gly Thr Gly
         35                  40                  45
Ser Gly Val Thr Lys Gln Glu Ala Lys Gln Leu Ala Ala Lys Glu Ala
     50                  55                  60
Tyr Gln Lys Leu Leu Lys Ser Pro
 65                  70
```

( 2 ) INFORMATION FOR SEQ ID NO:10:

( i ) SEQUENCE CHARACTERISTICS:
        ( A ) LENGTH: 71 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:10:

```
Lys Thr Pro Ile Ser Leu Leu Gln Glu Tyr Gly Thr Arg Ile Gly Lys
  1               5                  10                  15
Thr Pro Val Tyr Asp Leu Leu Lys Ala Glu Gly Gln Ala His Gln Pro
             20                  25                  30
Asn Phe Thr Phe Arg Val Thr Val Gly Asp Thr Ser Cys Thr Gly Gln
         35                  40                  45
Gly Pro Ser Lys Lys Ala Ala Lys His Lys Ala Ala Glu Val Ala Leu
     50                  55                  60
```

```
        Lys  Glu  Leu  Lys  Gly  Gly  Ser
         65                 70
```

( 2 ) INFORMATION FOR SEQ ID NO:11:

( i ) SEQUENCE CHARACTERISTICS:
        ( A ) LENGTH: 72 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:11:

```
Cys  Asn  Pro  Val  Gly  Ala  Leu  Gln  Glu  Leu  Val  Val  Gln  Lys  Gly  Trp
 1                  5                       10                       15

Arg  Leu  Pro  Glu  Tyr  Thr  Val  Thr  Gln  Glu  Ser  Gly  Pro  Ala  His  Arg
               20                       25                  30

Lys  Glu  Phe  Thr  Met  Thr  Cys  Arg  Val  Glu  Arg  Phe  Ile  Glu  Ile  Gly
              35                      40                       45

Ser  Gly  Thr  Ser  Lys  Lys  Leu  Ala  Lys  Arg  Asn  Ala  Ala  Ala  Lys  Met
     50                      55                       60

Leu  Leu  Arg  Val  His  Thr  Val  Pro
 65                 70
```

( 2 ) INFORMATION FOR SEQ ID NO:12:

( i ) SEQUENCE CHARACTERISTICS:
        ( A ) LENGTH: 73 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:12:

```
Gly  Pro  Ala  Cys  Cys  Arg  Val  Leu  Ser  Glu  Leu  Ser  Glu  Glu  Gln  Ala
 1                  5                       10                       15

Phe  His  Val  Ser  Tyr  Leu  Asp  Ile  Glu  Glu  Leu  Ser  Leu  Ser  Gly  Leu
               20                       25                       30

Cys  Gln  Cys  Leu  Val  Glu  Leu  Ser  Thr  Gln  Pro  Ala  Thr  Val  Cys  His
              35                      40                       45

Gly  Ser  Ala  Thr  Thr  Arg  Glu  Ala  Ala  Arg  Gly  Glu  Ala  Ala  Arg  Arg
     50                      55                       60

Ala  Leu  Gln  Tyr  Leu  Lys  Ile  Met  Ala
 65                 70
```

( 2 ) INFORMATION FOR SEQ ID NO:13:

( i ) SEQUENCE CHARACTERISTICS:
        ( A ) LENGTH: 71 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:13:

```
Glu  Thr  Pro  Ile  Gln  Leu  Leu  His  Glu  Phe  Gly  Thr  Lys  Thr  Gly  Asn
 1                  5                       10                       15

His  Pro  Val  Tyr  Thr  Leu  Glu  Lys  Ala  Glu  Gly  Gln  Ala  His  Asn  Pro
               20                       25                       30

Ser  Phe  Thr  Phe  Arg  Leu  Val  Ile  Gly  Asp  Ile  Thr  Ser  Leu  Gly  Glu
              35                      40                       45

Gly  Pro  Ser  Lys  Lys  Thr  Pro  Lys  Gln  Lys  Ala  Ala  Glu  Phe  Ala  Leu
     50                      55                       60
```

```
        Asn  Ile  Leu  Arg  Gly  Asp  Thr
        65                  70
```

(2) INFORMATION FOR SEQ ID NO:14:

(i) SEQUENCE CHARACTERISTICS:
        (A) LENGTH: 72 amino acids
        (B) TYPE: amino acid
        (D) TOPOLOGY: unknown (ii) MOLECULE TYPE: protein (xi) SEQUENCE DESCRIPTION: SEQ ID NO:14:

```
Glu  Asn  Pro  Val  Gly  Ser  Leu  Gln  Glu  Leu  Ala  Val  Gln  Lys  Gly  Trp
1                   5                        10                            15

Arg  Leu  Pro  Glu  Tyr  Thr  Val  Ala  Gln  Glu  Ser  Gly  Pro  Pro  His  Lys
               20                       25                       30

Arg  Glu  Phe  Thr  Ile  Thr  Cys  Arg  Val  Glu  Thr  Phe  Val  Glu  Thr  Gly
          35                       40                       45

Ser  Gly  Thr  Ser  Lys  Gln  Val  Ala  Lys  Arg  Val  Ala  Ala  Glu  Lys  Leu
     50                  55                       60

Leu  Thr  Lys  Phe  Lys  Thr  Ile  Ser
65                  70
```

(2) INFORMATION FOR SEQ ID NO:15:

(i) SEQUENCE CHARACTERISTICS:
        (A) LENGTH: 72 amino acids
        (B) TYPE: amino acid
        (D) TOPOLOGY: unknown (ii) MOLECULE TYPE: protein (xi) SEQUENCE DESCRIPTION: SEQ ID NO:15:

```
Thr  Asp  Tyr  Val  Lys  Met  Leu  Lys  Asp  Val  Ala  Glu  Glu  Leu  Asp  Phe
1                   5                        10                            15

Asn  Leu  Thr  Tyr  Leu  Asp  Ile  Asp  Glu  Leu  Ser  Val  Asn  Gly  Gln  Tyr
               20                       25                       30

Gln  Cys  Leu  Ala  Glu  Leu  Ser  Thr  Asn  Pro  Ile  Thr  Val  Cys  His  Gly
          35                       40                       45

Thr  Gly  Ile  Ser  Cys  Gly  Asn  Ala  His  Asn  Asp  Ala  Ala  His  Asn  Ala
     50                  55                       60

Leu  Gln  Tyr  Leu  Lys  Ile  Met  Cys
65                  70
```

(2) INFORMATION FOR SEQ ID NO:16:

(i) SEQUENCE CHARACTERISTICS:
        (A) LENGTH: 71 amino acids
        (B) TYPE: amino acid
        (D) TOPOLOGY: unknown (ii) MOLECULE TYPE: protein (xi) SEQUENCE DESCRIPTION: SEQ ID NO:16:

```
Lys  Thr  Pro  Met  Cys  Leu  Val  Asn  Glu  Leu  Ala  Arg  Tyr  Asn  Lys  Ile
1                   5                        10                            15

Thr  His  Gln  Tyr  Arg  Leu  Thr  Glu  Glu  Arg  Gly  Pro  Ala  His  Cys  Lys
               20                       25                       30

Thr  Phe  Thr  Val  Thr  Leu  Met  Leu  Gly  Asp  Glu  Glu  Tyr  Ser  Ala  Asp
          35                       40                       45

Gly  Phe  Lys  Ile  Lys  Lys  Ala  Gln  His  Leu  Ala  Ala  Ser  Lys  Ala  Ile
```

```
                    5 0                     5 5                        6 0

Glu  Glu  Thr  Met  Tyr  Lys  His
     6 5                     7 0
```

( 2 ) INFORMATION FOR SEQ ID NO:17:

( i ) SEQUENCE CHARACTERISTICS:
   ( A ) LENGTH: 69 amino acids
   ( B ) TYPE: amino acid
   ( D ) TOPOLOGY: unknown ( i i ) MOLECULE TYPE: protein ( x i ) SEQUENCE DESCRIPTION: SEQ ID NO:17:

```
     Lys  Phe  Pro  Ser  Arg  Phe  Ala  Leu  Pro  Pro  Pro  Leu  Gly  Ala  His  Val
     1                  5                        1 0                        1 5

His  His  Gly  Pro  Asn  Gly  Pro  Phe  Pro  Ser  Val  Pro  Thr  Pro  Pro  Ser
                       2 0                        2 5                        3 0

Lys  Ile  Thr  Leu  Phe  Val  Gly  Lys  Gln  Lys  Phe  Val  Gly  Ile  Gly  Arg
                  3 5                        4 0                        4 5

Thr  Leu  Gln  Gln  Ala  Lys  His  Asp  Ala  Ala  Ala  Arg  Ala  Leu  Gln  Val
               5 0                        5 5                        6 0

Leu  Lys  Thr  Gln  Ala
     6 5
```

( 2 ) INFORMATION FOR SEQ ID NO:18:

( i ) SEQUENCE CHARACTERISTICS:
   ( A ) LENGTH: 71 amino acids
   ( B ) TYPE: amino acid
   ( D ) TOPOLOGY: unknown ( i i ) MOLECULE TYPE: protein ( x i ) SEQUENCE DESCRIPTION: SEQ ID NO:18:

```
     Lys  Ser  Pro  Ile  Ser  Gln  Val  His  Glu  Ile  Gly  Ile  Lys  Arg  Asn  Met
     1                  5                        1 0                        1 5

Thr  Val  His  Phe  Lys  Val  Leu  Arg  Glu  Glu  Gly  Pro  Ala  His  Met  Lys
                       2 0                        2 5                        3 0

Asn  Phe  Ile  Thr  Ala  Cys  Ile  Val  Gly  Ser  Ile  Val  Thr  Glu  Gly  Glu
                  3 5                        4 0                        4 5

Gly  Asn  Gly  Lys  Lys  Val  Ser  Lys  Lys  Arg  Ala  Ala  Glu  Lys  Met  Leu
               5 0                        5 5                        6 0

Val  Glu  Leu  Gln  Lys  Leu  Pro
     6 5                     7 0
```

( 2 ) INFORMATION FOR SEQ ID NO:19:

( i ) SEQUENCE CHARACTERISTICS:
   ( A ) LENGTH: 73 amino acids
   ( B ) TYPE: amino acid
   ( D ) TOPOLOGY: unknown ( i i ) MOLECULE TYPE: protein ( x i ) SEQUENCE DESCRIPTION: SEQ ID NO:19:

```
     Asp  Asn  Pro  Ile  Thr  Lys  Leu  Ile  Gln  Leu  Gln  Gln  Thr  Arg  Lys  Glu
     1                  5                        1 0                        1 5

Lys  Glu  Pro  Ile  Phe  Glu  Leu  Ile  Ala  Lys  Asn  Gly  Asn  Glu  Thr  Ala
                       2 0                        2 5                        3 0

Arg  Arg  Arg  Glu  Phe  Val  Met  Glu  Val  Ser  Ala  Ser  Gly  Ser  Thr  Ala
                  3 5                        4 0                        4 5
```

```
          Arg   Gly   Thr   Gly   Asn   Ser   Lys   Lys   Leu   Ala   Lys   Arg   Asn   Ala   Ala   Gln
                50                              55                              60

Ala   Leu   Phe   Glu   Leu   Leu   Glu   Ala   Val
          65                      70
```

( 2 ) INFORMATION FOR SEQ ID NO:20:

( i ) SEQUENCE CHARACTERISTICS:
        ( A ) LENGTH: 70 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:20:

```
          His   Met   Lys   Glu   Gln   Leu   Leu   Tyr   Leu   Ser   Lys   Leu   Leu   Asp   Phe   Glu
          1                       5                             10                              15

Val   Asn   Phe   Ser   Asp   Tyr   Pro   Lys   Gly   Asn   His   Asn   Glu   Phe   Leu   Thr
                            20                            25                              30

Ile   Val   Thr   Leu   Ser   Thr   His   Pro   Pro   Gln   Ile   Cys   His   Gly   Val   Gly
                      35                            40                            45

Lys   Ser   Ser   Glu   Glu   Ser   Gln   Asn   Asp   Ala   Ala   Ser   Asn   Ala   Leu   Lys
                50                              55                              60

Ile   Leu   Ser   Lys   Leu   Gly
          65                      70
```

( 2 ) INFORMATION FOR SEQ ID NO:21:

( i ) SEQUENCE CHARACTERISTICS:
        ( A ) LENGTH: 74 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:21:

```
          Lys   His   Pro   Val   Ser   Ala   Leu   Met   Glu   Ile   Cys   Asn   Lys   Arg   Arg   Trp
          1                       5                             10                              15

Gln   Pro   Pro   Glu   Phe   Leu   Leu   Val   His   Asp   Ser   Gly   Pro   Asp   His   Arg
                            20                            25                              30

Lys   His   Phe   Leu   Phe   Arg   Val   Leu   Ile   Asn   Gly   Ser   Ala   Tyr   Gln   Pro
                      35                            40                            45

Ser   Phe   Ala   Ser   Pro   Asn   Lys   Lys   Glu   Ala   Lys   Ala   Thr   Ala   Ala   Thr
                50                              55                              60

Val   Val   Leu   Gln   Ala   Met   Gly   Leu   Val   Pro
          65                      70
```

( 2 ) INFORMATION FOR SEQ ID NO:22:

( i ) SEQUENCE CHARACTERISTICS:
        ( A ) LENGTH: 71 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:22:

```
          Ala   Asn   Pro   Val   Thr   Val   Ile   Asn   Glu   Tyr   Cys   Gln   Ile   Thr   Arg   Arg
          1                       5                             10                              15

Asp   Trp   Ser   Phe   Arg   Ile   Glu   Ser   Val   Gly   Pro   Ser   Asn   Ser   Pro   Thr
                            20                            25                              30

Phe   Tyr   Ala   Cys   Val   Asp   Ile   Asp   Gly   Arg   Val   Phe   Asp   Lys   Ala   Asp
                      35                            40                            45
```

```
         Gly Lys Ser Lys Arg Asp Ala Lys Asn Asn Ala Ala Lys Leu Ala Val
             50                  55                  60

Asp Lys Leu Leu Gly Tyr Val
         65                  70
```

( 2 ) INFORMATION FOR SEQ ID NO:23:

( i ) SEQUENCE CHARACTERISTICS:
        ( A ) LENGTH: 69 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:23:

```
         Pro Asp Pro Leu Ile Arg Leu Asn Asp Cys Lys Thr Lys Tyr Gly Ile
         1               5                   10                  15

Asp Ile Ile Cys Arg Phe Tyr Ile Val Leu Asp Asn Asp Gly Ser Ile
                     20                  25                  30

Ile His Met Cys Tyr Met Arg Thr Gly Ser Ala Glu Ala Val Ala Lys
                     35                  40                  45

Gly Arg Ser Lys Lys Glu Ala Lys Arg Ile Ala Ala Lys Asp Ile Leu
             50                  55                  60

Asp Gln Ile Gly Leu
         65
```

( 2 ) INFORMATION FOR SEQ ID NO:24:

( i ) SEQUENCE CHARACTERISTICS:
        ( A ) LENGTH: 71 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:24:

```
         Asp Lys Leu Ala Lys Ser Lys Leu Phe His Lys Tyr Ser Thr Leu Gly
         1               5                   10                  15

His Ile Glu Tyr Arg Trp Val Asp Gly Ala Gly Gly Ser Ala Glu Gly
                     20                  25                  30

Tyr Val Ile Ala Cys Ile Phe Asn Gly Lys Glu Val Ala Arg Ala Trp
                     35                  40                  45

Gly Ala Asn Gln Lys Asp Ala Gly Ser Arg Ala Ala Met Gln Ala Leu
             50                  55                  60

Glu Val Leu Ala Lys Asp Tyr
         65                  70
```

( 2 ) INFORMATION FOR SEQ ID NO:25:

( i ) SEQUENCE CHARACTERISTICS:
        ( A ) LENGTH: 73 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:25:

```
         Lys Asp Pro Lys Thr Arg Leu Gln Glu Tyr Leu Gln Gly Arg His Leu
         1               5                   10                  15

Pro Leu Pro Thr Tyr Leu Val Val Gln Val Arg Gly Glu Ala His Asp
                     20                  25                  30

Gln Glu Phe Thr Ile His Cys Gln Val Ser Gly Leu Ser Glu Pro Val
```

|     |     |     |     |     | 35  |     |     |     |     | 40  |     |     |     |     | 45  |
| --- | --- | --- | --- | --- | --- | --- | --- | --- | --- | --- | --- | --- | --- | --- | --- |
| Val | Gly | Thr | Gly | Ser | Ser | Arg | Arg | Lys | Ala | Glu | Gln | Ala | Ala | Ala | Glu |
|     |     |     | 50  |     |     |     |     | 55  |     |     |     |     | 60  |     |     |
| Gln | Ala | Leu | Lys | Lys | Leu | Glu | Leu | Glu |
|     |     |     | 65  |     |     |     | 70  |     |

( 2 ) INFORMATION FOR SEQ ID NO:26:

( i ) SEQUENCE CHARACTERISTICS:
        ( A ) LENGTH: 56 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 4..5
        ( D ) OTHER INFORMATION: /note= "Amino acid in position 4
                can be Val, Ile, Met or Leu."

( i x ) FEATURE:
        ( A ) NAME/KEY: Modified-site
        ( B ) LOCATION: 5..6
        ( D ) OTHER INFORMATION: /note= "Amino acid in position 5
                can be Gly or Ala."

( i x ) FEATURE:
        ( A ) NAME/KEY: Modified-site
        ( B ) LOCATION: 6..7
        ( D ) OTHER INFORMATION: /note= "Amino acid in position 6
                can be Leu, Met or Val."

( i x ) FEATURE:
        ( A ) NAME/KEY: Modified-site
        ( B ) LOCATION: 7..8
        ( D ) OTHER INFORMATION: /note= "Amino acid in position 7
                can be Leu, Ile, Val or Met."

( i x ) FEATURE:
        ( A ) NAME/KEY: Modified-site
        ( B ) LOCATION: 8..9
        ( D ) OTHER INFORMATION: /note= "Amino acid in position 8
                can be Asn or Gln."

( i x ) FEATURE:
        ( A ) NAME/KEY: Modified-site
        ( B ) LOCATION: 9..10
        ( D ) OTHER INFORMATION: /note= "Amino acid in position 9
                can be Glu or Asp."

( i x ) FEATURE:
        ( A ) NAME/KEY: Modified-site
        ( B ) LOCATION: 10..11
        ( D ) OTHER INFORMATION: /note= "Amino acid in position 10
                can be Tyr, Phe, Leu, Ile or Val."

( i x ) FEATURE:
        ( A ) NAME/KEY: Modified-site
        ( B ) LOCATION: 11..12
        ( D ) OTHER INFORMATION: /note= "Amino acid in position 11
                can be Ala or Gly."

( i x ) FEATURE:
        ( A ) NAME/KEY: Modified-site
        ( B ) LOCATION: 13..14
        ( D ) OTHER INFORMATION: /note= "Amino acid in position 13
                can be Lys or Arg."

( i x ) FEATURE:
        ( A ) NAME/KEY: Modified-site
        ( B ) LOCATION: 14..15
        ( D ) OTHER INFORMATION: /note= "Amino acid in position 14
                can be Gly or Ala."

( i x ) FEATURE:
        ( A ) NAME/KEY: Modified-site (B) LOCATION: 17..18
(D) OTHER INFORMATION: /note= "Amino acid in position 17 can be Tyr or Phe."

(ix) FEATURE:
(A) NAME/KEY: Modified-site
(B) LOCATION: 18..19
(D) OTHER INFORMATION: /note= "Amino acid in position 18 can be Leu, Val, Ile or Met."

(ix) FEATURE:
(A) NAME/KEY: Modified-site
(B) LOCATION: 19..20
(D) OTHER INFORMATION: /note= "Amino acid in position 19 can be Leu, Val or Ile."

(ix) FEATURE:
(A) NAME/KEY: Modified-site
(B) LOCATION: 20..21
(D) OTHER INFORMATION: /note= "Amino acid in position 20 can be Glu or Asp."

(ix) FEATURE:
(A) NAME/KEY: Modified-site
(B) LOCATION: 24..25
(D) OTHER INFORMATION: /note= "Amino acid in position 24 can be Ala or Gly."

(ix) FEATURE:
(A) NAME/KEY: Modified-site
(B) LOCATION: 26..27
(D) OTHER INFORMATION: /note= "Amino acid in position 26 can be Asp or Glu."

(ix) FEATURE:
(A) NAME/KEY: Modified-site
(B) LOCATION: 27..28
(D) OTHER INFORMATION: /note= "Amino acid in position 27 can be Pro, Lys or Arg."

(ix) FEATURE:
(A) NAME/KEY: Modified-site
(B) LOCATION: 28..29
(D) OTHER INFORMATION: /note= "Amino acid in position 28 can be Lys or Arg."

(ix) FEATURE:
(A) NAME/KEY: Modified-site
(B) LOCATION: 29..30
(D) OTHER INFORMATION: /note= "Amino acid in position 29 can be Phe or Tyr."

(ix) FEATURE:
(A) NAME/KEY: Modified-site
(B) LOCATION: 30..31
(D) OTHER INFORMATION: /note= "Amino acid in position 30 can be Thr, Ile, Leu, or Val."

(ix) FEATURE:
(A) NAME/KEY: Modified-site
(B) LOCATION: 31..32
(D) OTHER INFORMATION: /note= "Amino acid in position 31 can be Phe or Tyr."

(ix) FEATURE:
(A) NAME/KEY: Modified-site
(B) LOCATION: 32..33
(D) OTHER INFORMATION: /note= "Amino acid in position 32 can be Val, Leu, Met or Cys."

(ix) FEATURE:
(A) NAME/KEY: Modified-site
(B) LOCATION: 33..34
(D) OTHER INFORMATION: /note= "Amino acid in position 33 can be Val, Ile, Met or Leu."

(ix) FEATURE:
(A) NAME/KEY: Modified-site
(B) LOCATION: 35..36
(D) OTHER INFORMATION: /note= "Amino acid in position 35 can be Gly or Ala."

( i x ) FEATURE:
    ( A ) NAME/KEY: Modified-site
    ( B ) LOCATION: 36..37
    ( D ) OTHER INFORMATION: /note= "Amino acid in position 36
        can be Arg or Lys."

( i x ) FEATURE:
    ( A ) NAME/KEY: Modified-site
    ( B ) LOCATION: 38..39
    ( D ) OTHER INFORMATION: /note= "Amino acid in position 38
        can be Phe or Tyr."

( i x ) FEATURE:
    ( A ) NAME/KEY: Modified-site
    ( B ) LOCATION: 39..40
    ( D ) OTHER INFORMATION: /note= "Amino acid in position 39
        can be Gly or Ala."

( i x ) FEATURE:
    ( A ) NAME/KEY: Modified-site
    ( B ) LOCATION: 40..41
    ( D ) OTHER INFORMATION: /note= "Amino acid in position 40
        can be Ser or Thr."

( i x ) FEATURE:
    ( A ) NAME/KEY: Modified-site
    ( B ) LOCATION: 41..42
    ( D ) OTHER INFORMATION: /note= "Amino acid in position 41
        can be Gly or Ala."

( i x ) FEATURE:
    ( A ) NAME/KEY: Modified-site
    ( B ) LOCATION: 42..43
    ( D ) OTHER INFORMATION: /note= "Amino acid in position 42
        can be Ser or Thr."

( i x ) FEATURE:
    ( A ) NAME/KEY: Modified-site
    ( B ) LOCATION: 43..44
    ( D ) OTHER INFORMATION: /note= "Amino acid in position 43
        can be Lys or Arg."

( i x ) FEATURE:
    ( A ) NAME/KEY: Modified-site
    ( B ) LOCATION: 44..45
    ( D ) OTHER INFORMATION: /note= "Amino acid in position 44
        can be Lys or Arg."

( i x ) FEATURE:
    ( A ) NAME/KEY: Modified-site
    ( B ) LOCATION: 45..46
    ( D ) OTHER INFORMATION: /note= "Amino acid in position 45
        can be Glu or Asp."

( i x ) FEATURE:
    ( A ) NAME/KEY: Modified-site
    ( B ) LOCATION: 47..48
    ( D ) OTHER INFORMATION: /note= "Amino acid in position 47
        can be Lys or Arg."

( i x ) FEATURE:
    ( A ) NAME/KEY: Modified-site
    ( B ) LOCATION: 48..49
    ( D ) OTHER INFORMATION: /note= "Amino acid in position 48
        can be Gln or Asn."

( i x ) FEATURE:
    ( A ) NAME/KEY: Modified-site
    ( B ) LOCATION: 51..52
    ( D ) OTHER INFORMATION: /note= "Amino acid in position 51
        can be Glu, Asp, Lys or Arg."

( i x ) FEATURE:
    ( A ) NAME/KEY: Modified-site
    ( B ) LOCATION: 53..54
    ( D ) OTHER INFORMATION: /note= "Amino acid in position 53
        can be Leu, Val, Met or Ile."

( i x ) FEATURE:
  ( A ) NAME/KEY: Modified-site
  ( B ) LOCATION: 54..55
  ( D ) OTHER INFORMATION: /note= "Amino acid in position 54
    can be Ile or Val."

( i x ) FEATURE:
  ( A ) NAME/KEY: Modified-site
  ( B ) LOCATION: 55..56
  ( D ) OTHER INFORMATION: /note= "Amino acid in position 55
    can be Leu, Ile, Met or Val."

( i x ) FEATURE:
  ( A ) NAME/KEY: Modified-site
  ( B ) LOCATION: 55..56
  ( D ) OTHER INFORMATION: /note= "Amino acid in position 56
    can be Glu or Asp."

( x i ) SEQUENCE DESCRIPTION: SEQ ID NO:26:

```
Lys Asn Pro Xaa Xaa Xaa Xaa Xaa Xaa Xaa Gln Xaa Xaa Pro Glu
 1           5                       10                  15

Xaa Xaa Xaa Xaa Ser Gly Pro Xaa His Xaa Xaa Xaa Xaa Xaa Xaa
            20                  25                  30

Xaa Gly Xaa Xaa Glu Xaa Xaa Xaa Xaa Xaa Xaa Xaa Ala Xaa Xaa
        35                  40                  45

Ala Ala Xaa Ala Xaa Xaa Xaa Xaa
        50                  55
```

( 2 ) INFORMATION FOR SEQ ID NO:27:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: unknown ( i i ) MOLECULE TYPE: cDNA ( x i ) SEQUENCE DESCRIPTION: SEQ ID NO:27:

CCGGAATTCN GGNAAAGGTN GA    22

( 2 ) INFORMATION FOR SEQ ID NO:28:

( i ) SEQUENCE CHARACTERISTICS:
    ( A ) LENGTH: 5 amino acids
    ( B ) TYPE: amino acid
    ( D ) TOPOLOGY: unknown ( i i ) MOLECULE TYPE: protein ( x i ) SEQUENCE DESCRIPTION: SEQ ID NO:28:

```
Pro Gly Lys Val Glu
 1               5
```

( 2 ) INFORMATION FOR SEQ ID NO:29:

( i ) SEQUENCE CHARACTERISTICS:
    ( A ) LENGTH: 28 base pairs
    ( B ) TYPE: nucleic acid
    ( C ) STRANDEDNESS: double
    ( D ) TOPOLOGY: unknown ( i i ) MOLECULE TYPE: cDNA ( x i ) SEQUENCE DESCRIPTION: SEQ ID NO:29:

CGGGATCCNG CTCTCCTTCT GGTCTTNA    28

( 2 ) INFORMATION FOR SEQ ID NO:30:

( i ) SEQUENCE CHARACTERISTICS:
    ( A ) LENGTH: 5 amino acids
    ( B ) TYPE: amino acid
    ( D ) TOPOLOGY: unknown ( i i ) MOLECULE TYPE: protein ( x i ) SEQUENCE DESCRIPTION: SEQ ID NO:30:

Ala Glu Gln Lys Leu
1               5

( 2 ) INFORMATION FOR SEQ ID NO:31:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:31:

CGGAATTCAA AGACNGGNTA CTGTNGA                        27

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:32:

Lys Thr Gly Tyr Val Asp
1               5

( 2 ) INFORMATION FOR SEQ ID NO:33:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:33:

CGGGATCCGA TCGATCNGGG TAATGATCGA TC                32

( 2 ) INFORMATION FOR SEQ ID NO:34:

( i ) SEQUENCE CHARACTERISTICS:
        ( A ) LENGTH: 6 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:34:

Asp Asp Pro Ile Asp Asp
1               5

( 2 ) INFORMATION FOR SEQ ID NO:35:

( i ) SEQUENCE CHARACTERISTICS:
        ( A ) LENGTH: 23 base pairs
        ( B ) TYPE: nucleic acid
        ( C ) STRANDEDNESS: double
        ( D ) TOPOLOGY: unknown (i i) MOLECULE TYPE: cDNA (x i) SEQUENCE DESCRIPTION: SEQ ID NO:35:

CTTTGCACGC ACGTAGGCTC CTG                                           23

(2) INFORMATION FOR SEQ ID NO:36:

(i) SEQUENCE CHARACTERISTICS:
        (A) LENGTH: 28 base pairs
        (B) TYPE: nucleic acid
        (C) STRANDEDNESS: double
        (D) TOPOLOGY: unknown (i i) MOLECULE TYPE: cDNA (x i) SEQUENCE DESCRIPTION: SEQ ID NO:36:

CGGGATCCAT CTGNCCAGTT CTTCTGTT                                      28

(2) INFORMATION FOR SEQ ID NO:37:

(i) SEQUENCE CHARACTERISTICS:
        (A) LENGTH: 13 amino acids
        (B) TYPE: amino acid
        (D) TOPOLOGY: unknown (i i) MOLECULE TYPE: protein (x i) SEQUENCE DESCRIPTION: SEQ ID NO:37:

Lys  Ile  Leu  Ala  Ala  Ile  Ile  Met  Lys  Lys  Asp  Ser  Glu
 1              5                        10

(2) INFORMATION FOR SEQ ID NO:38:

(i) SEQUENCE CHARACTERISTICS:
        (A) LENGTH: 13 amino acids
        (B) TYPE: amino acid
        (D) TOPOLOGY: unknown (i i) MOLECULE TYPE: protein (x i) SEQUENCE DESCRIPTION: SEQ ID NO:38:

Pro  Gln  Asp  Ser  Gly  His  His  His  Tyr  Glu  Lys  Arg  Leu
 1              5                        10

(2) INFORMATION FOR SEQ ID NO:39:

(i) SEQUENCE CHARACTERISTICS:
        (A) LENGTH: 4 amino acids
        (B) TYPE: amino acid
        (D) TOPOLOGY: unknown (i i) MOLECULE TYPE: protein (x i) SEQUENCE DESCRIPTION: SEQ ID NO:39:

Arg  Glu  Pro  Arg
 1